US011318015B2

(12) United States Patent
Hariton et al.

(10) Patent No.: US 11,318,015 B2
(45) Date of Patent: May 3, 2022

(54) PROSTHETIC VALVE CONFIGURED TO FILL A VOLUME BETWEEN TISSUE ANCHORS WITH NATIVE VALVE TISSUE

(71) Applicant: CARDIOVALVE LTD., Or Yehuda (IL)

(72) Inventors: Ilia Hariton, Zichron Yaackov (IL); Meni Iamberger, Kfar Saba (IL); Aviram Baum, Tel Aviv (IL); Boaz Harari, Ganey Tikva (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/135,663

(22) Filed: Sep. 19, 2018

(65) Prior Publication Data

US 2019/0083245 A1    Mar. 21, 2019

Related U.S. Application Data

(60) Provisional application No. 62/560,384, filed on Sep. 19, 2017.

(51) Int. Cl.
*A61F 2/24* (2006.01)

(52) U.S. Cl.
CPC ............ *A61F 2/2427* (2013.01); *A61F 2/243* (2013.01); *A61F 2/2436* (2013.01);
(Continued)

(58) Field of Classification Search
CPC ........ A61F 2/24; A61F 2/2418; A61F 2/2409; A61F 2/2427; A61F 2/2442;
(Continued)

(56) References Cited

U.S. PATENT DOCUMENTS

| 3,874,388 A | 4/1975 | King et al. |
| 4,222,126 A | 9/1980 | Boretos et al. |
| 4,340,091 A | 7/1982 | Skelton et al. |
| 4,972,494 A | 11/1990 | White et al. |
| 5,716,417 A | 2/1998 | Girard et al. |

(Continued)

FOREIGN PATENT DOCUMENTS

| CA | 2822801 A1 | 8/2006 |
| EP | 1264582 A2 | 12/2002 |

(Continued)

OTHER PUBLICATIONS

International Search Report dated Dec. 5, 2011, by the United States Patent and Trademark Office in PCT/IL2011/000582 (3 pages).

(Continued)

*Primary Examiner* — Paul B Prebilic
(74) *Attorney, Agent, or Firm* — Finnegan, Henderson, Farabow, Garrett & Dunner, LLP

(57) ABSTRACT

A prosthetic valve for implantation within a native mitral valve may be provided. The prosthetic valve may include an annular valve body, a plurality of atrial anchoring arms configured to extend radially outward from the annular valve body, and a plurality of ventricular anchoring legs configured to extend radially outward from the annular valve body. The arms may be configured to engage an atrial portion of the native mitral valve and the ventricular anchoring legs may be configured to engage a ventricular portion of the native mitral valve. The atrial anchoring arms and the ventricular anchoring legs may be positioned relative to each other such that when the atrial anchoring arms and ventricular anchoring legs engage the native mitral valve, a volume between the atrial anchoring arms and ventricular anchoring legs is configured to be substantially filled with tissue.

22 Claims, 21 Drawing Sheets

(52) U.S. Cl.
CPC .......... *A61F 2/2445* (2013.01); *A61F 2/2454* (2013.01); *A61F 2/2463* (2013.01); *A61F 2/246* (2013.01); *A61F 2/2409* (2013.01); *A61F 2/2418* (2013.01); *A61F 2/2466* (2013.01); *A61F 2210/0014* (2013.01); *A61F 2220/0008* (2013.01); *A61F 2250/007* (2013.01)

(58) Field of Classification Search
CPC .... A61F 2/2445; A61F 2/2463; A61F 2/2466; A61F 2220/0008; A61F 2220/0016; A61F 2230/0065; A61F 2250/001; A61F 2250/0063; A61F 2/243; A61F 2/2436; A61F 2/2454; A61F 2/246; A61F 2210/0014; A61F 2250/007
See application file for complete search history.

(56) References Cited

U.S. PATENT DOCUMENTS

| | | |
|---|---|---|
| 5,741,297 A | 4/1998 | Simon |
| 5,776,140 A | 7/1998 | Cottone |
| 5,957,949 A | 9/1999 | Leonhardt et al. |
| 6,010,530 A | 1/2000 | Goicoechea |
| 6,165,183 A | 12/2000 | Kuehn et al. |
| 6,254,609 B1 | 7/2001 | Vrba et al. |
| 6,312,465 B1 | 11/2001 | Griffin et al. |
| 6,346,074 B1 | 2/2002 | Roth |
| 6,402,780 B2 | 6/2002 | Williamson, IV et al. |
| 6,458,153 B1 | 10/2002 | Bailey et al. |
| 6,669,724 B2 | 12/2003 | Park et al. |
| 6,733,525 B2 | 5/2004 | Yang et al. |
| 6,752,813 B2 | 6/2004 | Goldfarb et al. |
| 6,755,857 B2 | 6/2004 | Peterson et al. |
| 6,926,715 B1 | 8/2005 | Hauck et al. |
| 7,074,236 B2 | 7/2006 | Rabkin et al. |
| 7,201,772 B2 | 4/2007 | Schwammenthal et al. |
| 7,226,467 B2 | 6/2007 | Lucatero et al. |
| 7,288,097 B2 | 10/2007 | Séguin |
| 7,442,204 B2 | 10/2008 | Schwammenthal et al. |
| 7,556,632 B2 | 7/2009 | Zadno |
| 7,563,267 B2 | 7/2009 | Goldfarb et al. |
| 7,563,273 B2 | 7/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,736,388 B2 | 6/2010 | Goldfarb et al. |
| 7,811,296 B2 | 10/2010 | Goldfarb et al. |
| 7,837,727 B2 | 11/2010 | Goetz et al. |
| 7,959,672 B2 | 6/2011 | Salahieh et al. |
| 8,052,592 B2 | 11/2011 | Goldfarb et al. |
| 8,057,493 B2 | 11/2011 | Goldfarb et al. |
| D652,927 S | 1/2012 | Braido et al. |
| D653,341 S | 1/2012 | Braido et al. |
| 8,109,996 B2 | 2/2012 | Stacchino et al. |
| D660,433 S | 5/2012 | Braido et al. |
| D660,967 S | 5/2012 | Braido et al. |
| 8,216,256 B2 | 7/2012 | Raschdorf, Jr. et al. |
| 8,313,525 B2 | 11/2012 | Tuval et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,585,755 B2 | 11/2013 | Chau et al. |
| 8,628,571 B1 | 1/2014 | Hacohen et al. |
| 8,652,203 B2 | 2/2014 | Quadri et al. |
| 8,657,872 B2 | 2/2014 | Seguin |
| 8,728,155 B2 | 5/2014 | Montorfano et al. |
| 8,747,460 B2 | 6/2014 | Tuval et al. |
| 8,784,481 B2 | 7/2014 | Alkhatib et al. |
| 8,852,272 B2 | 10/2014 | Gross et al. |
| 8,870,948 B1 | 10/2014 | Erzberger et al. |
| 8,870,950 B2 | 10/2014 | Hacohen |
| 8,961,595 B2 | 2/2015 | Alkhatib |
| 8,986,375 B2 | 3/2015 | Garde et al. |
| 8,992,604 B2 | 3/2015 | Hacohen et al. |
| 8,998,982 B2 | 4/2015 | Richter et al. |
| 9,017,399 B2 | 4/2015 | Hacohen et al. |
| D730,520 S | 5/2015 | Braido et al. |
| D730,521 S | 5/2015 | Braido et al. |
| 9,023,100 B2 | 5/2015 | Quadri et al. |
| D732,666 S | 6/2015 | Nguyen et al. |
| 9,050,188 B2 | 6/2015 | Schweich, Jr. et al. |
| 9,060,858 B2 | 6/2015 | Thornton et al. |
| 9,072,603 B2 | 7/2015 | Tuval et al. |
| 9,095,434 B2 | 8/2015 | Rowe |
| 9,125,740 B2 | 9/2015 | Morriss et al. |
| 9,132,009 B2 | 9/2015 | Hacohen et al. |
| 9,173,659 B2 | 11/2015 | Bodewadt et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,295,551 B2 | 3/2016 | Straubinger et al. |
| 9,295,552 B2 | 3/2016 | McLean et al. |
| 9,320,591 B2 | 4/2016 | Bolduc |
| D755,384 S | 5/2016 | Pesce et al. |
| 9,345,573 B2 | 5/2016 | Nyuli et al. |
| 9,387,078 B2 | 7/2016 | Gross et al. |
| 9,393,110 B2 | 7/2016 | Levi et al. |
| 9,439,757 B2 | 9/2016 | Wallace et al. |
| 9,445,893 B2 | 9/2016 | Vaturi |
| 9,463,102 B2 | 10/2016 | Kelly |
| 9,492,273 B2 | 11/2016 | Wallace et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich, Jr. et al. |
| 9,572,665 B2 | 2/2017 | Lane et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,763,657 B2 | 9/2017 | Hacohen et al. |
| 9,770,256 B2 | 9/2017 | Cohen et al. |
| D800,908 S | 10/2017 | Hariton et al. |
| 9,788,941 B2 | 10/2017 | Hacohen |
| 9,974,651 B2 | 5/2018 | Hariton et al. |
| 10,010,414 B2 | 7/2018 | Cooper et al. |
| 10,076,415 B1 | 9/2018 | Metchik et al. |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,226,341 B2 | 3/2019 | Gross et al. |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,357,360 B2 | 7/2019 | Hariton et al. |
| 10,376,361 B2 | 8/2019 | Gross et al. |
| 10,390,952 B2 | 8/2019 | Hariton et al. |
| 10,426,610 B2 | 10/2019 | Hariton et al. |
| 10,463,487 B2 | 11/2019 | Hariton et al. |
| 10,463,488 B2 | 11/2019 | Hariton et al. |
| 10,507,105 B2 | 12/2019 | Hariton et al. |
| 10,507,108 B2 | 12/2019 | Delgado et al. |

(56) References Cited

U.S. PATENT DOCUMENTS

| | | |
|---|---|---|
| 10,507,109 B2 | 12/2019 | Metchik et al. |
| 10,524,792 B2 | 1/2020 | Hernandez et al. |
| 10,524,903 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,646,342 B1 | 5/2020 | Marr et al. |
| 10,667,908 B2 | 6/2020 | Hariton et al. |
| 10,682,227 B2 | 6/2020 | Hariton et al. |
| 10,695,177 B2 | 6/2020 | Hariton et al. |
| 10,722,360 B2 | 7/2020 | Hariton et al. |
| 10,758,342 B2 | 9/2020 | Chau et al. |
| 10,758,344 B2 | 9/2020 | Hariton et al. |
| 10,799,345 B2 | 10/2020 | Hariton et al. |
| 10,813,760 B2 | 10/2020 | Metchik et al. |
| 10,820,998 B2 | 11/2020 | Marr et al. |
| 10,849,748 B2 | 12/2020 | Hariton et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,864,078 B2 | 12/2020 | Hariton et al. |
| 10,881,511 B2 | 1/2021 | Hariton et al. |
| 10,888,422 B2 | 1/2021 | Hariton et al. |
| 10,905,548 B2 | 2/2021 | Hariton et al. |
| 10,905,549 B2 | 2/2021 | Hariton et al. |
| 10,905,554 B2 | 2/2021 | Cao |
| 10,925,595 B2 | 2/2021 | Hacohen et al. |
| 2001/0021872 A1 | 9/2001 | Bailey et al. |
| 2002/0013571 A1 | 1/2002 | Goldfarb et al. |
| 2002/0032481 A1 | 3/2002 | Gabbay |
| 2003/0050694 A1 | 3/2003 | Yang et al. |
| 2004/0030382 A1 | 2/2004 | St. Goar et al. |
| 2004/0186558 A1 | 9/2004 | Pavcnik et al. |
| 2004/0210304 A1 | 10/2004 | Seguin et al. |
| 2004/0236354 A1 | 11/2004 | Seguin |
| 2004/0249433 A1 | 12/2004 | Freitag |
| 2005/0080474 A1 | 4/2005 | Andreas et al. |
| 2005/0085900 A1 | 4/2005 | Case et al. |
| 2005/0137681 A1 | 6/2005 | Shoemaker et al. |
| 2005/0137697 A1 | 6/2005 | Salahieh et al. |
| 2005/0203618 A1 | 9/2005 | Sharkawy et al. |
| 2005/0240200 A1 | 10/2005 | Bergheim |
| 2006/0004469 A1 | 1/2006 | Sokel |
| 2006/0020275 A1 | 1/2006 | Goldfarb et al. |
| 2006/0020327 A1 | 1/2006 | Lashinski et al. |
| 2006/0052867 A1 | 3/2006 | Revuelta et al. |
| 2006/0149360 A1* | 7/2006 | Schwammenthal .. A61F 2/2418 623/1.24 |
| 2006/0184203 A1 | 8/2006 | Martin et al. |
| 2006/0195183 A1 | 8/2006 | Navia et al. |
| 2006/0216404 A1 | 9/2006 | Seyler et al. |
| 2006/0229708 A1 | 10/2006 | Powell et al. |
| 2006/0259137 A1 | 11/2006 | Artof et al. |
| 2007/0038293 A1 | 2/2007 | St. Goar et al. |
| 2007/0056346 A1 | 3/2007 | Spenser et al. |
| 2007/0007851 A1 | 4/2007 | Ryan |
| 2007/0197858 A1 | 8/2007 | Goldfarb et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2007/0239273 A1 | 10/2007 | Allen |
| 2007/0244546 A1 | 10/2007 | Francis |
| 2008/0065011 A1 | 3/2008 | Marchand et al. |
| 2008/0071361 A1 | 3/2008 | Tuval et al. |
| 2008/0071369 A1 | 3/2008 | Tuval et al. |
| 2008/0082166 A1 | 4/2008 | Styrc et al. |
| 2008/0132989 A1 | 6/2008 | Snow et al. |
| 2008/0147182 A1 | 6/2008 | Righini et al. |
| 2008/0200980 A1 | 8/2008 | Robin et al. |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2009/0281619 A1 | 11/2009 | Le et al. |
| 2010/0023120 A1 | 1/2010 | Holecek et al. |
| 2010/0049313 A1 | 2/2010 | Alon et al. |
| 2010/0100167 A1 | 4/2010 | Bortlein et al. |
| 2010/0161036 A1 | 6/2010 | Pintor et al. |
| 2010/0256737 A1 | 10/2010 | Pollock et al. |
| 2010/0312333 A1 | 12/2010 | Navia et al. |
| 2010/0331971 A1 | 12/2010 | Keränen et al. |
| 2011/0004227 A1 | 1/2011 | Goldfarb et al. |
| 2011/0004299 A1 | 1/2011 | Navia et al. |
| 2011/0029072 A1 | 2/2011 | Gabbay |
| 2011/0066233 A1 | 3/2011 | Thornton et al. |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0224785 A1 | 9/2011 | Hacohen |
| 2011/0245911 A1 | 10/2011 | Quill et al. |
| 2011/0264196 A1 | 10/2011 | Savage et al. |
| 2011/0313515 A1 | 12/2011 | Quadri et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0059458 A1 | 3/2012 | Buchbinder |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0089223 A1 | 4/2012 | Nguyen et al. |
| 2012/0101571 A1 | 4/2012 | Thambar et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2012/0323317 A1* | 12/2012 | Karapetian ........... A61F 2/2448 623/2.37 |
| 2013/0018458 A1 | 1/2013 | Yohanan et al. |
| 2013/0046373 A1 | 2/2013 | Cartledge et al. |
| 2013/0144381 A1 | 6/2013 | Quadri et al. |
| 2013/0178930 A1 | 7/2013 | Straubinger et al. |
| 2013/0190861 A1 | 7/2013 | Chau et al. |
| 2013/0261738 A1 | 10/2013 | Clague et al. |
| 2013/0274870 A1 | 10/2013 | Lombardi et al. |
| 2013/0282059 A1 | 10/2013 | Ketai et al. |
| 2013/0304200 A1 | 11/2013 | McLean et al. |
| 2014/0000112 A1 | 1/2014 | Braido et al. |
| 2014/0018915 A1 | 1/2014 | Biadillah et al. |
| 2014/0067050 A1 | 3/2014 | Costello et al. |
| 2014/0142688 A1 | 5/2014 | Duffy et al. |
| 2014/0172077 A1 | 6/2014 | Bruchman et al. |
| 2014/0172082 A1 | 6/2014 | Bruchman et al. |
| 2014/0194981 A1 | 7/2014 | Menk et al. |
| 2014/0207231 A1 | 7/2014 | Hacohen et al. |
| 2014/0222136 A1 | 8/2014 | Geist et al. |
| 2014/0222122 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257467 A1 | 9/2014 | Lane et al. |
| 2014/0277409 A1 | 9/2014 | Bortlein et al. |
| 2014/0277411 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358224 A1 | 12/2014 | Tegels et al. |
| 2015/0018944 A1 | 1/2015 | O'Connell et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272734 A1 | 10/2015 | Sheps et al. |

(56) References Cited

U.S. PATENT DOCUMENTS

| | | |
|---|---|---|
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0158497 A1 | 6/2016 | Tran et al. |
| 2016/0184098 A1 | 6/2016 | Vaturi |
| 2016/0270911 A1 | 9/2016 | Ganesan et al. |
| 2016/0310268 A1 | 10/2016 | Oba et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0331525 A1 | 11/2016 | Straubinger et al. |
| 2016/0331526 A1 | 11/2016 | Schweich, Jr. et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0056166 A1 | 3/2017 | Ratz et al. |
| 2017/0056171 A1 | 3/2017 | Cooper et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0209264 A1 | 7/2017 | Chau et al. |
| 2017/0231759 A1 | 8/2017 | Geist et al. |
| 2017/0231766 A1 | 8/2017 | Hariton et al. |
| 2017/0239048 A1 | 8/2017 | Goldfarb et al. |
| 2017/0325948 A1 | 11/2017 | Wallace et al. |
| 2017/0333187 A1 | 11/2017 | Hariton et al. |
| 2017/0367823 A1 | 12/2017 | Hariton et al. |
| 2018/0000580 A1 | 1/2018 | Wallace et al. |
| 2018/0021129 A1 | 1/2018 | Peterson et al. |
| 2018/0028215 A1 | 2/2018 | Cohen |
| 2018/0049873 A1 | 2/2018 | Manash et al. |
| 2018/0055630 A1 | 3/2018 | Patel et al. |
| 2018/0116843 A1 | 5/2018 | Schreck et al. |
| 2018/0125644 A1 | 5/2018 | Conklin |
| 2018/0153689 A1 | 6/2018 | Maimon et al. |
| 2018/0206983 A1 | 7/2018 | Noe et al. |
| 2018/0250126 A1 | 9/2018 | O'Connor et al. |
| 2018/0250130 A1 | 9/2018 | Hariton et al. |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0289479 A1 | 10/2018 | Hariton et al. |
| 2018/0296336 A1 | 10/2018 | Cooper et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0353294 A1 | 12/2018 | Calomeni et al. |
| 2018/0360457 A1 | 12/2018 | Ellis et al. |
| 2019/0015093 A1 | 1/2019 | Hacohen et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083242 A1 | 3/2019 | Hariton et al. |
| 2019/0083243 A1 | 3/2019 | Hariton et al. |
| 2019/0083246 A1 | 3/2019 | Hariton et al. |
| 2019/0083247 A1 | 3/2019 | Hariton et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0328519 A1 | 10/2019 | Hariton et al. |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000449 A1 | 1/2020 | Goldfarb et al. |
| 2020/0000579 A1 | 1/2020 | Manash et al. |
| 2020/0015964 A1 | 1/2020 | Noe et al. |
| 2020/0030098 A1 | 1/2020 | Delgado et al. |
| 2020/0046497 A1 | 2/2020 | Hariton et al. |
| 2020/0054335 A1 | 2/2020 | Hernandez et al. |
| 2020/0054451 A1 | 2/2020 | Hariton et al. |
| 2020/0060818 A1 | 2/2020 | Geist et al. |
| 2020/0069424 A1 | 3/2020 | Hariton et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0129294 A1 | 4/2020 | Hariton et al. |
| 2020/0138567 A1 | 5/2020 | Marr et al. |
| 2020/0146671 A1 | 5/2020 | Hacohen et al. |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0253600 A1 | 8/2020 | Darabian |
| 2020/0261094 A1 | 8/2020 | Goldfarb et al. |
| 2020/0315786 A1 | 10/2020 | Metchik et al. |
| 2020/0337842 A1 | 10/2020 | Metchik et al. |

FOREIGN PATENT DOCUMENTS

| | | |
|---|---|---|
| EP | 1637092 A2 | 3/2006 |
| EP | 2349124 B1 | 10/2018 |
| EP | 3583922 A1 | 12/2019 |
| EP | 3270825 B1 | 4/2020 |
| EP | 2485795 B1 | 9/2020 |
| WO | WO 2003/020179 A1 | 3/2003 |
| WO | WO 2004/028399 A2 | 4/2004 |
| WO | WO 2006/007389 A1 | 1/2006 |
| WO | WO 2006/086434 A1 | 8/2006 |
| WO | WO 2006/116558 A2 | 11/2006 |
| WO | WO 2007/047488 A2 | 4/2007 |
| WO | WO 2008/029296 A2 | 3/2008 |
| WO | WO 2009/091509 A1 | 7/2009 |
| WO | WO 2010/006627 A1 | 1/2010 |
| WO | WO 2010/027485 A1 | 3/2010 |
| WO | WO 2010/045297 A2 | 4/2010 |
| WO | WO 2010/057262 A1 | 5/2010 |
| WO | WO 2011/144351 A1 | 11/2011 |
| WO | WO 2012/011108 A2 | 1/2012 |
| WO | WO 2012/036740 A2 | 3/2012 |
| WO | WO 2012/048035 A2 | 4/2012 |
| WO | WO 2013/059747 A1 | 4/2013 |
| WO | WO 2013/072496 A1 | 5/2013 |
| WO | WO 2013/078497 A1 | 6/2013 |
| WO | WO 2013/175468 A2 | 11/2013 |
| WO | WO 2014/115149 A2 | 7/2014 |
| WO | WO 2014/144937 A2 | 9/2014 |
| WO | WO 2014/164364 A1 | 10/2014 |
| WO | WO 2016/016899 A1 | 2/2016 |
| WO | WO 2016/098104 A2 | 6/2016 |
| WO | WO 2016/125160 A1 | 8/2016 |
| WO | WO 2018/025260 A1 | 2/2018 |
| WO | WO 2018/025263 A2 | 2/2018 |
| WO | WO 2018/029680 A1 | 2/2018 |
| WO | WO 2018/039631 A1 | 3/2018 |
| WO | WO 2018/112429 A1 | 6/2018 |
| WO | WO 2018/118717 A1 | 6/2018 |
| WO | WO 2018/131042 A1 | 7/2018 |
| WO | WO 2018/131043 A1 | 7/2018 |
| WO | WO 2019/195860 A2 | 10/2019 |
| WO | WO 2020/167677 A1 | 8/2020 |

OTHER PUBLICATIONS

International Search Report dated Mar. 27, 2018, by the European Patent Office in PCT/IL2017/050849 (5 pages).

(56) References Cited

OTHER PUBLICATIONS

International Search Report dated May 30, 2016, by the European Patent Office in PCT/IL2016/050125 (6 pages).
International Search Report dated Nov. 24, 2017, by the European Patent Office in PCT/IL2017/050873 (5 pages).
International Search Report dated Oct. 27, 2015, by the European Patent Office in PCT/IL2015/050792 (3 pages).
International Search Report dated Sep. 4, 2014, by the European Patent Office in PCT/IL2014/050087 (6 pages).
Batista, Randas J. V. et al., *Partial Left Ventriculectomy to Treat End-Stage Heart Disease*, 64 Annals Thoracic Surgery 634-38 (1997) (5 pages).
Beall, Jr., Arthur C. et al., *Clinical Experience with a Dacron Velour-Covered Teflon-Disc Mitral-Valve Prosthesis*, 5 Annals Thoracic Surgery 402-10 (1968) (9 pages).
Fucci, Carlo et al., *Improved Results with Mitral Valve Repair Using New Surgical Techniques*, 9 Eur. J. Cardiothoracic Surgery 621-27 (1995) (7 pages).
Maisano, Francesco et al., *The Edge-To-Edge Technique: A Simplified Method to Correct Mitral Insufficiency*, 13 Eur. J. Cardiothoracic Surgery 240-46 (1998) (7 pages).
Stone, Gregg W. et al., *Clinical Trial Design Principles and Endpoint Definitions for Transcatheter Mitral Valve Repair and Replacement: Part 1: Clinical Trial Design Principles*, 66 J. Am. C. Cardiology 278-307 (2015) (30 pages).
Sündermann, Simon H. et al., *Feasibility of the Engager™ aortic transcatheter valve system using a flexible over-the-wire design*, 42 Eur. J. Cardiothoracic Surgery e48-e52 (2012) (5 pages).
Symetis S.A., Clinical Investigation Plan for ACURATE Neo™ TA Delivery System, Protocol 2015-01, ver. 2, ClinicalTrials.gov Identifier NCT02950428, Sep. 8, 2015 (76 pages).
Tchetche, Didier et al., *New-generation TAVI devices: description and specifications*, 10 EuroIntervention (Supplement) U90-U100 (2014) (11 pages).
*Edwards Lifesciences Corp.v. Cardiovalve Ltd.*, IPR2021-00383, Paper 10: Decision Granting Institution Of Inter Partes Review (Dec. 10, 2021) (42 pages).
*Edwards Lifesciences Corp.v. Cardiovalve Ltd.*, IPR2021-00383, Petitioners' Opposition to Patent Owner's Contingent Motion to Amend (Jan. 5, 2022) (32 pages).
*Edwards Lifesciences Corp.v. Cardiovalve Ltd.*, IPR2021-00383, Petitioners' Reply to Patent Owner's Response (Jan. 5, 2022) (41 pages).

* cited by examiner

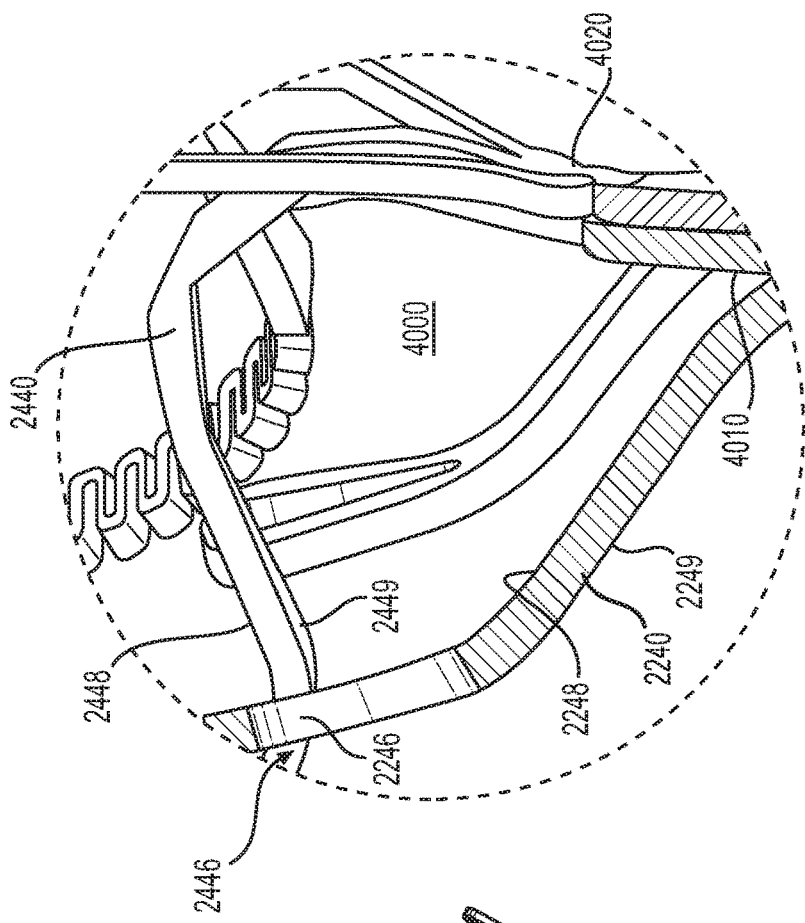
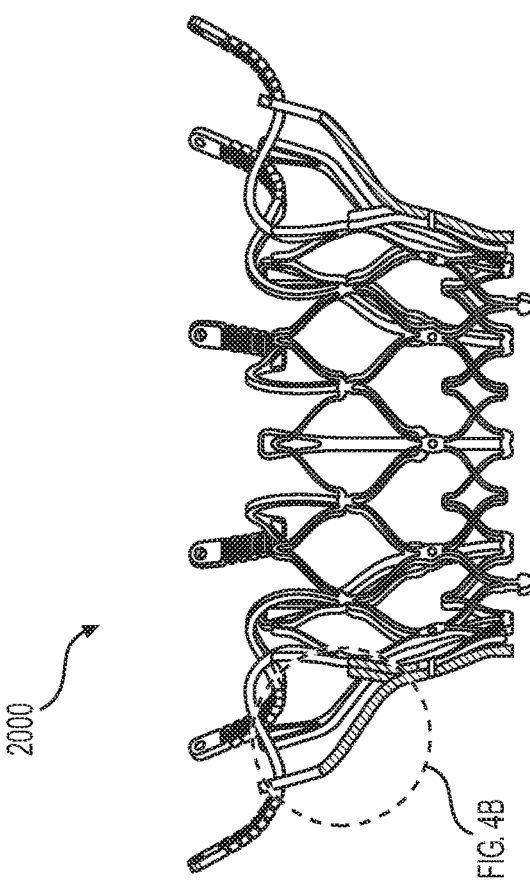
FIG. 4B
FIG. 4A

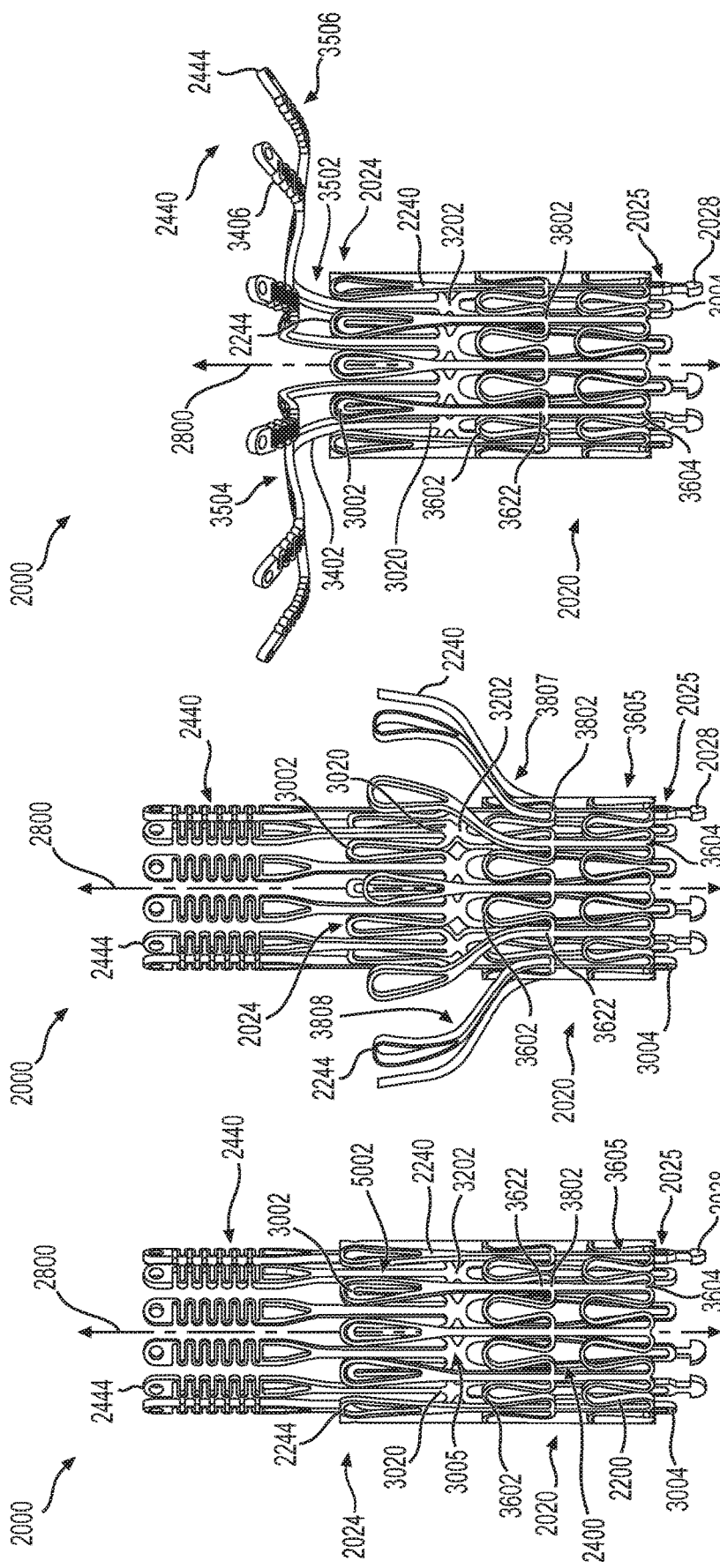

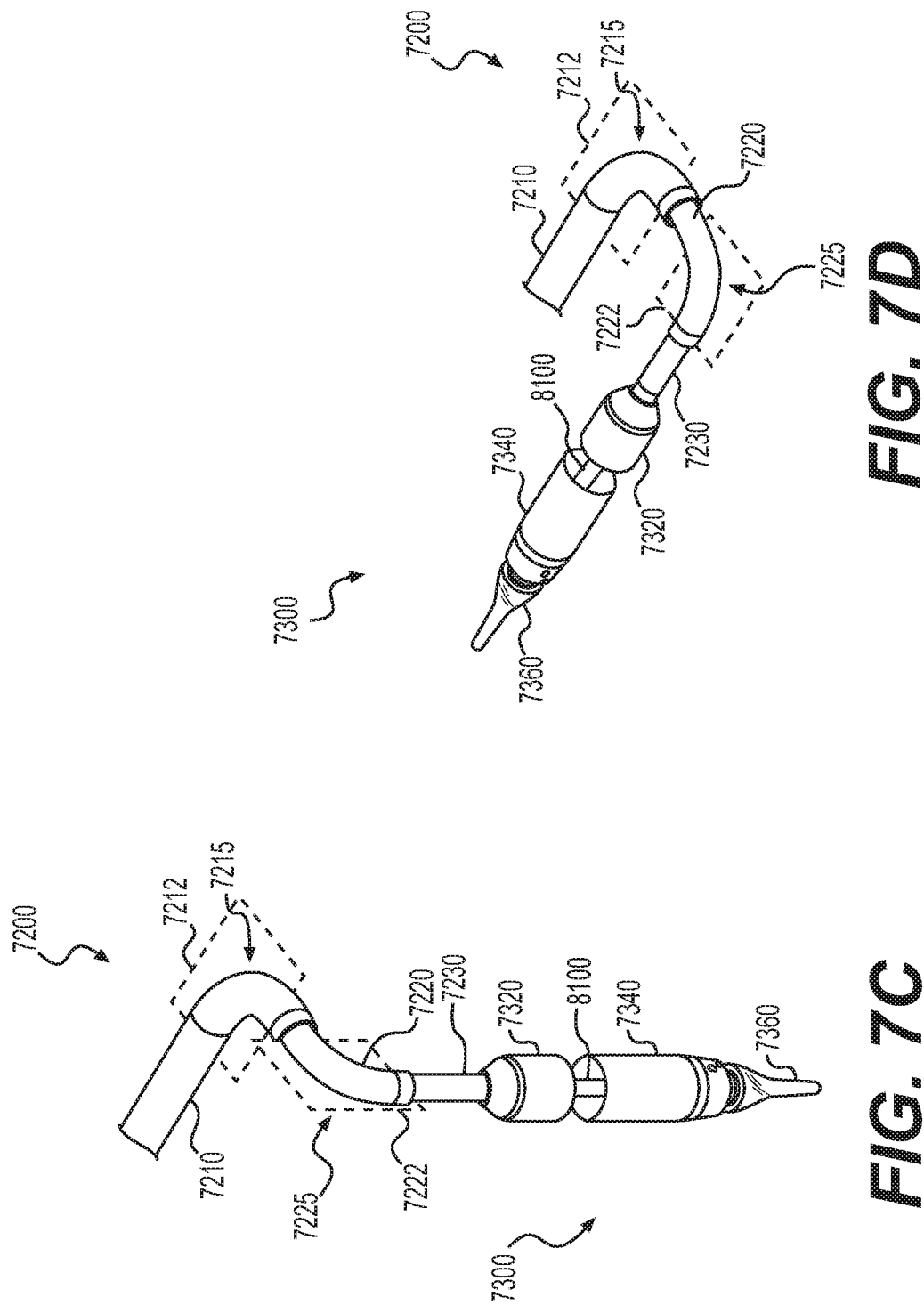

PROSTHETIC VALVE CONFIGURED TO FILL A VOLUME BETWEEN TISSUE ANCHORS WITH NATIVE VALVE TISSUE

CROSS-REFERENCE TO RELATED APPLICATION

This application claims priority from U.S. Provisional Patent Application No. 62/560,384, filed Sep. 19, 2017, which is hereby incorporated by reference in its entirety.

TECHNICAL FIELD

This disclosure relates generally to prosthetic valves and delivery systems for prosthetic valves. More specifically, this disclosure relates to prosthetic heart valves and methods thereof.

BACKGROUND

The native heart valves (the tricuspid valve, pulmonary valve, mitral valve, and aortic valve) play an important role in regulating flow of blood through the cardiovascular system. However, the native heart valves may become damaged or impaired, such as due to cardiovascular diseases, infections, or congenital malformations, thus limiting the ability of the native heart valves to regulate blood flow. This deficiency may result in reduced cardiovascular function or even death.

To treat these conditions, prosthetic heart valves may be implanted at or near the site of a damaged or impaired native valve. A prosthetic heart valve may assist or replace the functionality of an impaired native valve, leading to better regulation of blood flow and improved cardiovascular function. However, many existing prosthetic heart valves require implantation via an open heart procedure, which is highly-invasive and may cause life-threatening complications. Other prosthetic valves may be collapsed within a prosthetic valve delivery system and advanced into the heart, at which point the prosthetic valve may be removed from the delivery system and expanded at the native valve site. However, many of these prosthetic valves are large in size and therefore difficult to deliver into the heart without causing damage to healthy tissue along the implantation route. In addition, once these prosthetic valves are situated within the heart, they may be difficult to securely implant at the native valve site due to their complex structure and the limited maneuverability of existing prosthetic valve delivery systems within the heart. Moreover, many prosthetic valves are so large that they may protrude several centimeters into surrounding heart chambers once they are implanted, impairing cardiac filling and causing injury to the anatomy within the heart.

Thus, there remains a need for prosthetic heart valves which are smaller in size while still configured to assist or replace the functionality of a diseased or damaged native heart valve. In addition, there remains a need for prosthetic heart valves which are more easily maneuvered into the heart and securely implanted at the site of a native heart valve. Moreover, there remains a need for improved prosthetic heart valve delivery systems which are configured to securely implant a prosthetic heart valve at an implantation site. The present disclosure provides prosthetic heart valves with a reduced axial length such that the prosthetic heart valves may be more easily delivered into the heart and may exhibit lower protrusion into the chambers of the heart. The present disclosure also provides improved prosthetic heart valve delivery systems and methods of implanting prosthetic heart valves therewith, such that prosthetic heart valves may be securely anchored at the implantation site.

SUMMARY

Disclosed herein are prosthetic valves for implantation within a native valve and methods thereof. Particular examples of the disclosure may pertain to a prosthetic valve including a plurality of tissue anchors, where the tissue anchors are configured to be positioned relative to each other such that when the prosthetic valve is implanted, a volume between the tissue anchors is configured to be substantially filled with tissue.

According to an exemplary embodiment of the present disclosure, a prosthetic valve for implantation within a native mitral valve is provided. The prosthetic valve includes an annular valve body. The prosthetic valve also includes a plurality of atrial anchoring arms configured to extend radially outward from the annular valve body. The arms are configured to engage an atrial portion of the native mitral valve. The prosthetic valve also includes a plurality of ventricular anchoring legs configured to extend radially outward from the annular valve body. The ventricular anchoring legs are configured to engage a ventricular portion of the native mitral valve. The atrial anchoring arms and the ventricular anchoring legs are positioned relative to each other such that when the atrial anchoring arms and ventricular anchoring legs engage the native mitral valve, a volume between the atrial anchoring arms and ventricular anchoring legs is configured to be substantially filled with tissue.

The atrial anchoring arms and the ventricular anchoring legs are positioned relative to each other such that when the atrial anchoring arms and ventricular anchoring legs engage the native mitral valve, the volume between the atrial anchoring arms and ventricular anchoring legs is substantially devoid of gaps. The volume between the atrial anchoring arms and ventricular anchoring legs is formed between an outer surface of the annular valve body, surfaces of the ventricular anchoring legs facing toward an atrium, and surfaces of the atrial anchoring arms facing toward a ventricle. A portion of at least one ventricular anchoring leg is configured to be substantially aligned in a common lateral plane with a portion of at least one atrial anchoring arm. A circumference formed by the portion of the at least one ventricular anchoring leg and the portion of the at least one atrial anchoring arm forms an outer boundary of the volume between the atrial anchoring arms and ventricular anchoring legs. At least one atrial anchoring arm includes a first portion configured to extend toward a ventricle, and a second portion configured to extend toward an atrium. The first portion of the at least one atrial anchoring arm is configured to form a boundary of the volume between the atrial anchoring arms and ventricular anchoring legs. The second portion is situated radially outward from the volume between the atrial anchoring arms and ventricular anchoring legs. The second portion is situated radially outward from the first portion. The first portion has a flexibility that varies from a radially inner end of the first portion to a radially outer end of the first portion. A diameter of an outer circumference defined by terminal ends of the ventricular anchoring legs is between 1.6 and 1.8 times larger than a diameter of an inner circumference of the annular valve body. The inner circumference of the annular valve body is defined by an inner surface of the annular valve body to which prosthetic leaflets are coupled. The atrial anchoring arms and ventricular anchoring legs are angularly offset from each other. At least one ventricular anchoring leg includes at least one curved portion. A radially inner-most portion of at least one atrial anchoring arm is configured to extend toward an atrium. The entire length of at least one ventricular anchoring leg is configured to extend toward an atrium. The annular valve body includes an atrial end, a ventricular end opposite the atrial end, and an intermediate portion extending between the atrial end and the ventricular end. The atrial anchoring arms and ventricular anchoring legs are configured to extend from the intermediate portion. The annular valve body includes an annular outer frame and an inner frame situated at least partially within the annular outer frame. The atrial anchoring arms extend from the inner frame and the ventricular anchoring legs extend from the annular outer frame. The atrial anchoring arms are configured to transition between a radially-contracted configuration and a radially-expanded configuration independent of the ventricular anchoring legs. The radially-contracted configuration is a delivery configuration and the radially-expanded configuration is a deployed configuration. The volume between the atrial anchoring arms and ventricular anchoring legs is greater when the annular valve body is configured in a radially-contracted configuration than when the annular valve body is configured in a radially-expanded configuration. The radially-contracted configuration is a delivery configuration and the radially-expanded configuration is a deployed configuration. The volume between the atrial anchoring arms and ventricular anchoring legs of the annular valve body decreases after the annular valve body radially expands.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 4A illustrates a cross-sectional view of the exemplary frame of FIG. 2A, consistent with various embodiments of the present disclosure.

FIG. 4B illustrates an enlarged view of a volume between an atrial anchoring arm and a ventricular anchoring leg of the exemplary frame of FIG. 4A, consistent with various embodiments of the present disclosure.

FIGS. 5A-5E illustrate structural changes in the exemplary frame of FIG. 2A during transitioning of the frame between a radially-contracted configuration and a radially-expanded configuration, consistent with various embodiments of the present disclosure.

FIG. 7C illustrates an exemplary configuration of a telescoping catheter assembly and the delivery capsule of the exemplary prosthetic valve delivery system of FIG. 7A, consistent with various embodiments of the present disclosure.

FIG. 7D illustrates another exemplary configuration of the telescoping catheter assembly and delivery capsule of FIG. 7C, consistent with various embodiments of the present disclosure.

DETAILED DESCRIPTION

Figure 1A:
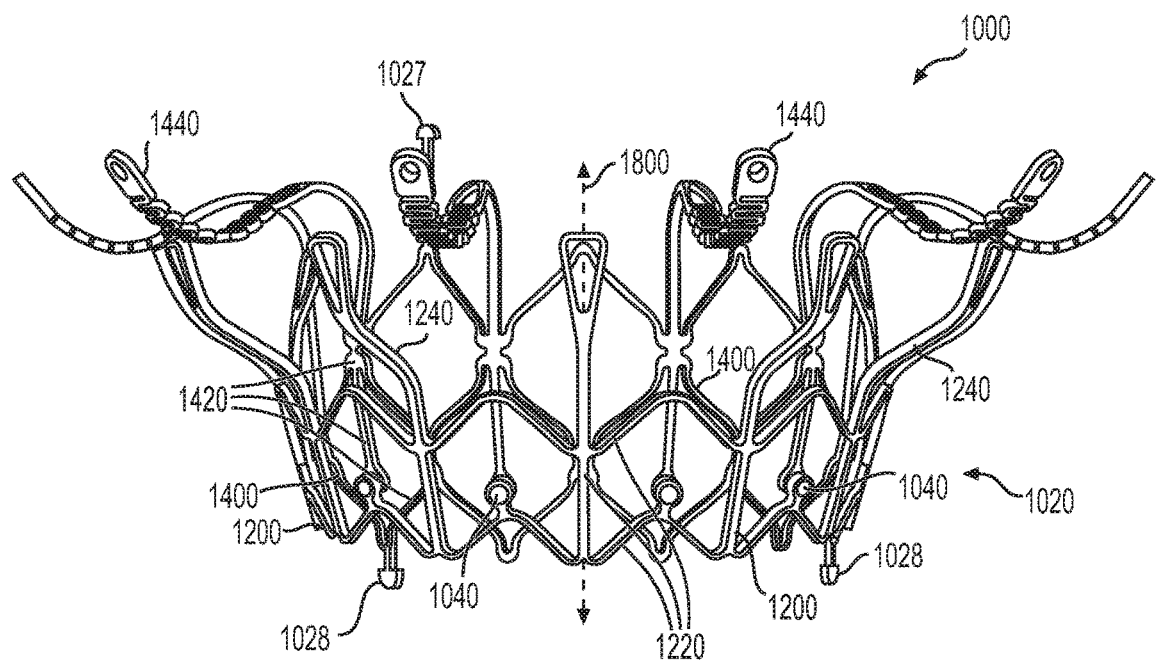
FIG. 1A illustrates a front elevation view of an exemplary frame for a prosthetic valve, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

In some embodiments of the present disclosure, an "atrial direction" may refer to a direction extending towards an atrium of the heart. For example, from a location within the left ventricle or the mitral valve, an atrial direction may refer to a direction extending towards the left atrium. Additionally, from a location within an atrium (e.g., the left atrium), an atrial direction may refer to a direction extending away from an adjacent atrioventricular valve (e.g., the mitral valve) and further into the atrium. For example, in FIGS. 10G and 10H, an atrial direction may refer to a direction extending upwards from prosthetic valve 6000 towards atrium 9010. In some exemplary embodiments, an atrial direction need not necessarily be parallel to a longitudinal axis of a prosthetic valve (e.g., longitudinal axis 2800 illustrated in FIG. 2A), so long as the direction is angled towards an atrium. The atrial direction may be parallel to a longitudinal axis of a prosthetic valve in some cases. In some embodiments, a "non-ventricular direction" may refer to a direction that does not extend towards a ventricle of the heart. A "non-ventricular direction" may extend in an atrial direction, or it may extend laterally in a direction perpendicular to a ventricular direction.

In some exemplary embodiments of the present disclosure, a "ventricular direction" may refer to a direction extending towards a ventricle of the heart. From a location within the left atrium or the mitral valve, a ventricular direction may refer to a direction extending towards the left ventricle. Additionally, from a location within a ventricle (e.g., the left ventricle), a ventricular direction may refer to a direction extending away from an adjacent atrioventricular valve (e.g., the mitral valve) and further into the ventricle. For example, in FIGS. 10G and 10H, a ventricular direction may refer to a direction extending downwards from prosthetic valve 6000 towards ventricle 9020. In some exemplary embodiments, a ventricular direction need not necessarily be parallel to a longitudinal axis of a prosthetic valve (e.g., longitudinal axis 2800 illustrated in FIG. 2A), so long as the direction is angled towards a ventricle. The ventricular direction may be parallel to a longitudinal axis of a prosthetic valve in some cases. In some embodiments, a "non-atrial direction" may refer to a direction that does not extend towards an atrium of the heart. A non-atrial direction may extend in a ventricular direction, or it may extend laterally in a direction perpendicular to an atrial direction.

Exemplary embodiments generally relate to prosthetic valves for implantation within a native valve and methods for implanting prosthetic valves within a native valve. In addition, exemplary embodiments generally relate to systems and methods for implantation of prosthetic valves by prosthetic valve delivery systems. While the present disclosure provides examples relating to prosthetic heart valves, and in particular prosthetic mitral valves, as well as delivery systems for prosthetic heart valves, it should be noted that aspects of the disclosure in their broadest sense are not limited to a prosthetic heart valve. Rather, the foregoing principles may be applied to other prosthetic valves as well. In various embodiments in accordance with the present disclosure, the term prosthetic valve refers generally to an implantable valve configured to restore and/or replace the functionality of a native valve, such as a diseased or otherwise impaired native heart valve.

An exemplary prosthetic valve may include a prosthetic valve configured to render a native valve structure non-functional, and may thus replace the function of the native valve. For example, an exemplary prosthetic valve may have a size and shape similar to the valve being replaced and may include a number of leaflet-like structures to regulate fluid flow and prevent backflow of blood through the valve. Additionally, or alternatively, an exemplary prosthetic valve may also include a prosthetic valve configured to leave the native valve structure intact and functional. An exemplary prosthetic valve may include a mitral valve, tricuspid valve, aortic valve, or pulmonary valve, as well as a valve outside of the heart, such as a venous valve, lymph node valve, ileocecal valve, or any other structure configured to control and/or regulate fluid flow in the body. An exemplary prosthetic valve may additionally or alternatively be configured to replace a failed bioprosthesis, such as a failed heart valve prosthesis.

Figure 1B:
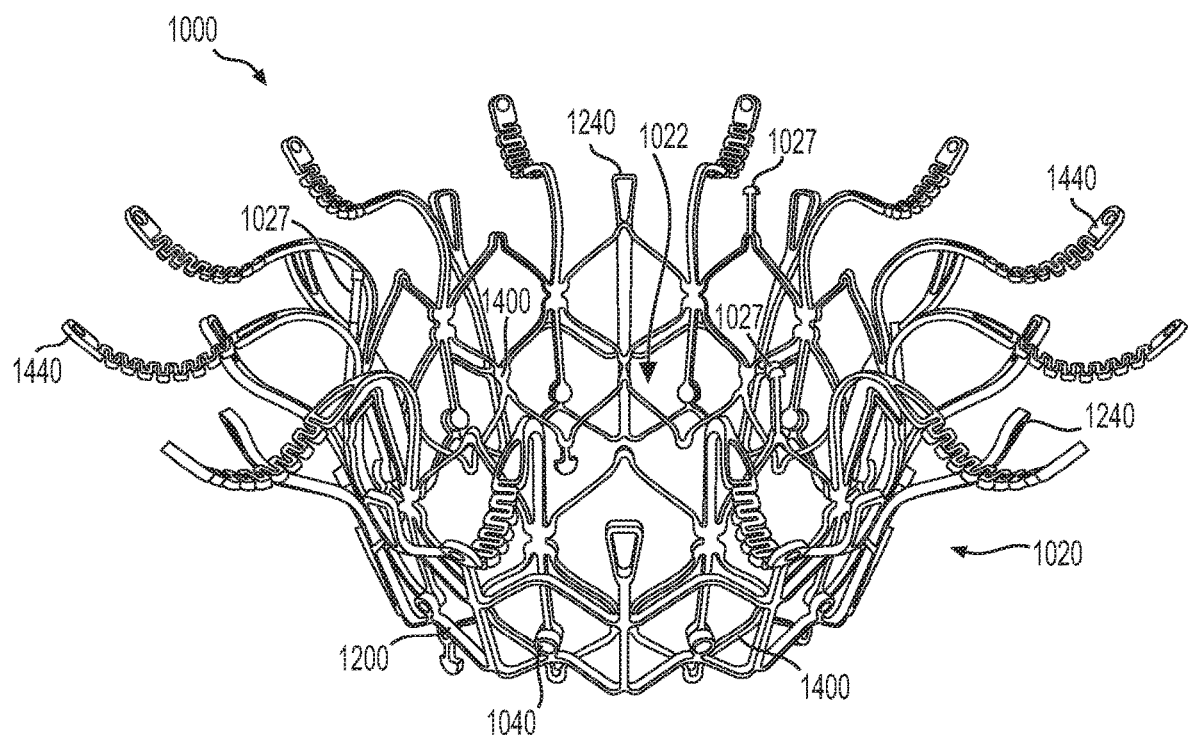
FIG. 1B illustrates a perspective view of the exemplary frame of FIG. 1A, consistent with various embodiments of the present disclosure.

FIG. 1A illustrates a front elevation view of an exemplary frame 1000 for a prosthetic valve. FIG. 1B illustrates a perspective view of frame 1000. Frame 1000 may be constructed of a shape memory material such as nickel titanium alloy (Nitinol) and may be configured to support other components of the prosthetic valve, such as prosthetic leaflets and protective cover layers. Frame 1000 may include an annular outer frame 1200 and an inner frame 1400 situated at least partially within the outer frame 1200. Annular outer frame 1200 and inner frame 1400 may be secured together by pins, screws, welding, soldering, adhesive, magnets, and/or any other suitable mechanism. For example, FIGS. 1A and 1B depict annular outer frame 1200 and inner frame 1400 connected by a plurality of connector pins 1040.

Annular outer frame 1200 may include an outer frame tubular portion 1220, which may be formed of a plurality of struts intersecting at junctions to form a wire mesh, stent-like, or cage-like structure of the outer frame tubular portion 1220. Annular outer frame 1200 may also include at least one ventricular anchoring leg 1240, which may be configured to extend radially outward from the outer frame tubular portion and which may contact, or otherwise engage, tissue within or near the native valve to anchor the prosthetic valve within the native valve. In some embodiments, exemplary valve frame 1000 may include twelve ventricular anchoring legs 1240, which may be configured to engage ventricular tissue of a native atrioventricular valve.

Inner frame 1400 may include an inner frame tubular portion 1420, which may be formed of a plurality of struts intersecting at junctions to form a wire mesh, stent-like, or cage-like structure of the inner frame tubular portion 1420. Inner frame 1400 may also include at least one atrial anchoring arm 1440, which may be configured to extend radially outward from the inner frame tubular portion and which may contact, or otherwise engage, tissue within or near the native valve to anchor the prosthetic valve within the native valve. In some embodiments, exemplary valve frame 1000 may include twelve atrial anchoring arms 1440, which may be configured to engage atrial tissue of a native atrioventricular valve.

Outer frame tubular portion 1220 and inner frame tubular portion 1420 may together form an annular valve body 1020 of the prosthetic valve, which may have at least one opening and from which the ventricular anchoring legs 1240 and atrial anchoring arms 1440 may extend. Annular valve body 1020 may include an axial lumen 1022 extending through the annular valve body 1020 along a longitudinal axis 1800 of the prosthetic valve. In some embodiments, annular valve body 1020 may be configured to receive a flow control device, such as one or more prosthetic leaflets, within axial lumen 1022. Optionally, annular valve body 1020 may include one or more atrial end delivery posts 1027 along an atrial end (i.e., top end) of the annular valve body and/or one or more ventricular end delivery posts 1028 along a ventricular end (i.e., bottom end) of the annular valve body. Delivery posts 1027 and 1028 may be configured to removably engage a delivery device of the prosthetic valve, for example, to assist with placement of frame 1000 within or near a native valve.

Figure 2A:
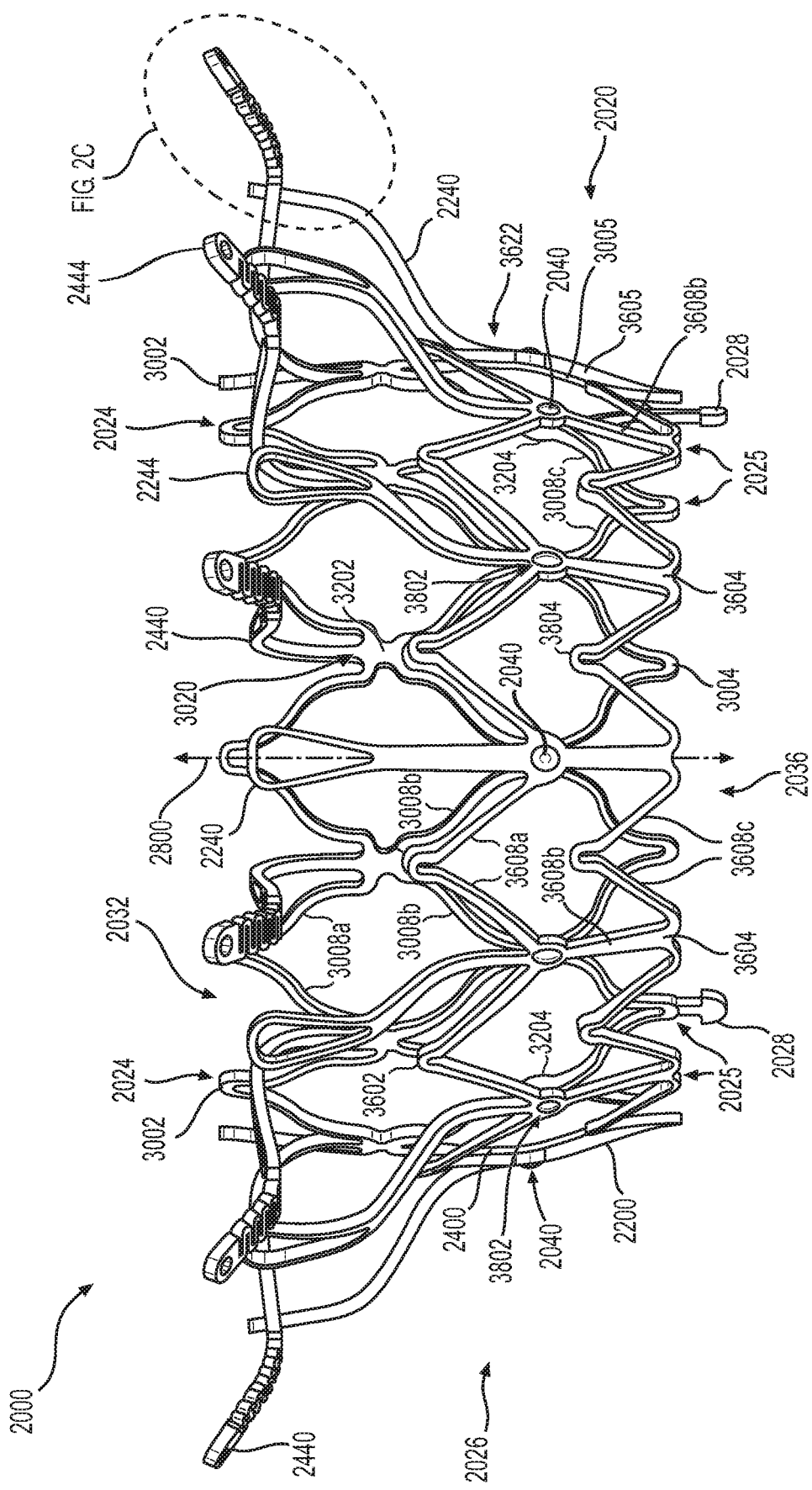
FIG. 2A illustrates a front elevation view of another exemplary frame for a prosthetic valve, consistent with various embodiments of the present disclosure.
Figure 2B:
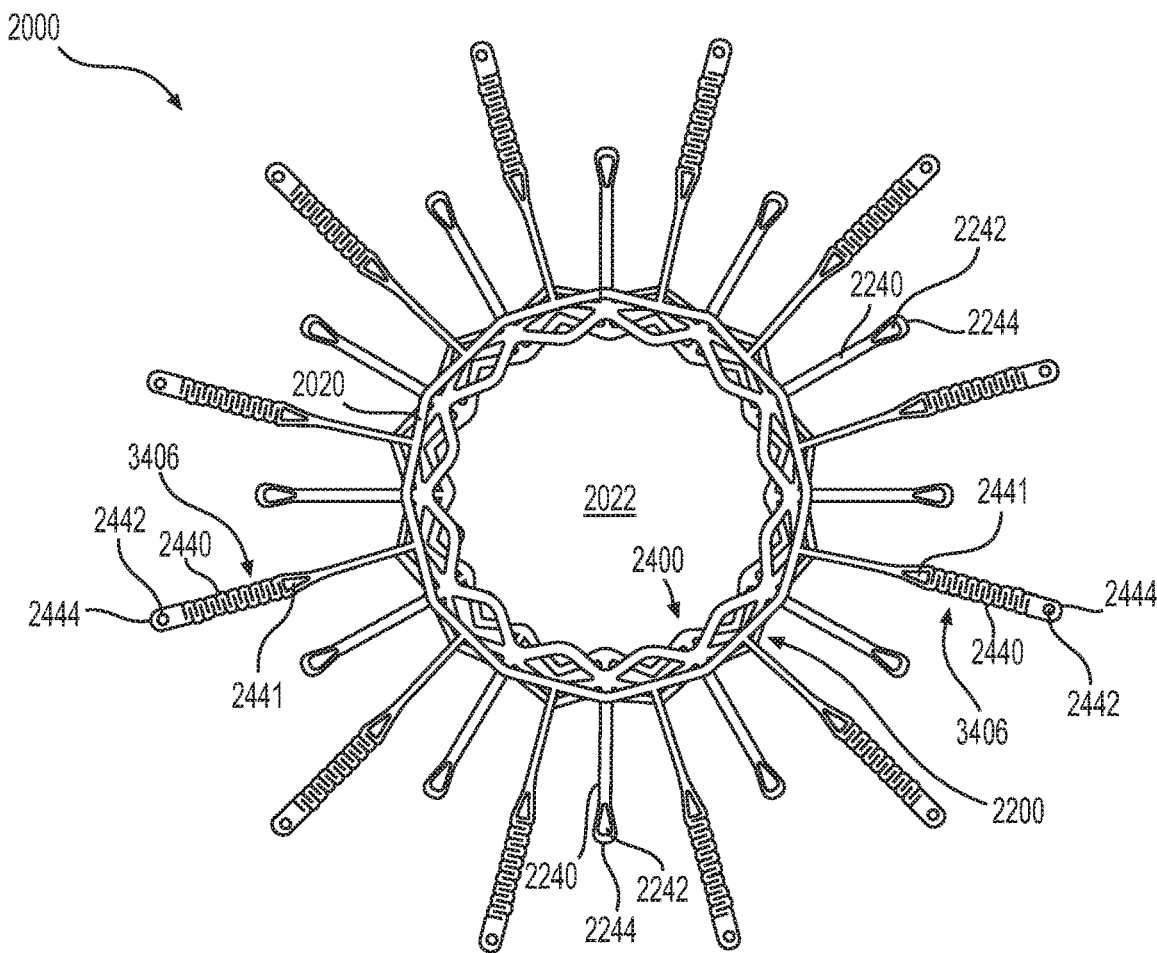
FIG. 2B illustrates a top plan view of the exemplary frame of FIG. 2A, consistent with various embodiments of the present disclosure.

FIG. 2A illustrates a front view of another exemplary frame 2000 for a prosthetic valve. FIG. 2B illustrates a top plan view of the frame 2000. Frame 2000 may include an annular outer frame 2200 and an inner frame 2400 situated at least partially within the annular outer frame 2200. Annular outer frame 2200 and inner frame 2400 may be secured together by pins, screws, welding, soldering, adhesive, magnets, and/or any other suitable mechanism. For example, FIGS. 2A and 2B depict annular outer frame 2200 and inner frame 2400 connected by a plurality of connector pins 2040.

Annular outer frame 2200 may include an outer frame tubular portion 3605, which may be formed of a plurality of struts intersecting at junctions to form a wire mesh, stent-like, or cage-like structure of the outer frame tubular portion 3605. For example, as illustrated in FIG. 2A, annular outer frame 2200 may include outer frame atrial circumferential struts 3608*a*, outer frame leg base struts 3608*b*, and outer frame ventricular circumferential struts 3608*c* intersecting at atrial end outer frame junctions 3602, leg attachment junctions 3802, outer frame junctions 3804, and ventricular end outer frame junctions 3604 to form outer frame tubular portion 3605. Annular outer frame 2200 may also include at least one ventricular anchoring leg 2240, which may extend from leg attachment junction 3802 of the outer frame tubular portion 3605 and which may be configured to engage ventricular tissue of a native valve to anchor the prosthetic valve in the native valve. The at least one ventricular anchoring leg 2240 may include a proximal leg end 3622, which may be the end of the leg connected to the outer frame tubular portion, and a distal leg end 2244, which may be situated radially outward from the outer frame tubular portion. As shown in FIG. 2B, the at least one ventricular anchoring leg 2240 may include at least one opening 2242.

Inner frame 2400 may include an inner frame tubular portion 3005, which may be formed of a plurality of struts intersecting at junctions to form a wire mesh, stent-like, or cage-like structure of the inner frame tubular portion 3005. For example, as illustrated in FIG. 2A, inner frame 2400 may include inner frame atrial struts 3008*a*, inner frame intermediate struts 3008*b*, and inner frame ventricular struts 3008*c* intersecting at atrial end inner frame junctions 3002, arm attachment junctions 3202, inner frame strut junctions 3204, and ventricular end inner frame junctions 3004 to form inner frame tubular portion 3005. Inner frame 2400 may also include at least one atrial anchoring arm 2440, which may extend from arm attachment junction 3202 of the inner frame tubular portion 3005 and which may be configured to engage atrial tissue of a native valve to anchor the prosthetic valve in the native valve. The at least one atrial anchoring arm 2440 may include a proximal arm end 3020, which may be the end of the arm connected to the inner frame tubular portion, and a distal arm end 2444, which may be situated radially outward from the inner frame tubular portion. As shown in FIG. 2B, the at least one atrial anchoring arm 2440 may include a proximal arm opening 2441 and a distal arm opening 2442.

Outer frame tubular portion 3605 and inner frame tubular portion 3005 may together form an annular valve body 2020 of the prosthetic valve, which may have at least one opening and from which the ventricular anchoring legs 2240 and atrial anchoring arms 2440 may extend. Annular valve body 2020 may include an axial lumen 2022 extending through the annular valve body 2020 along a longitudinal axis 2800 of the prosthetic valve. Annular valve body 2020 may have an atrial end 2024, a ventricular end 2025 opposite the atrial end, and an intermediate portion 2026 extending between the atrial and ventricular ends. In some embodiments, the atrial end may refer to the portion of the annular valve body configured to be situated at a location within the atrium that is furthest from an adjacent ventricle, when the prosthetic valve is implanted in a native valve. Similarly, the ventricular end may refer to the portion of the annular valve body configured to be situated at a location within the ventricle that is furthest from an adjacent atrim, when the prosthetic valve is implanted in a native valve. The intermediate portion 2026 may extend between the atrial end 2024 and ventricular end 2025. In some embodiments, annular valve body 2020 may include one or more ventricular end delivery posts 1028 along the ventricular end 2025 of the annular valve body. Axial lumen 2022 may include an inlet opening 2032 at the atrial end of the annular valve body, as well as an outlet opening 2036 at the ventricular end of the annular valve body.

Figure 2C:
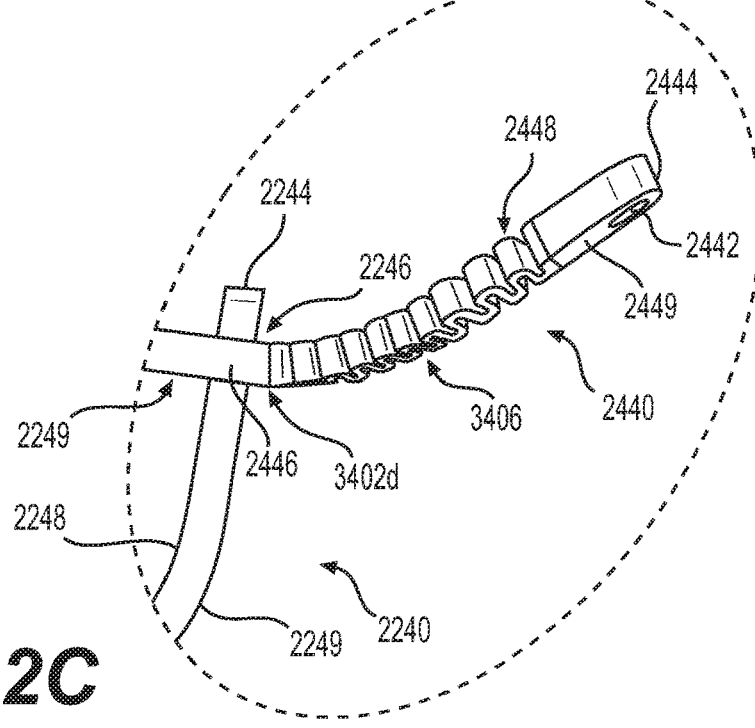
FIG. 2C illustrates an enlarged view of an atrial anchoring arm and a ventricular anchoring leg of the exemplary frame of FIG. 2A, consistent with various embodiments of the present disclosure.

FIG. 2C illustrates an enlarged view of an atrial anchoring arm 2440 and a ventricular anchoring leg 2240 of frame 2000. Ventricular anchoring leg 2240 may include an inner, atrially-facing leg surface 2248 and an outer, ventricularly-facing leg surface 2249. Atrial anchoring arm 2440 may include an atrially-facing arm surface 2448 and a ventricularly-facing arm surface 2449. In some embodiments, atrial anchoring arm 2440 may include an arm portion 2446 configured to be arranged in a common lateral plane with leg portion 2246 of the ventricular anchoring leg 2240. That is, leg portion 2246 and arm portion 2446 may be positioned at the same axial position along longitudinal axis 2800.

Figure 2D:
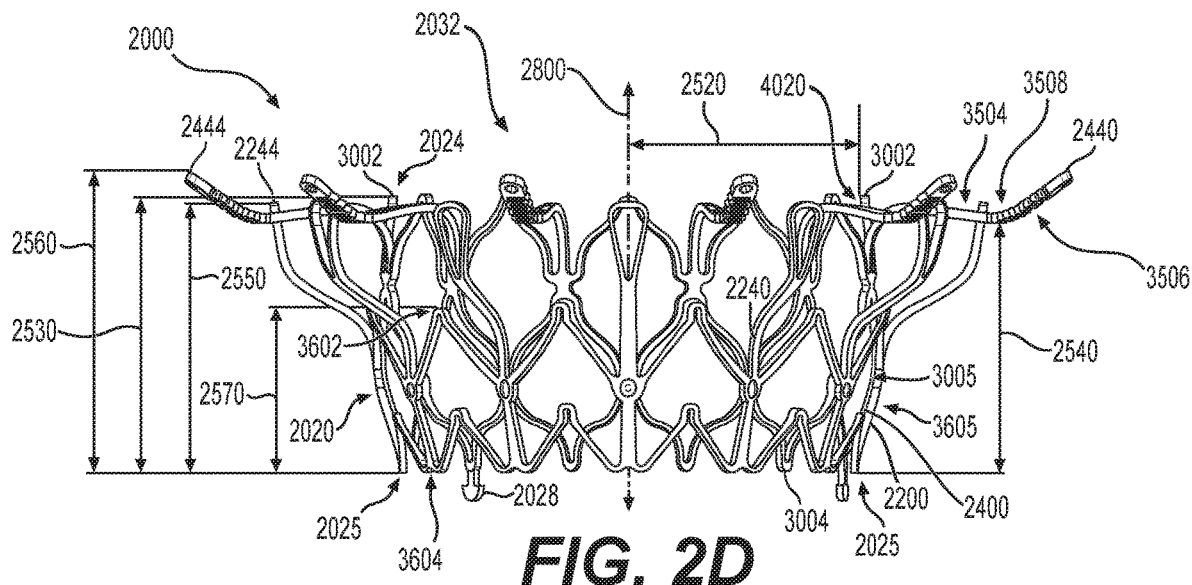
FIG. 2D illustrates another front elevation view of the exemplary frame of FIG. 2A, consistent with various embodiments of the present disclosure.

FIG. 2D illustrates another front elevation view of frame 2000. The exemplary prosthetic valve, as well as frame 2000, may have an axial height 2560, which may extend between terminal arm ends 2444 and ventricular end 2025 of the annular valve body. Inner frame tubular portion 3005 may have an axial height 2530, which may extend between atrial end inner frame junctions 3002 and ventricular end inner frame junctions 3004. Annular outer frame 2200 may have an axial height 2550, which may extend between terminal leg ends 2244 and ventricular end 2025 of the annular valve body. Outer frame tubular portion 3605 may have an axial height 2570, which may extend between atrial end outer frame junctions 3602 and ventricular end outer frame junctions 3604. In some embodiments, frame 2000 may have a ventricular device protrusion distance 2540, which may represent the distance over which the prosthetic valve protrudes into a left ventricle when the prosthetic valve is implanted in a native mitral valve. Annular valve body 2020 may include a valve inlet radius 2520, which may be the radius of atrial inlet opening 2032.

Figure 2E:
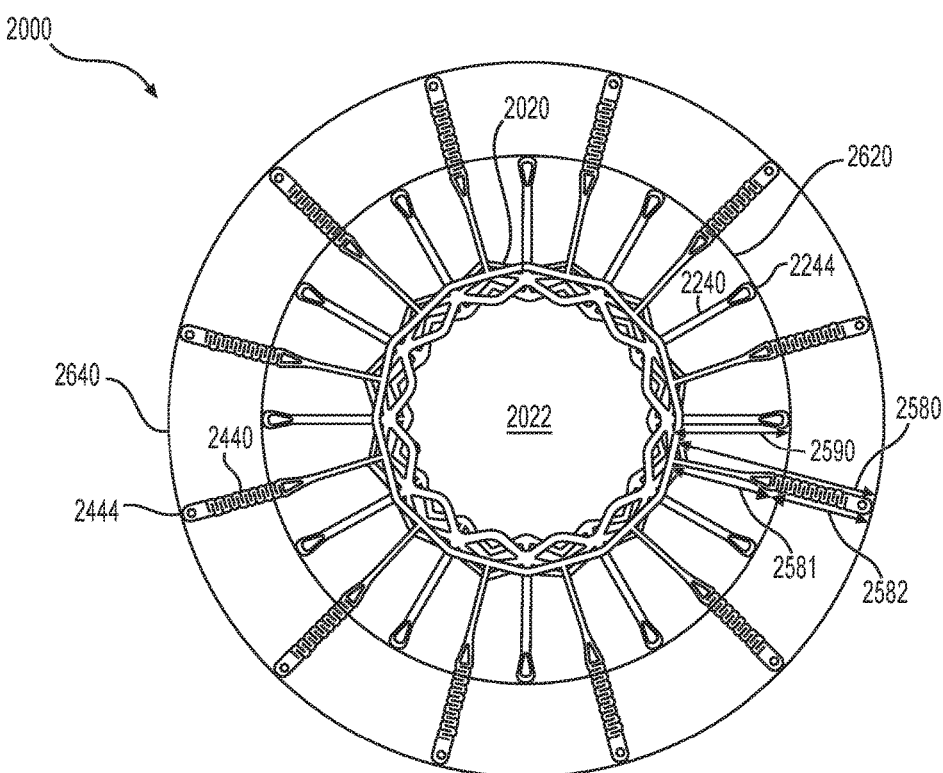
FIG. 2E illustrates another top plan view of the exemplary frame of FIG. 2A, consistent with various embodiments of the present disclosure.

FIG. 2E illustrates another top plan view of frame 2000. The atrial anchoring arms 2440 may have a length 2580, and the ventricular anchoring legs 2240 may have a length 2590. The terminal arm ends 2444 may define an atrial anchoring arm circumference 2640. The terminal leg ends 2244 may define a ventricular anchoring leg circumference 2620, which may be concentric with atrial anchoring arm circumference 2640. Inflexible portions 3402 of the atrial anchoring arms (illustrated in FIG. 3B) may have a length 2581. Serpentine structures 3406 of the atrial anchoring arms (illustrated in FIG. 3B) may have a length 2582.

Figure 3A:
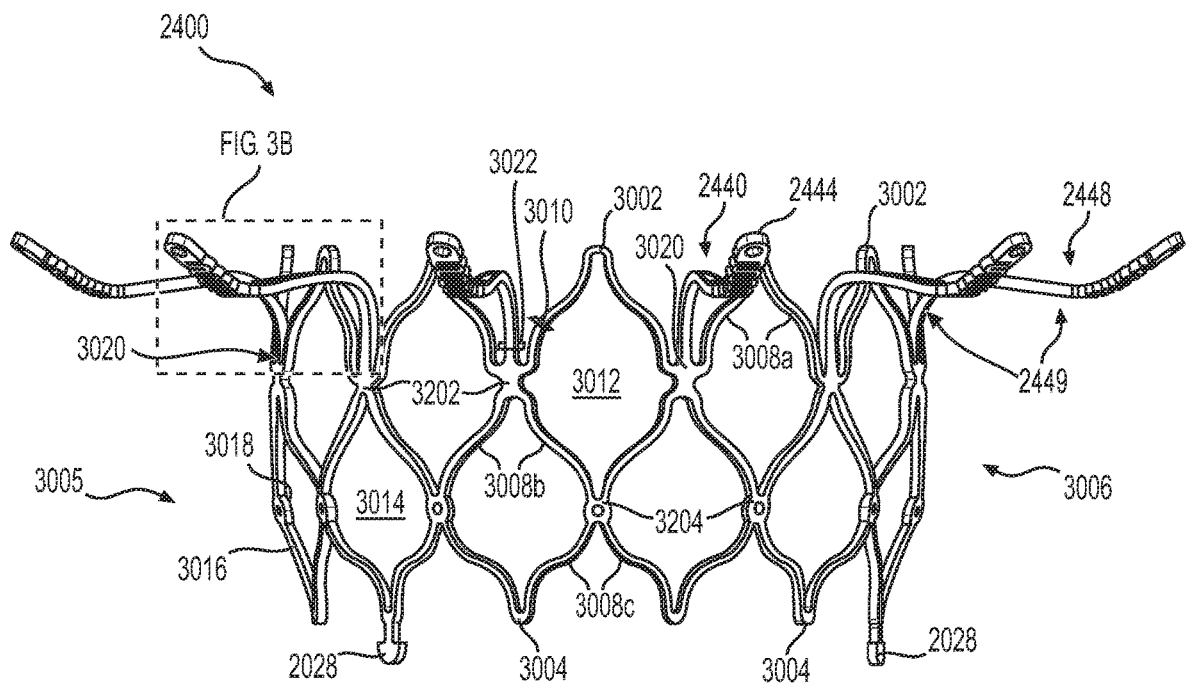
FIG. 3A illustrates a front elevation view of an inner frame of the exemplary frame of FIG. 2A, consistent with various embodiments of the present disclosure.

FIG. 3A illustrates a front elevation view of inner frame 2400. The atrial end inner frame junctions 3002 and ventricular end inner frame junctions 3004 may form the atrial end and ventricular end, respectively, of inner frame 2400. Inner frame intermediate portion 3006 may extend between atrial end inner frame junctions 3002 and ventricular end inner frame junctions 3004. Inner frame tubular portion 3005 may have a radially inner surface 3018 and a radially outer surface 3016. Inner frame atrial struts 3008a and inner frame intermediate struts 3008b may intersect at atrial end inner frame junctions 3002, arm attachment junctions 3202, and strut junctions 3204 to form a first, atrial row of closed cells 3012. Inner frame intermediate struts 3008b and inner frame ventricular struts 3008c may intersect at arm attachment junctions 3202, strut junctions 3204, and ventricular end inner frame junctions 3004 to form a second, ventricular row of closed cells 3014. At least one inner frame atrial strut 3008a may have a cross-sectional area 3010. At least one atrial anchoring arm 2440 may have a cross-sectional area 3022.

Figure 3B:
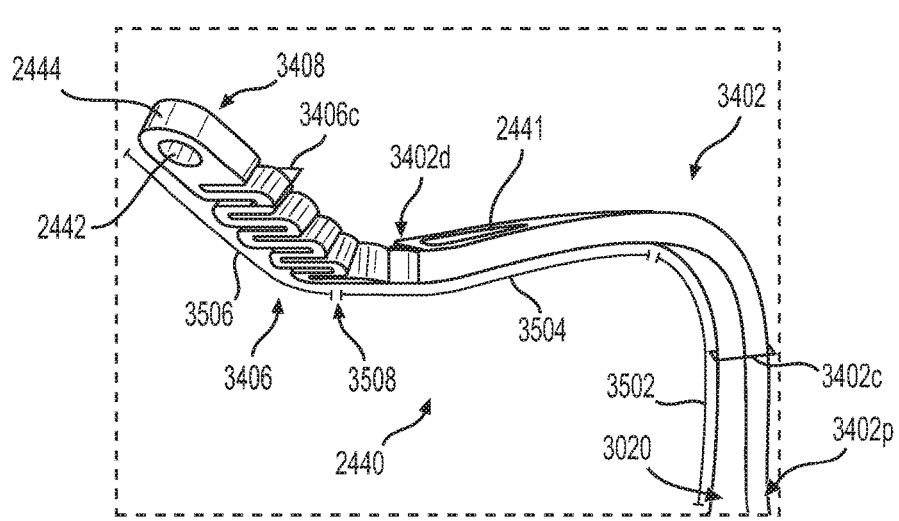
FIG. 3B illustrates an enlarged view of an atrial anchoring arm of the exemplary inner frame of FIG. 3A, consistent with various embodiments of the present disclosure.

FIG. 3B illustrates an enlarged view of an atrial anchoring arm 2440 of inner frame 2400. Atrial anchoring arm 2440 may include a proximal arm portion 3502 configured to extend in an atrial direction, intermediate arm portion 3504 configured to extend in a ventricular direction, and distal arm portion 3506 configured to extend in an atrial direction. Arm transition portion 3508 may represent the transition between intermediate arm portion 3504 and distal arm portion 3506. Atrial anchoring arm 2440 may also include an inflexible portion 3402 extending to proximal arm end 3020, as well as a serpentine structure 3406, which may be situated radially external to the inflexible portion 3402. Inflexible portion 3402 may have a proximal end 3402p, a distal end 3402d, and a cross-sectional area 3402c. Serpentine structure 3406 may have a cross-sectional area 3406c. In some embodiments, atrial anchoring arm 2440 may include a terminal arm region 3408 situated radially external to serpentine structure 3406. Distal arm opening 2442 may be situated within terminal arm region 3408.

Figure 3C:
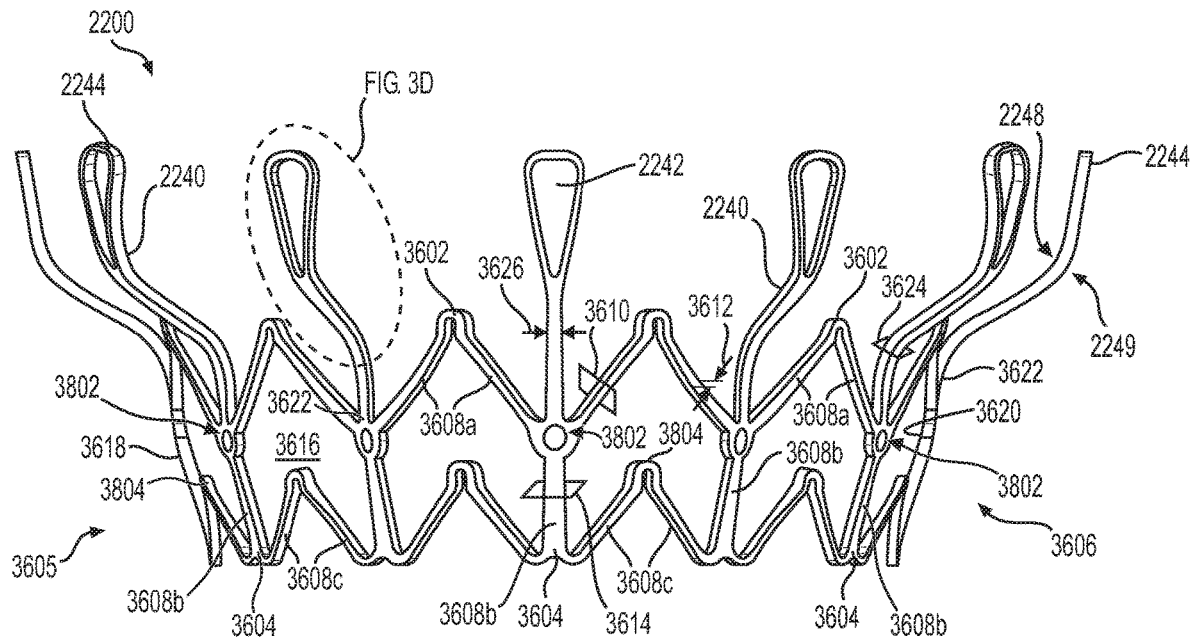
FIG. 3C illustrates a front elevation view of an outer frame of the exemplary frame of FIG. 2A, consistent with various embodiments of the present disclosure.

FIG. 3C illustrates a front elevation view of outer frame 2200. The atrial end outer frame junctions 3602 and ventricular end outer frame junctions 3604 may form the atrial end and ventricular end, respectively, of annular outer frame 2200. Outer frame intermediate portion 3606 may extend between atrial end outer frame junctions 3602 and ventricular end outer frame junctions 3604. Outer frame tubular portion 3605 may have a radially outer surface 3618 and a radially inner surface 3620. The outer frame atrial circumferential struts 3608a, outer frame leg base struts 3608b, and outer frame ventricular circumferential struts 3608c may intersect at the atrial end outer frame junctions 3602, leg attachment junctions 3802, outer frame junctions 3804, and ventricular end outer frame junctions 3604 to form closed cells 3616. At least one outer frame atrial circumferential strut 3608a may have a cross-sectional area 3610 and a width 3612. At least one outer frame leg base strut 3608b may have a cross-sectional area 3614. At least one ventricular anchoring leg may have a cross-sectional area 3624 and a radially outer surface width 3626.

Figure 3D:
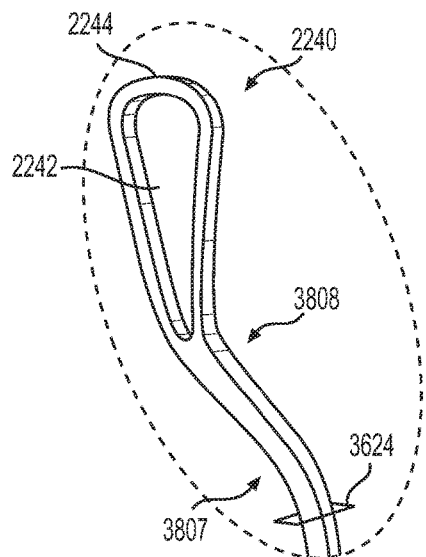
FIG. 3D illustrates an enlarged view of a ventricular anchoring leg of the exemplary outer frame of FIG. 3C, consistent with various embodiments of the present disclosure.

FIG. 3D illustrates an enlarged view of a portion of a ventricular anchoring leg 2240 of annular outer frame 2200. Ventricular anchoring leg 2240 may include a first, proximal curved portion 3807 and a second, distal curved portion 3808. In some embodiments, proximal curved portion 3807 may face radially outward. Additionally, or alternatively, distal curved portion 3808 may face radially inwards.

FIG. 4A illustrates a cross-sectional view of frame 2000, and FIG. 4B illustrates an enlarged view of a portion of FIG. 4A depicting a volume 4000 formed between the atrial anchoring arms 2440 and ventricular anchoring legs 2240. FIG. 4B also depicts an outer surface 4010 and inner surface 4020 of annular valve body 2020. In some embodiments, volume 4000 may be bounded by the ventricularly-facing surfaces 2449 of atrial anchoring arms 2440, by the inner, atrially-facing surfaces 2248 of ventricular anchoring legs 2240, and by the outer surface 4010 of the annular valve body 2020.

FIG. 5A illustrates a configuration of the exemplary prosthetic valve in which annular valve body 2020, atrial anchoring arms 2440, and ventricular anchoring legs 2240 are arranged in a radially-contracted configuration. In some embodiments, the configuration illustrated in FIG. 5A may constitute a radially-contracted configuration of the prosthetic valve.

FIG. 5B illustrates a configuration of the exemplary prosthetic valve in which annular valve body 2020 and atrial anchoring arms 2440 are arranged in a radially-contracted configuration. In the configuration of FIG. 5B, the ventricular anchoring legs 2240 may deflect radially outward away from annular valve body 2020, into a radially-expanded configuration of the ventricular anchoring legs 2240.

FIG. 5C illustrates a configuration of the exemplary prosthetic valve in which annular valve body 2020 and ventricular anchoring legs 2240 are arranged in a radially-contracted configuration. In the configuration of FIG. 5C, the atrial anchoring arms 2440 may deflect radially outward away from annular valve body 2020, into a radially-expanded configuration of the atrial anchoring arms 2440.

Figures 5D, 5E:
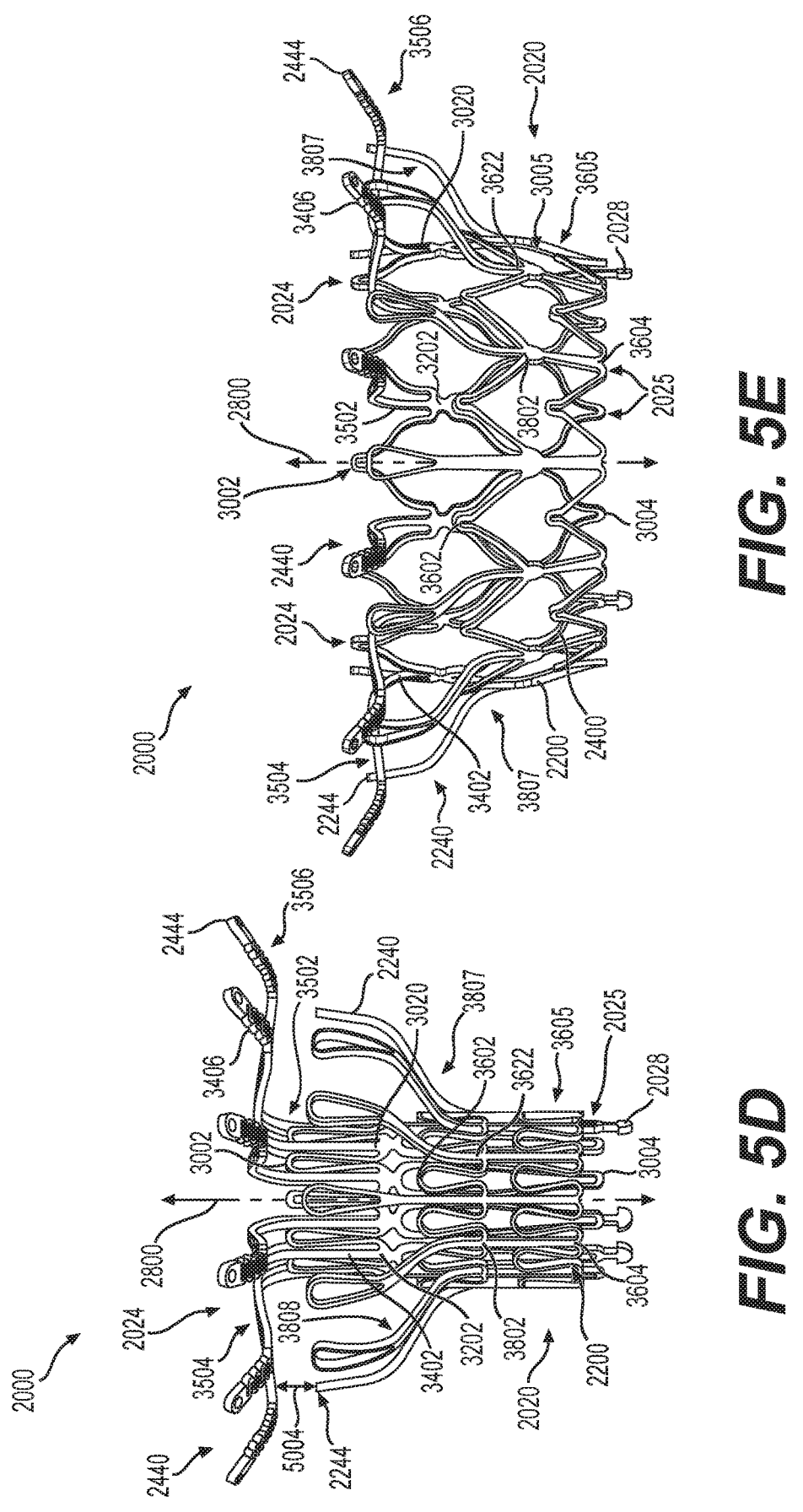

FIG. 5D illustrates a configuration of the exemplary prosthetic valve in which the atrial anchoring arms 2440 and ventricular anchoring legs 2240 may deflect radially outward away from annular valve body 2020 into their respective radially-expanded configurations, while annular valve body 2020 remains in a radially-contracted configuration. In the configuration of FIG. 5D, an axial distance 5004 may be formed between the atrial anchoring arms 2440 and the terminal ends 2244 of the ventricular anchoring legs 2240.

FIG. 5E illustrates a configuration of the exemplary prosthetic valve in which annular valve body 2020, atrial anchoring arms 2440, and ventricular anchoring legs 2240 are arranged in a radially-expanded configuration. In some embodiments, the configuration illustrated in FIG. 5E may constitute a radially-expanded configuration of the prosthetic valve.

Figure 6A:
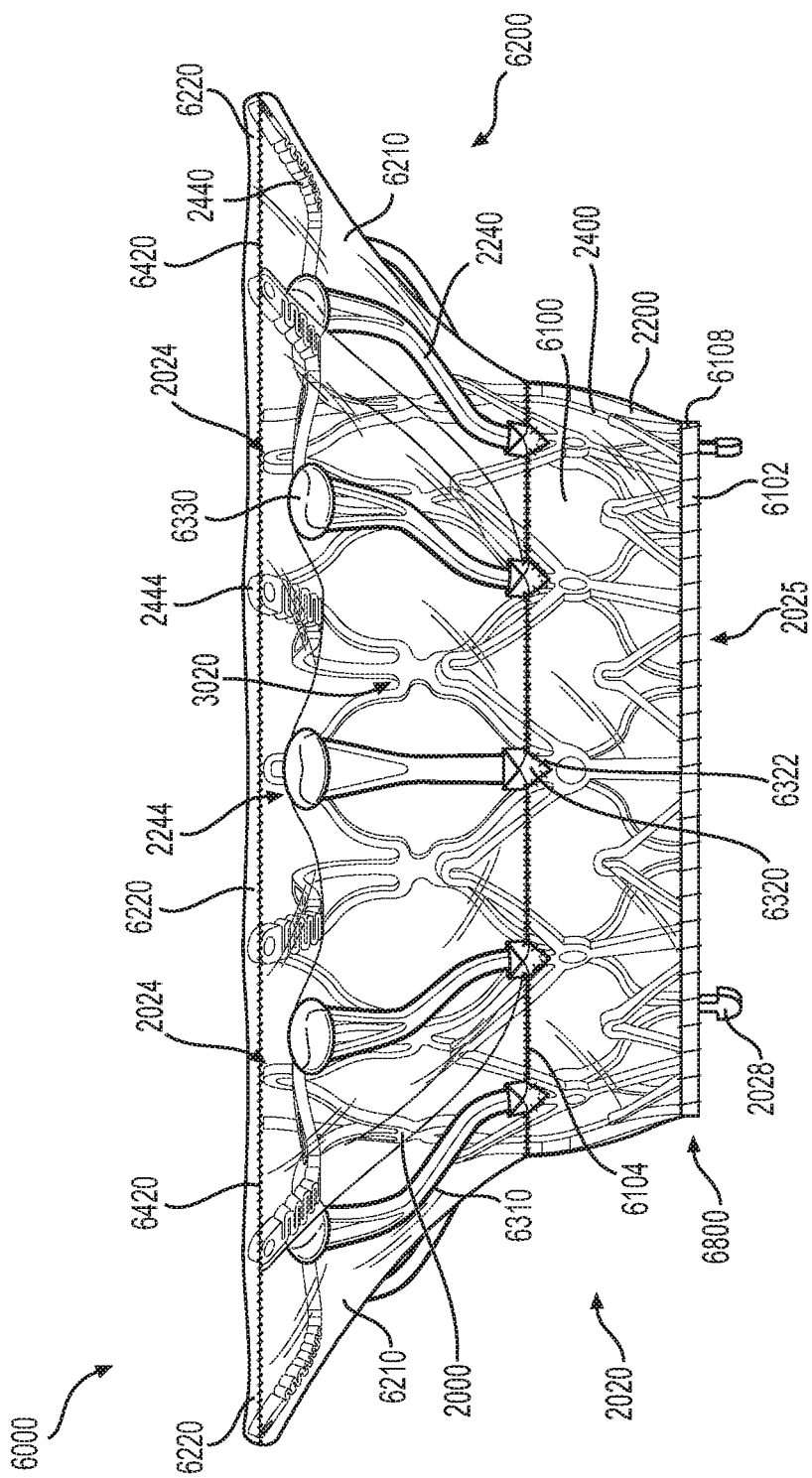
FIG. 6A illustrates a front elevation view of an exemplary prosthetic valve, consistent with various embodiments of the present disclosure.

FIG. 6A illustrates a front elevation view of prosthetic valve 6000. In some embodiments, prosthetic valve 6000 may be assembled upon frame 2000. Prosthetic valve 6000 may be configured for implantation within or near a native valve structure and may be configured to restore and/or replace the functionality of a native valve, such as a diseased or otherwise impaired native valve. Prosthetic valve 6000 may include valve frame 2000, including annular valve body 2020, the atrial anchoring arms 2440, and the ventricular anchoring legs 2240. Prosthetic valve 6000 may also include a skirt layer 6100 configured around an external surface of a portion of the annular valve body. Prosthetic valve 6000 may additionally include a first cuff sheet 6210, which may be connected to skirt layer 6100 via stitching 6104, as well as a second cuff sheet 6220, which may be connected to first cuff sheet 6210 via stitching 6420. In some embodiments, the first cuff sheet 6210 and second cuff sheet 6220 by extend around the terminal ends 2444 of the atrial anchoring arms 2440. Skirt layer 6100, first cuff sheet 6210, and second cuff sheet 6220 may be constructed of fluid-impermeable material and may accordingly be configured to prevent passage of blood or other fluids through portions of the prosthetic valve 6000 outside of the axial lumen 2022.

In some embodiments, prosthetic valve 6000 may additionally include a protective sleeve 6102 wrapped around the rim 6800 of the ventricular outlet opening of annular valve body 2020; protective sleeve 6102 may be secured to annular valve body 2020 by stitching 6108. Additionally, or alternatively, prosthetic valve 6000 may include at least one liner 6310 extending around an external surface of the ventricular anchoring legs 2240, with at least one protective layer 6330 positioned around the distal leg ends 2244 and at least one protective covering 6320 wrapped around the proximal leg ends 3622. In some embodiments, the at least one protective covering 6320 may be secured to the skirt layer 6100 via stitching 6322.

Figure 6B:
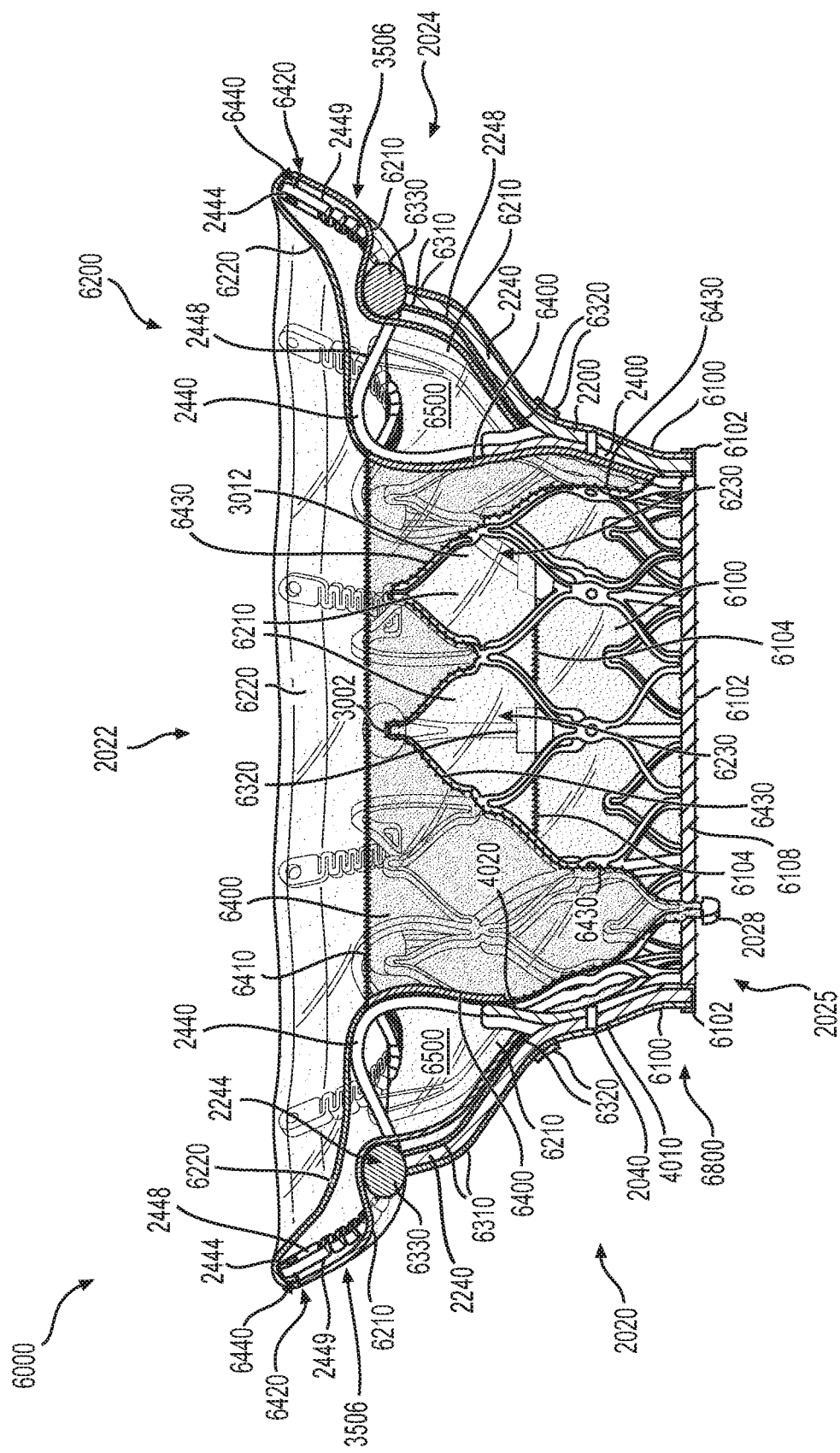
FIG. 6B illustrates a cross-sectional view of the exemplary prosthetic valve of FIG. 6A without leaflets, consistent with various embodiments of the present disclosure.

FIG. 6B illustrates a cross-sectional view of prosthetic valve 6000, without prosthetic leaflets situated within the axial lumen 2022. As illustrated in FIG. 6B, prosthetic valve 6000 may additionally include a liner 6400 covering at least a portion of the inner surface 4020 of the annular valve body 2020. Liner 6400 may be secured to the annular valve body 2020 via stitching 6430 and to the second cuff sheet 6220 via stitching 6410. First cuff sheet 6210, second cuff sheet 6220, and inner liner 6400 may together form an inflatable cuff 6200 having an interior volume 6500. In some embodiments, inflatable cuff 6200 may be secured to atrial anchoring arm 2440 via connector 6440. Blood may enter the cuff 6200 through openings 6230, causing the cuff 6200 to inflate radially outwards and axially in an atrial direction. In some embodiments, cuff 6200 may inflate radially outwards and press against tissue of the native valve. This engagement between the cuff and tissue of the native valve may form a barrier to flow of blood and other fluids around the outer circumference of the prosthetic valve 6000.

Figure 6C:
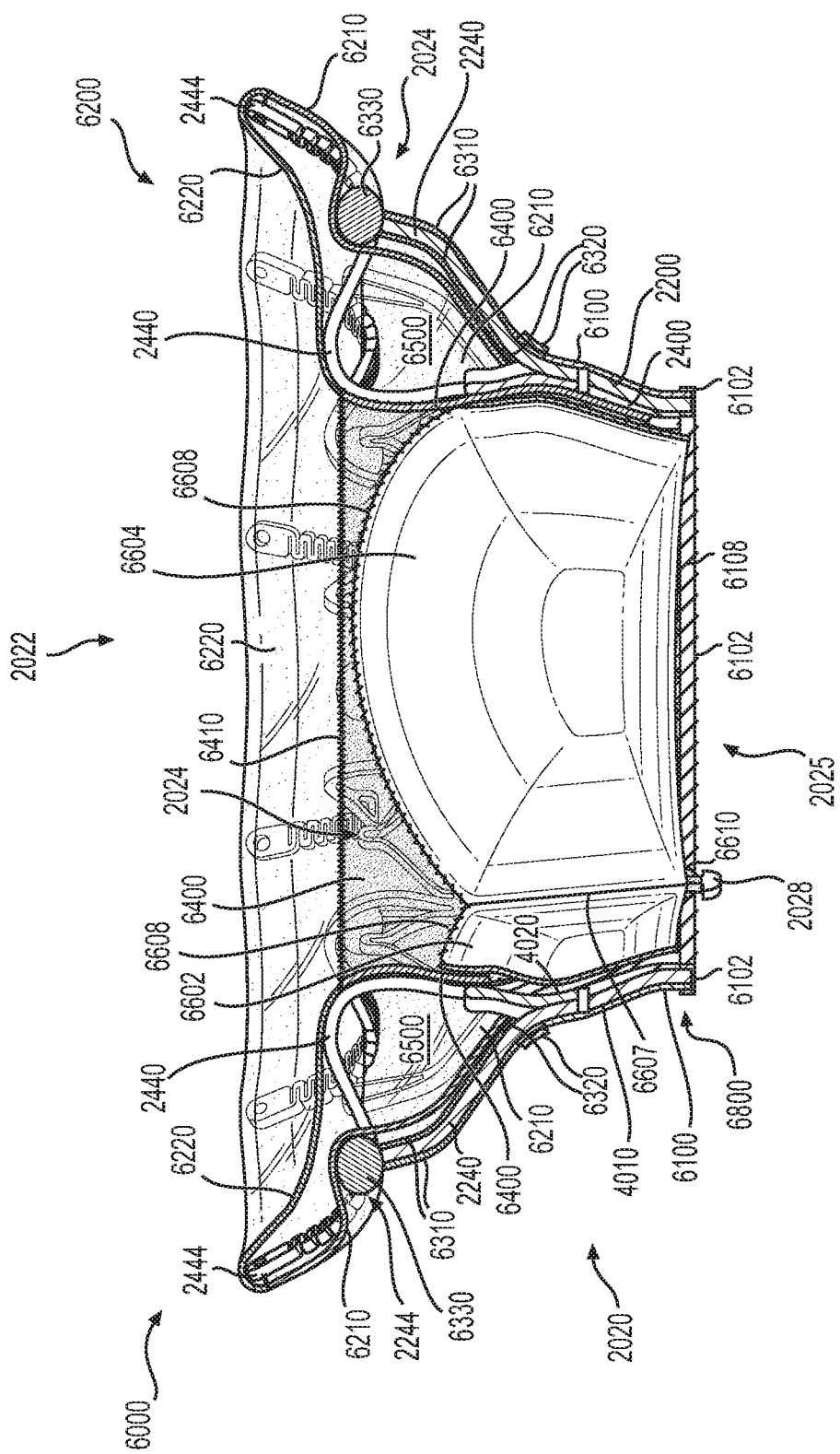
FIG. 6C illustrates a cross-sectional view of the exemplary prosthetic valve of FIG. 6A with leaflets, consistent with various embodiments of the present disclosure.

FIG. 6C illustrates a cross-sectional view of prosthetic valve 6000 with prosthetic leaflets 6602 and 6604 situated within the axial lumen 2022. In some embodiments, prosthetic valve 6000 may also include a third prosthetic leaflet 6606, which may not be visible in the view of FIG. 6C. The leaflets 6602, 6604, and 6606 may be secured to inner liner 6400 via stitching 6608 and may include a connector 6610 wrapping around the ventricular end delivery posts 2028 to secure the leaflets 6602, 6604, and 6606 to the valve frame 2000.

Figure 6D:
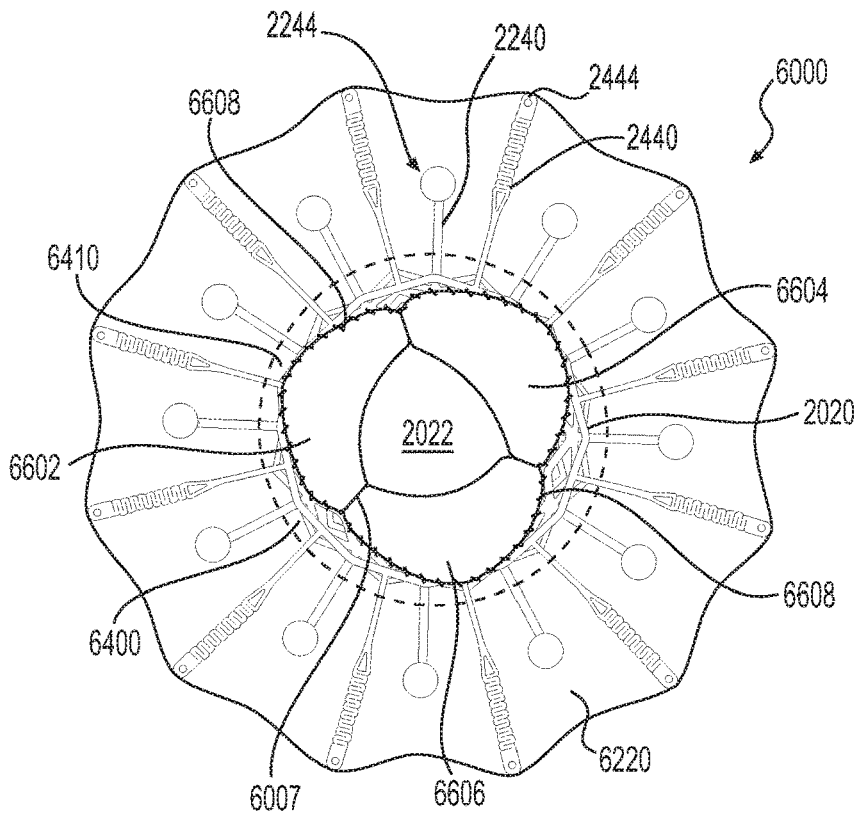
FIG. 6D illustrates a top plan view of the exemplary prosthetic valve of FIG. 6A with uninflated leaflets, consistent with various embodiments of the present disclosure.
Figure 6E:
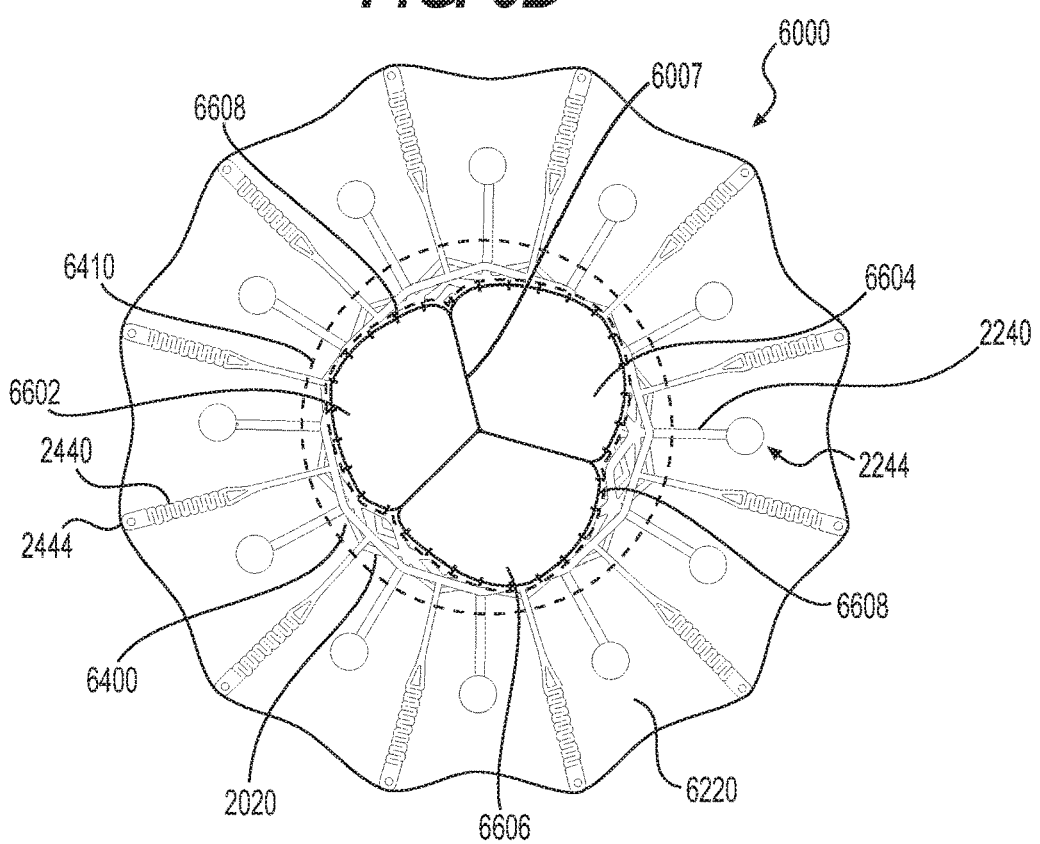
FIG. 6E illustrates a top plan view of the exemplary prosthetic valve of FIG. 6A with inflated leaflets, consistent with various embodiments of the present disclosure.

FIG. 6D illustrates a top plan view of prosthetic valve 6000, with leaflets 6602, 6604, and 6606 arranged in an open, uninflated configuration. In the open configuration, a space may be formed in the middle of the leaflets, permitting fluid to pass through the axial lumen 2022 of the prosthetic valve 6000. FIG. 6E illustrates a top plan view of prosthetic valve 6000, with leaflets 6602, 6604, and 6606 arranged in a closed, coapted configuration. In the closed configuration, the leaflets may press together such that the opening between them is closed. For example, the point of contact 6007 between two adjacent leaflets may extend to the center of the axial lumen; as a result, the leaflets may block fluid passage through the axial lumen 2022 of the prosthetic valve 6000.

Figure 7A:
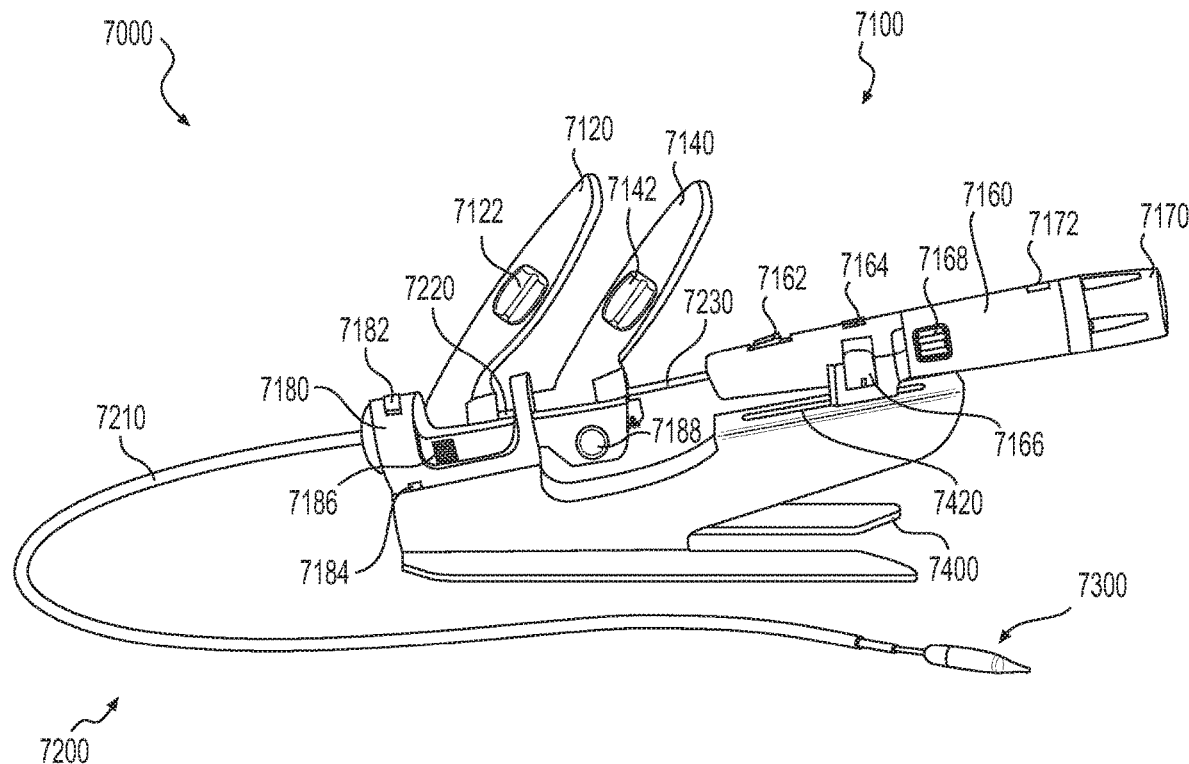
FIG. 7A illustrates an exemplary prosthetic valve delivery system, consistent with various embodiments of the present disclosure.

FIG. 7A illustrates a prosthetic valve delivery system 7000. Delivery system 7000 may be configured to deliver an implant prosthetic valve 6000 within a native valve, such as a native mitral valve. Prosthetic valve delivery system 7000 may include a control handle assembly 7100, a telescoping catheter assembly 7200, a delivery capsule 7300 configured to retain a prosthetic valve (e.g. valve 6000), and, optionally, a stand 7400.

Control handle assembly 7100 may include an outer sheath control handle 7120 having a steering knob 7122 configured to steer an outer sheath 7210 of the telescoping catheter assembly 7200. Control handle assembly 7100 may also include a guide catheter control handle 7140 having a steering knob 7142 configured to steer a guide catheter 7220 of the telescoping catheter assembly 7200.

Control handle assembly 7100 may also include an implant catheter control handle 7160 having a steering knob 7168 configured to steer an implant catheter 8100 of the telescoping catheter assembly 7200. Implant catheter control handle 7160 may also include a proximal capsule portion slider 7162, a distal capsule portion knob 7170, and a distal capsule portion knob lock 7172 configured to control release of the prosthetic valve 6000 from within delivery capsule 7300. Implant catheter control handle 7160 may also include a slide lock 7166 configured to lock the implant catheter control handle 7160 at a position within track 7420 of stand 7400.

Control handle assembly 7100 may also include a cradle 7180, which may be secured to stand 7400 via a locking mechanism that can be released by actuated of release button 7184. Cradle 7180 may include a rotation knob 7182 configured to control rotation of the outer sheath 7210 and guide catheter 7220. Cradle 7180 may also include a rotation knob 7186 configured to control rotation of the implant catheter 8100. Cradle 7180 may also include a knob 7188 configured to control relative axial movement between outer sheath control handle 7120 (which may be secured to outer sheath 7210) and guide catheter control handle 7140 (which may be secured to guide catheter 7220).

Figure 7B:
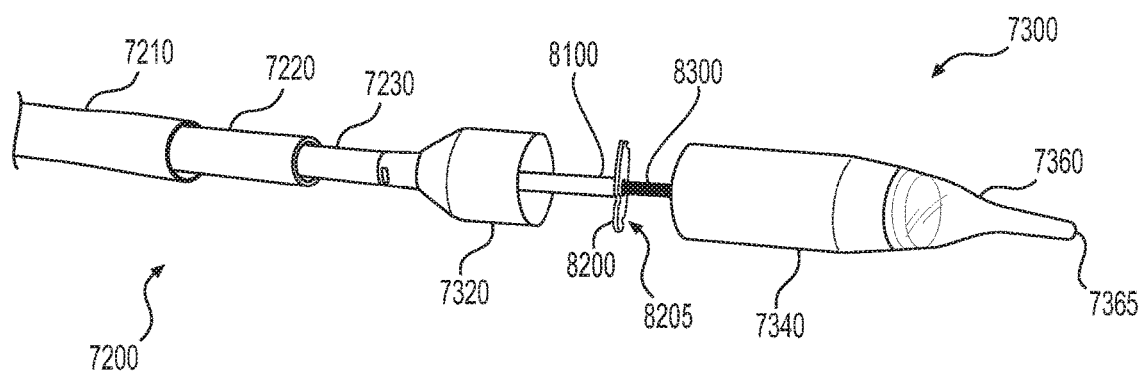
FIG. 7B illustrates an enlarged view of a delivery capsule of the exemplary prosthetic valve delivery system of FIG. 7A, consistent with various embodiments of the present disclosure.

FIG. 7B illustrates an enlarged view of delivery capsule 7300 of prosthetic valve delivery system 7000. Delivery capsule 7300 may include a proximal capsule portion 7320 and a distal capsule portion 7340 with a nose cone 7360 secured to the distal capsule portion 7340. A nose cone distal tip 7365 may form the distal end of the delivery capsule 7300. The telescoping catheter assembly 7200 may include a capsule shaft 7230 secured to, and configured to control movement of, the proximal capsule portion 7320 (e.g., due to connection 8400 between the capsule shaft 7230 and proximal capsule portion 7320, as illustrated in FIG. 8C). Implant catheter 8100 may extend within proximal capsule portion 7320 and may have a valve anchor disc 8200 connected to the distal end of the implant catheter 8100. A torque shaft 8300 may extend from the implant catheter 8100 and may be connected to distal capsule portion 7340; accordingly, torque shaft 8300 may be configured to control axial movement of the distal capsule portion 7340 relative to the implant catheter 8100 and valve anchor disc 8200. The proximal capsule portion 7320 and a distal capsule portion 7340 may be configured to retain prosthetic valve 6000, with the prosthetic valve 6000 secured against axial movement by valve anchor disc 8200. Control handle assembly 7100 may be configured to control movement of the proximal capsule portion 7320 and a distal capsule portion 7340, and thus may also control release of the prosthetic valve 6000 from within the delivery capsule 7300.

FIGS. 7C and 7D illustrate exemplary configurations of the telescoping catheter assembly 7200. Outer sheath 7210 and guide catheter 7220 may include respective bending portions 7215 and 7225, at which the outer sheath 7210 and guide catheter 7220 may be configured to bend within their respective steering planes 7212 and 7222. In some embodiments, bending of the outer sheath 7210 within the first steering plane 7212 may be controlled by the outer sheath steering knob 7122 of the control handle assembly 7100. Additionally, or alternatively, bending of the guide catheter 7220 within the second steering plane 7222 may be controlled by the guide catheter steering knob 7142 of the control handle assembly 7100. In some embodiments, under control of the control handle assembly 7100, the outer sheath 7210, guide catheter 7220, and implant catheter 8100 may be steered so as to correctly position the delivery capsule 7300 within a native valve for implantation of the prosthetic valve.

Figure 8A:
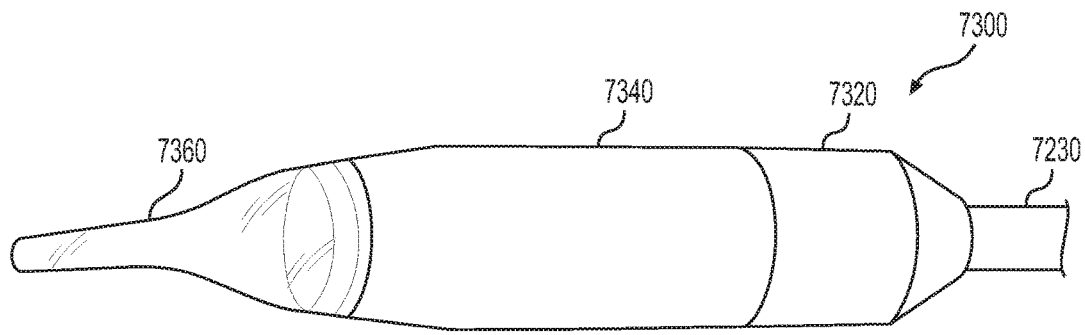
FIG. 8A illustrates another enlarged view of the exemplary delivery capsule of the prosthetic valve delivery system of FIG. 7A in a closed configuration, consistent with various embodiments of the present disclosure.
Figure 8B:
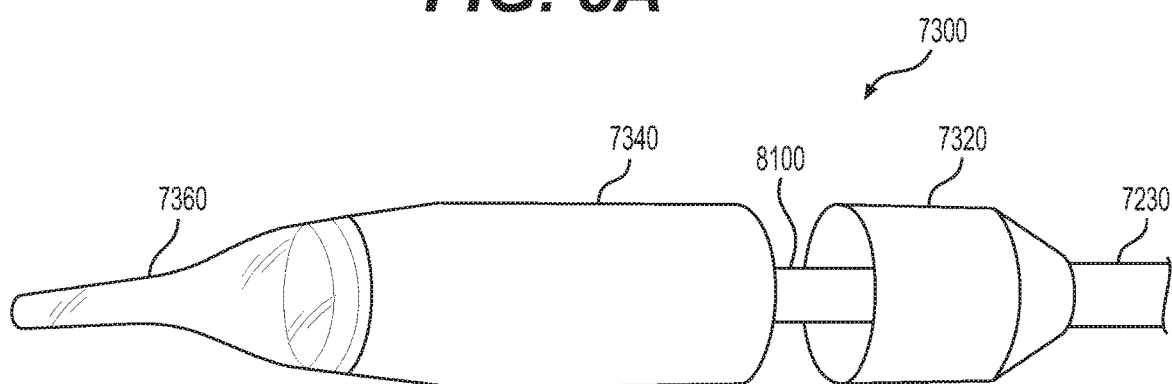
FIG. 8B illustrates the exemplary delivery capsule of FIG. 8A in an open configuration, consistent with various embodiments of the present disclosure.
Figure 8C:
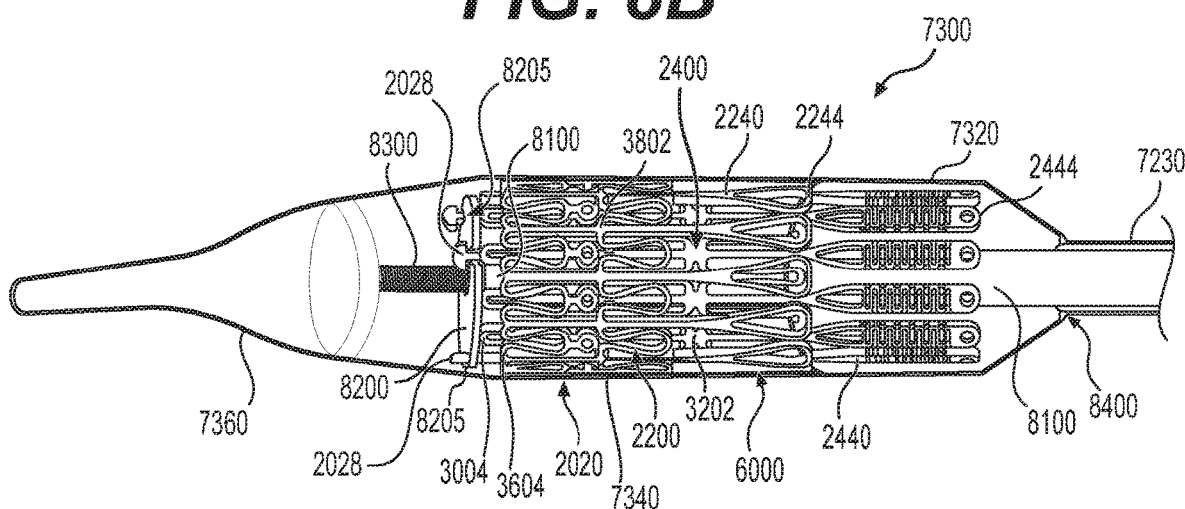
FIG. 8C illustrates an interior view of the exemplary delivery capsule of FIG. 8A in the closed configuration, consistent with various embodiments of the present disclosure.

FIG. 8A illustrates an enlarged view of delivery capsule 7300 in a closed configuration, while FIG. 8B illustrates an enlarged view of delivery capsule 7300 in an open configuration. In the closed configuration of FIG. 8A, the distal capsule portion 7340 and proximal capsule portion 7320 may be brought together to form an enclosed compartment in which prosthetic valve 6000 may be retained. In the open configuration of FIG. 8B, the distal capsule portion 7340 and proximal capsule portion 7320 may be drawn apart. In some embodiments, the delivery capsule 7300 may be configured such that the distal capsule portion 7340 and proximal capsule portion 7320 are moved apart from each other, the prosthetic valve 6000 may be sequentially deployed from within the delivery capsule and implanted within a native valve.

FIG. 8C illustrates an interior view of delivery capsule 7300 with prosthetic valve 6000 retained within the delivery capsule. Although only the valve frame 2000 of the prosthetic valve 6000 is illustrated in FIG. 8C, one of ordinary skill will understand that the entire prosthetic valve 6000 depicted in FIGS. 6A-6E may be retained within delivery capsule 7300 in the configuration illustrated in FIG. 8C.

In the embodiment illustrated in FIG. 8C, at least a portion of the annular valve body 2020 and ventricular anchoring legs 2240 of the prosthetic valve 6000 may be retained within the distal capsule portion. Additionally, or alternatively, at least a portion of atrial anchoring arms 2440 may be retained within proximal capsule portion 7320. In some embodiments, valve anchor disc 8200 may include a number of recesses 8205 configured to receive and retain the ventricular end delivery posts 2028 of the prosthetic valve 6000. For example, the valve anchor disc 8200 may include at least the same number of recesses 8205 as there are delivery posts 2028 of the prosthetic valve 6000. In some embodiments, the delivery posts 2028 may be retained within the recesses 8205 so long as the annular valve body 2020 remains in a radially-contracted configuration; the engagement between the valve anchor disc 8200 and delivery posts 2028 may secure the prosthetic valve 6000 against axial movement. Upon radial expansion of the annular valve body 2020, the delivery posts 2028 may slide or expand out of the recesses 8205, freeing the prosthetic valve 6000 from engagement with the valve anchor disc 8200.

Figure 9:
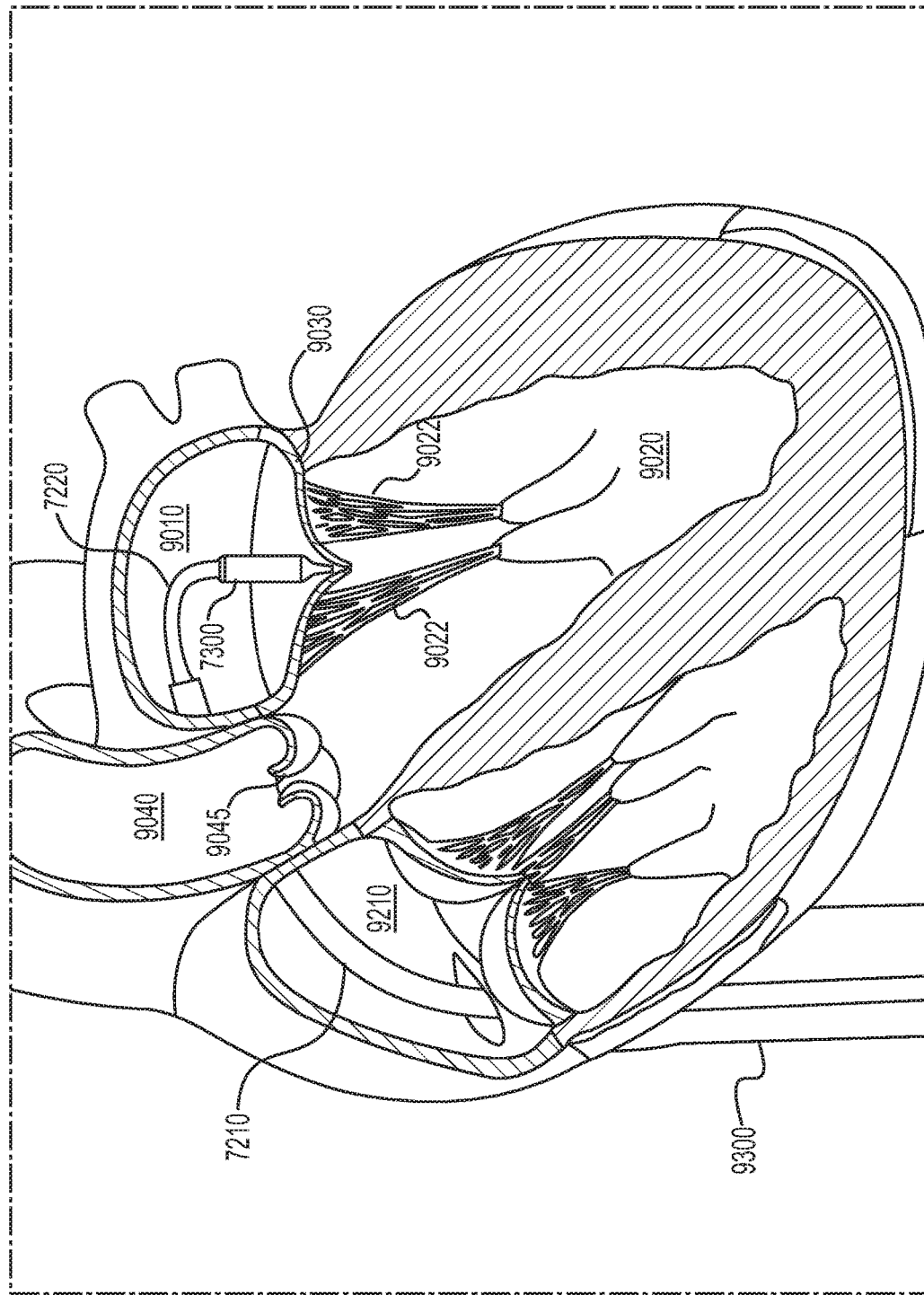
FIG. 9 illustrates advancement of the exemplary prosthetic valve delivery system of FIG. 7A into the left atrium, consistent with various embodiments of the present disclosure.

FIG. 9 illustrates one exemplary advancement route of the delivery capsule 7300 to the left atrium. In the example illustrated in FIG. 9, the delivery capsule 7300 may be steered through the vena cava into the right atrium 9210 and may pierce the interatrial septum and enter the left atrium 9010. Alternatively, the delivery capsule may be delivered to the heart by other routes. FIG. 9 also depicts the left ventricle 9020, the mitral valve 9030, the chordae tendineae 9022, the aortic valve 9045, and the aorta 9040.

Figure 10B:
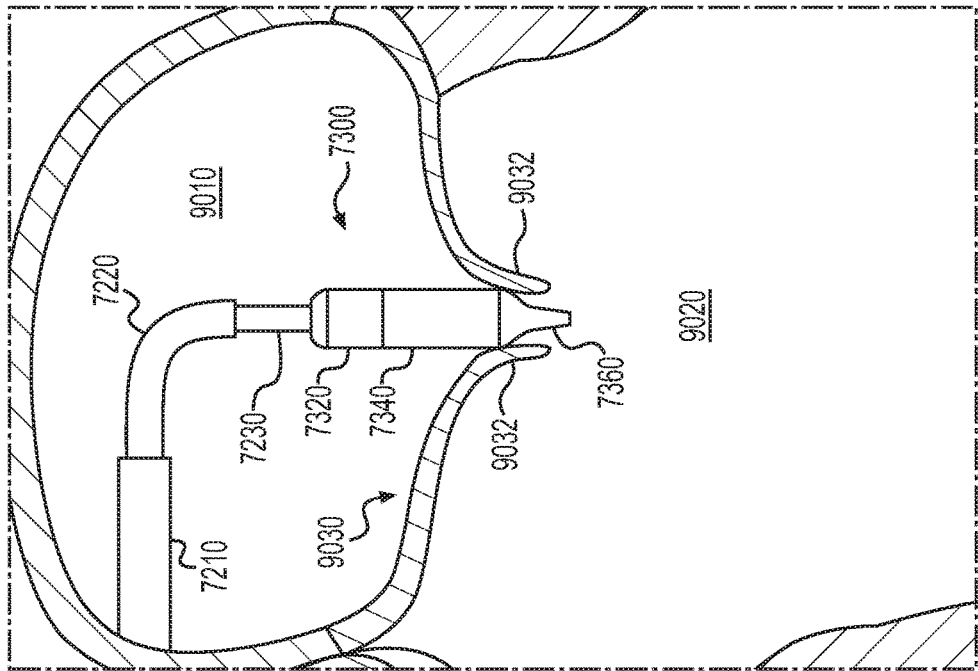
FIGS. 10A-10H depict implantation of the prosthetic valve of FIGS. 6A-6E within a native mitral valve by the exemplary prosthetic valve delivery system of FIG. 7A, consistent with various embodiments of the present disclosure.
Figure 10A:
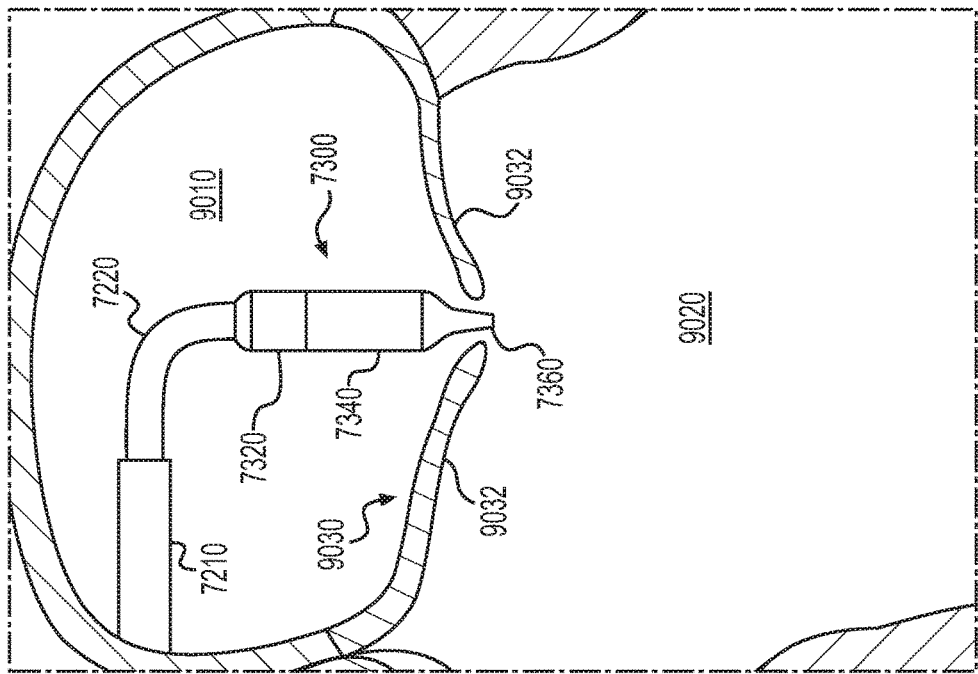
Figure 10D:
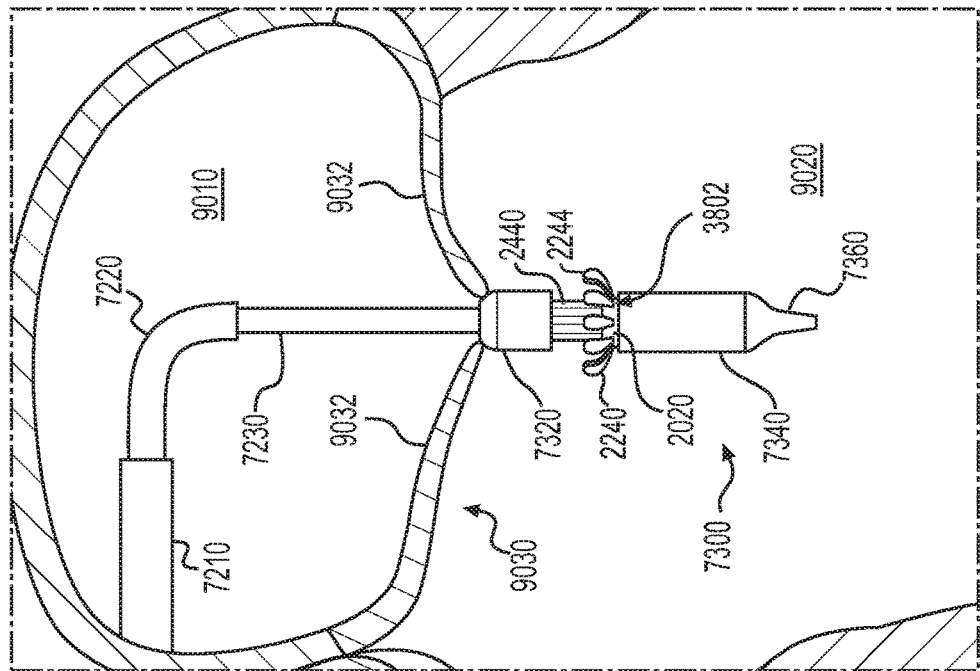
Figure 10C:
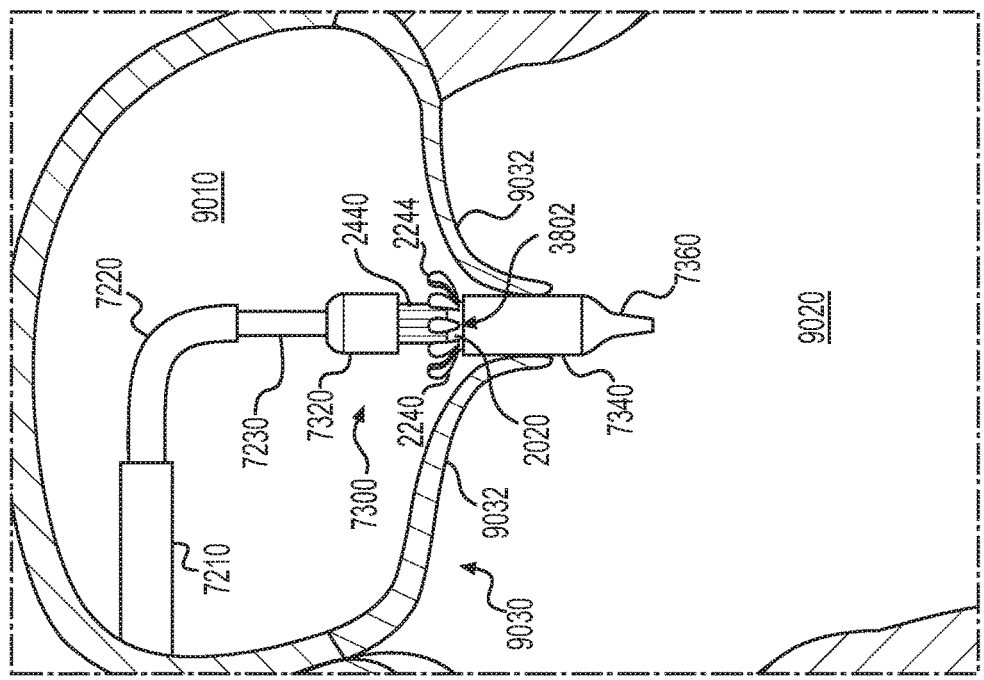

FIGS. 10A-10H depict an exemplary implantation method of prosthetic valve 6000 within a mitral valve 9030. In FIG. 10A, the delivery capsule 7300 may be coaxially aligned with the mitral valve 9030. In some embodiments, the prosthetic valve 6000 may be held within the delivery capsule 7300 while the prosthetic valve is arranged in the configuration of FIG. 5A. In FIG. 10B, the delivery capsule 7300 may be distally advanced into the mitral valve 9030. In FIG. 10C, the distal capsule portion 7340 may be distally advanced relative to the rest of the delivery capsule 7300. This may release the ventricular anchoring legs 2240 from the distal capsule portion 7340, while the atrial anchoring arms 2440 and annular valve body 2020 remain constrained within the delivery capsule. In the example shown in FIG. 10C, the ventricular anchoring legs 2240 may be released from the delivery capsule 7300 within the atrium 9010. In some embodiments, the prosthetic valve 6000 may assume the configuration of FIG. 5B when the ventricular anchoring legs 2240 are released in the step depicted in FIG. 10C.

Figure 10F:
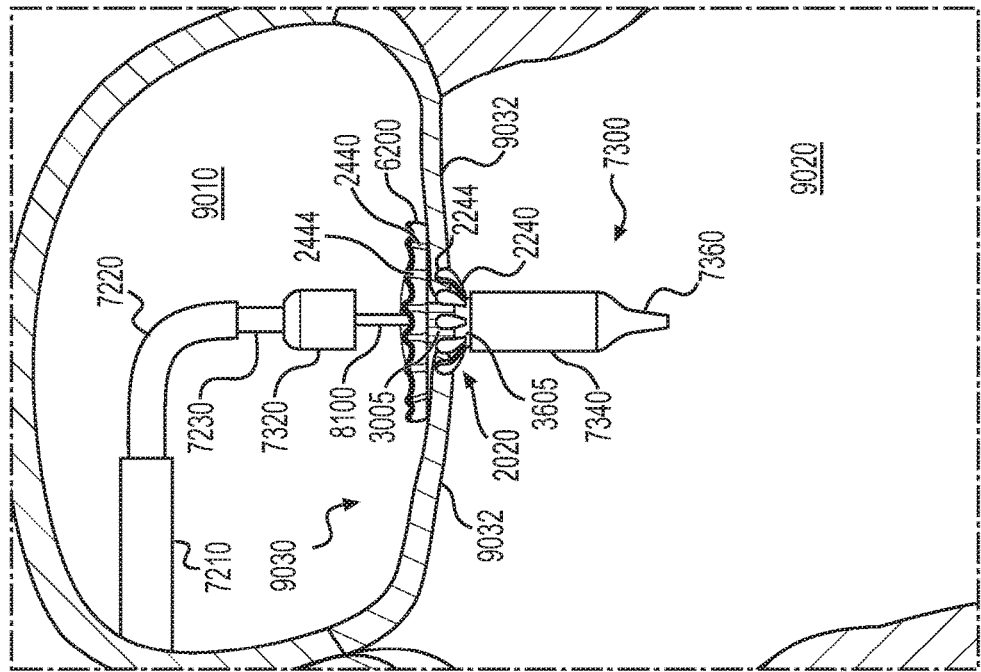
Figure 10E:
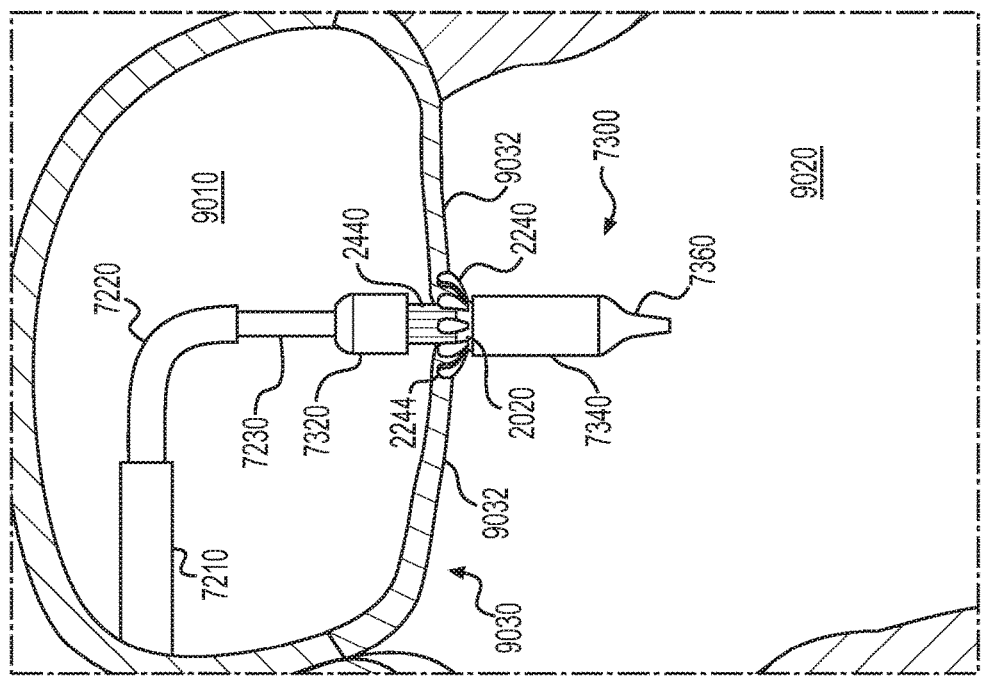

In FIG. 10D, the released ventricular anchoring legs 2240 may be passed through the mitral valve 9030 and into the left ventricle 9020. In FIG. 10E, the released legs 2240 may be proximally retracted until the ventricular anchoring legs come into contact with the ventricular tissue of the mitral valve 9030. In FIG. 10F, the proximal capsule portion 7320 may be retracted proximally, thus releasing the atrial anchoring arms 2440 within atrium 9010 while the annular valve body 2020 remains radially constrained within the distal capsule portion 7340. In some embodiments, the prosthetic valve 6000 may assume the configuration of FIG. 5D when the atrial anchoring arms 2440 are released in the step of FIG. 10F.

Figure 10G:
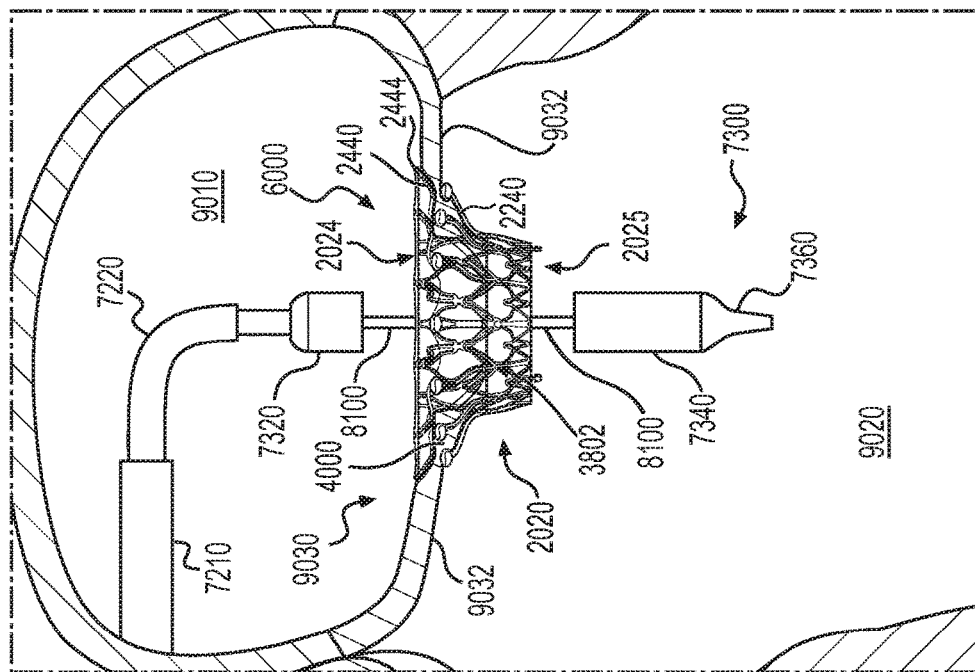

In FIG. 10G, the distal capsule portion 7340 may be advanced further until the annular valve body 2020 is released from the capsule and allowed to radially expand.

Figure 10H:
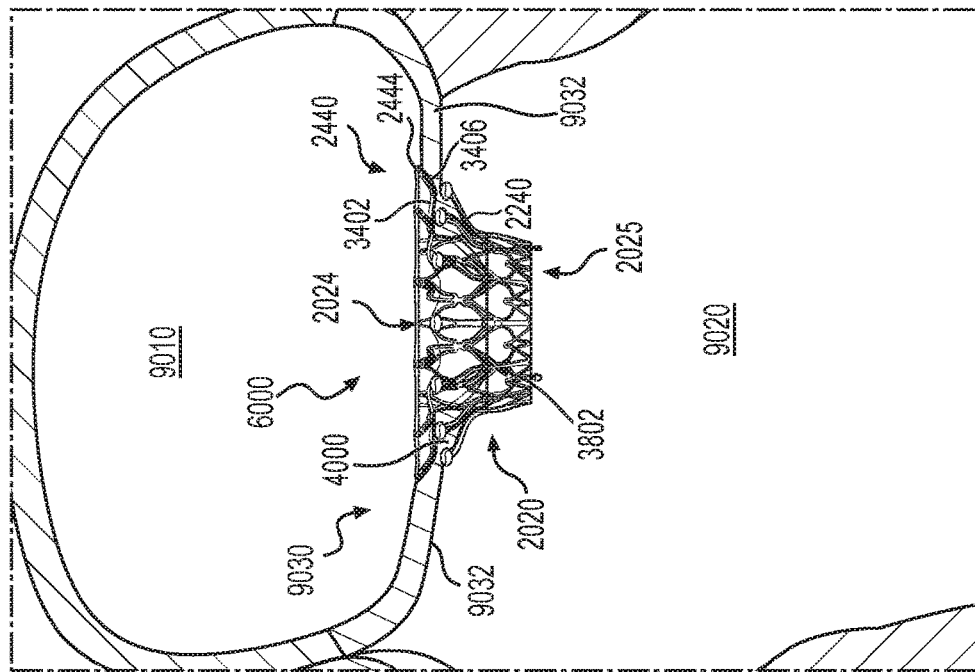

Radial expansion of the annular valve body 2020 may allow the prosthetic valve to assume the fully-expanded configuration illustrated in FIG. 5E. At this stage, prosthetic valve 6000 may be securely implanted within mitral valve 9030. In FIG. 10H, the delivery system 7000, including capsule 7300, may be removed.

Various embodiments of the present disclosure relate to prosthetic valves. Prosthetic heart valve 6000, illustrated in FIGS. 6A-6E, is one example of a prosthetic valve in accordance with the present disclosure. In some embodiments, an exemplary prosthetic valve may be configured for implantation within a native mitral valve. According to such embodiments, the prosthetic valve may be configured for implantation within or near the mitral valve orifice and may include a flow control mechanism (e.g., prosthetic leaflets) to regulate flow of blood between the left atrium and the left ventricle. For example, in FIGS. 10A-10H, exemplary prosthetic valve 6000 may be delivered to and expanded within native mitral valve 9030 such that prosthetic valve 6000 is anchored within native mitral valve 9030 and regulates blood flow between left atrium 9010 and left ventricle 9020. In some embodiments, an exemplary prosthetic valve may be configured to grasp tissue of a native valve into which it is implanted to more firmly anchor the prosthetic valve within the native valve. For example, exemplary prosthetic valves may be configured to grasp the native leaflets and/or native valve annulus to firmly seat the prosthetic valve within the valve annulus, thus preventing the prosthetic valve from migrating or dislodging from within the native valve annulus. For example, as depicted in FIGS. 10F-10H, exemplary prosthetic valve 6000 may be configured to grasp native leaflets 9032 and portions of the native valve annulus between atrial anchoring arms 2440 and ventricular anchoring legs 2240.

In some embodiments, an exemplary prosthetic valve may be configured for implantation within a native atrioventricular valve and may regulate blood flow between the atrium and ventricle. For example, prosthetic heart valve 6000 illustrated in FIGS. 6A-6C may include a fluid-impervious cuff 6200 configured to extend from an inner lumen 2022 of the prosthetic valve to terminal arm ends 2444 of a plurality of atrial anchoring arms 2440. Because cuff 6200 is constructed of a fluid-impervious material, cuff 6200 may be configured to minimize or block flow of blood and other fluids through any portion of the prosthetic valve 6000 except for lumen 2022. In addition, atrial anchoring arms 2440 of the prosthetic valve (including terminal arm ends 2444) may be configured to contact and, in some embodiments, press against atrial tissue of a native heart valve. This is illustrated in FIGS. 10G-10H, which depict atrial anchoring arms 2440 of prosthetic valve 6000 arranged in contact with, and exerting a ventricularly-directed force (that is, a force directed downwards toward ventricle 9020) upon atrial tissue of native mitral valve 9030. As a result, cuff 6200 of prosthetic valve 6000 may also be configured to minimize or block passage of blood and other fluids between the prosthetic valve 6000 (including terminal arm ends 2444) and native valve tissue, a condition known as perivalvular leakage. As a result, prosthetic valve 6000 may be configured to prohibit passage of blood and other fluids between atrium 9010 and ventricle 9020, except by passage through inner lumen 2022, in which leaflets 6602, 6604, and 6606 may be situated.

An exemplary prosthetic valve in accordance with the present disclosure may include an annular valve body. The term "annular" may mean "ring-shaped" and may denote a structure having at least one opening therein. The at least one opening may extend longitudinally along the entire length of the annular valve body. For example, annular valve body 2020 illustrated in FIG. 2B may include an axial lumen 2022 extending longitudinally through the valve body. The annular valve body may be sized and configured to be seated within the orifice of a native valve. For example, annular valve body 2020 depicted in FIG. 10H may be situated within the orifice of mitral valve 9030, specifically between native leaflets 9032.

In some embodiments, the annular valve body may be configured to have a smaller diameter, when fully-expanded, than the diameter of the orifice of the native valve. In such embodiments, the annular valve body may be anchored in the native valve by anchoring structures, such as atrial anchoring arms 2440 and/or ventricular anchoring legs 2240. Alternatively, the annular valve body may be configured to expand to an equal or greater diameter than the diameter of the native valve orifice such that the annular valve body is anchored within the native valve due to a pressure fit or friction fit with the native valve tissue. In such embodiments, the prosthetic valve may also include tissue anchors to further secure the prosthetic valve at the implantation site. In some embodiments, the annular valve body may be configured to receive and retain a flow control device, such as one or more leaflets, within the opening thereof. For example, the flow control device (e.g., leaflets) may be secured directly to the annular valve body and/or to an additional structure that is in turn secured to the annular valve body. For example, prosthetic heart valve 6000, illustrated in FIGS. 6D and 6E, may include three prosthetic leaflets 6602, 6604, and 6606, which may act as a flow control device to control the flow of blood between the atrial and ventricular chambers of the heart. When the exemplary prosthetic valve is implanted within a native valve (e.g., a mitral valve), the opening of the annular valve body may be the single fluid passage through the prosthetic valve; as a result, the flow control device may regulate fluid passage through the native valve upon implantation of the prosthetic valve.

The annular valve body may have a circular, oval-shaped, elliptical, or D-shaped cross-section and may be symmetrical about at least one axis. Alternatively, the annular valve body may have any suitable cross-sectional shape with at least one opening. In some embodiments, the annular valve body may be cylindrical, with a substantially constant diameter along the entire length. Alternatively, the annular valve body may have a variable diameter at different portions (e.g., at different longitudinal portions). For example, as illustrated in FIG. 2A, exemplary annular valve body 2020 may have a larger diameter at a longitudinally central portion thereof (e.g., the portion including connectors 2040 and a smaller diameter at an atrial end 2024 and a ventricular end 2025. Advantageously, such a configuration may improve the seating of the annular valve body within the native valve orifice, providing an improved pressure fit.

In some embodiments, the exemplary annular valve body may include a plurality of supporting members or struts. In some embodiments, the struts may intersect at junctions to form a wire mesh, stent-like, or cage-like structure of the annular valve body. In some embodiments, the struts of the annular valve body may be made of metals or alloys such as Nitinol. In some embodiments, the struts of the annular valve body may meet or intersect at junctions of the annular valve body. For example, as illustrated in FIG. 2A, the valve body 2020 can include inner frame atrial struts 3008a, inner frame intermediate struts 3008b, and inner frame ventricular struts 3008c, which may intersect at atrial end inner frame junctions 3002, arm attachment junctions 3202, inner frame junctions 3204, and ventricular end inner frame junctions 3004 of inner frame 2400. Additionally, or alternatively, valve body 2020 may include outer frame atrial circumferential struts 3608a, outer frame leg base struts 3608b, and outer frame ventricular circumferential struts 3608c, which may intersect at atrial end outer frame junctions 3602, leg attachment junctions 3802, outer frame junctions 3804, and ventricular end outer frame junctions 3604 of inner frame 2200. A junction may be formed at a location at which at least two struts terminate; that is, exemplary struts may extend to and terminate at a junction at which they intersect with one or more other struts. In some embodiments, the struts may intersect at junctions to form a lattice or overlapping pattern. In some embodiments, two struts, three struts, four struts, five struts, or any other suitable number of struts may intersect at junctions of the annular valve body. In some embodiments, the struts of the annular valve body may be arranged so as to form one or more frames of the exemplary prosthetic valve.

In some embodiments, the prosthetic valve may include a plurality (that is, one or more) of atrial anchoring arms. In some embodiments, the exemplary prosthetic valve may include two atrial anchoring arms, three atrial anchoring arms, four atrial anchoring arms, five atrial anchoring arms, six atrial anchoring arms, seven atrial anchoring arms, eight atrial anchoring arms, nine atrial anchoring arms, ten atrial anchoring arms, eleven atrial anchoring arms, twelve atrial anchoring arms, thirteen atrial anchoring arms, fourteen atrial anchoring arms, fifteen atrial anchoring arms, sixteen atrial anchoring arms, seventeen atrial anchoring arms, eighteen atrial anchoring arms, nineteen atrial anchoring arms, twenty atrial anchoring arms, or any other suitable number of atrial anchoring arms. For example, exemplary prosthetic valve 6000 in FIG. 2B may include twelve atrial anchoring arms 2440.

In some embodiments, the prosthetic valve may include a plurality of atrial anchoring arms configured to engage atrial tissue of the native mitral valve to anchor the prosthetic valve. In reference to the atrial anchoring arms, the term "proximal" refers to a portion of a respective atrial anchoring arm in closest proximity to the prosthetic valve and may, in some embodiments, include a point of connection between the atrial anchoring arm and the prosthetic valve. The term "distal" refers to a portion of the atrial anchoring arm furthest from the point of connection between the atrial anchoring arm and the prosthetic valve. In some embodiments, the atrial anchoring arms may be configured to extend radially outward from the prosthetic valve such that the distal arm ends may be the radially outer-most portions of the atrial anchoring arms, with reference to the longitudinal axis of the prosthetic valve. For example, in FIGS. 2A and 5E, which depict the frame 2000 of an exemplary prosthetic valve in a radially-expanded configuration, atrial anchoring arms 2440 may be secured to the prosthetic valve (specifically, to inner frame tubular portion 3005) at proximal arm ends 3020 and may extend radially outward from the annular valve body to respective distal arm ends 2444. In this example, distal arm ends 2444 may be the portions of arms 2440 situated furthest from longitudinal axis 2800.

In some embodiments, the atrial anchoring arms may be configured to extend radially outward from an annular valve body of the exemplary prosthetic valve. As used herewith, the term "radially outward" may mean in a direction away from the center of the prosthetic valve (that is, from the longitudinal axis of the prosthetic valve). By way of example in FIGS. 2A and 2B, the atrial anchoring arms 2440 may extend radially outwards from the annular valve body 2020, with respect to longitudinal axis 2800. In some exemplary embodiments, one or more atrial anchoring arms may be physically connected to the annular valve body, such as by welding or adhesive. In some alternative embodiments, one or more atrial anchoring arms may be integrally formed with the annular valve body. In some embodiments, one or more atrial anchoring arms may be configured to extend from a single portion of the annular valve body. Alternatively, one or more atrial anchoring arms may be configured to extend from more than one portion of the valve body. In some embodiments, the one or more atrial anchoring arms may assume a radially-contracted configuration, where at least a portion, or, in some cases, the entire length of the one or more atrial anchoring arms does not extend radially outward from an annular valve body. For example, in FIGS. 5A and 5B, the atrial anchoring arms assume a radially-contracted state, and the entire length of the one or more atrial anchoring arms 2440 does not extend radially outward from the body. The prosthetic valve may also be configured to assume an arrangement in which the one or more atrial anchoring arms are radially-expanded but the annular valve body is radially contracted. For example, in FIGS. 5C and 5D, a portion of the one or more atrial anchoring arms 2440 extends radially outward. In some embodiments, the one or more atrial anchoring arms may assume a radially-expanded configuration, where at least a portion, or, in some cases, the entire length of the one or more atrial anchoring arms may extend radially outward from the annular valve body. For example, in FIG. 5E, at least the majority of the one or more atrial anchoring arms 2440 extend radially outward from the annular valve body 2000.

In some embodiments, the locations of connection between the atrial anchoring arms and annular valve body may be spaced at a regular interval about a circumference of the annular valve body. For example, in FIG. 2A, the atrial anchoring arms 2440 may extend from the annular valve body 2020 at arm attachment junctions 3202. Arm attachment junctions 3202 may be spaced at a regular interval about the circumference of annular valve body 2020. Additionally, or alternatively, the locations of connection between the atrial anchoring arms and annular valve body may be arranged along a plane perpendicular to the longitudinal axis of the prosthetic valve. For example, in FIG. 2A, the arm attachment junctions 3202 may be arranged along a plane perpendicular to longitudinal axis 2800. That is, the arm attachment junctions 3202 may be situated at the same axial position along longitudinal axis 2800.

In some embodiments, one or more atrial anchoring arms may extend from the atrial end of the valve body (that is, a portion of the valve body configured to be situated at a location within the atrium that is furthest from the adjacent ventricle). In some alternative embodiments, one or more atrial anchoring arms may extend from the ventricular end of the valve body (that is, a portion of the valve body configured to be situated at a location within the ventricle that is furthest from the adjacent atrium). In some further alternative embodiments, one or more atrial anchoring arms may extend from an intermediate portion of the valve body, the intermediate portion of the valve body constituting the portions of the valve body positioned between the atrial and ventricular ends of the valve body. For example, one or more exemplary atrial anchoring arms 2440 depicted in FIG. 2A may extend from an intermediate portion 2026 of annular valve body 2020. In some embodiments in which the annular valve body includes a plurality of struts, the one or more atrial anchoring arms may extend radially outwards from a strut junction. For example, in FIG. 3A, one or more atrial anchoring arms 2440 may extend from arm attachment junction 3202.

Exemplary atrial anchoring arms may be configured to anchor the prosthetic valve at the implantation site, such as within or near a native heart valve. In some embodiments, the atrial anchoring arms may be configured to be positioned at least partially within an atrium upon implantation of the prosthetic valve, and to engage atrial tissue of a native atrioventricular valve (e.g., a mitral valve) to anchor the prosthetic valve. As used herewith, the term "engage" may mean to be in contact with. For example, FIG. 10H depicts atrial anchoring arms 2440 situated within atrium 9010 and engaging the atrial side of native mitral valve 9030. In some embodiments, when an atrial anchoring arm engages with tissue, a portion of the arm may contact the tissue. Additionally, or alternatively, an atrial anchoring arm may contact the tissue and exert a force against the tissue. In some embodiments, the one or more atrial anchoring arms may be configured to minimize or prevent migration of the prosthetic valve in a ventricular direction, due to the engagement of the one or more atrial anchoring arms with mitral valve tissue. Additionally, or alternatively, the one or more atrial anchoring arms may be configured to grasp tissue of the native valve to further anchor the prosthetic valve in place. Optionally, one or more atrial anchoring arms may include an anchoring feature to couple the arms to surrounding tissue. The anchoring feature may be positioned on a tissue-engaging surface of the one or more atrial anchoring arms, such as at a distal end of the arm. Such anchoring features may include a hook, spike, corkscrew, spiral, helix, screw shaft, and/or any other anchoring feature suitable for anchoring the one or more atrial anchoring arm to tissue.

In some embodiments, the prosthetic valve may include a plurality (one or more) of ventricular anchoring legs. In some embodiments, the exemplary prosthetic valve may include two ventricular anchoring legs, three ventricular anchoring legs, four ventricular anchoring legs, five ventricular anchoring legs, six ventricular anchoring legs, seven ventricular anchoring legs, eight ventricular anchoring legs, nine ventricular anchoring legs, ten ventricular anchoring legs, eleven ventricular anchoring legs, twelve ventricular anchoring legs, thirteen ventricular anchoring legs, fourteen ventricular anchoring legs, fifteen ventricular anchoring legs, sixteen ventricular anchoring legs, seventeen ventricular anchoring legs, eighteen ventricular anchoring legs, nineteen ventricular anchoring legs, twenty ventricular anchoring legs, or any other suitable number of ventricular anchoring legs. For example, exemplary prosthetic valve 6000 in FIG. 2B may include twelve ventricular anchoring legs 2240.

In some embodiments, the prosthetic valve may include a plurality of ventricular anchoring legs configured to engage ventricular tissue of the native mitral valve to anchor the prosthetic valve. In reference to the ventricular anchoring legs, the term "proximal" refers to a portion of a respective ventricular anchoring leg in closest proximity to the prosthetic valve and may, in some embodiments, include a point of connection between the ventricular anchoring leg and the prosthetic valve. The term "distal" refers to a portion of the ventricular anchoring leg furthest from the point of connection between the ventricular anchoring leg and the prosthetic valve. In embodiments, the ventricular anchoring legs may be configured to extend radially outward from the prosthetic valve such that the distal leg ends may be the radially outer-most portions of the ventricular anchoring legs, with reference to the longitudinal axis of the prosthetic valve. For example, in FIGS. 2A and 5E, which depict the frame 2000 of an exemplary valve in a radially-expanded configuration, ventricular anchoring legs 2240 may be secured to the prosthetic valve (specifically, to outer frame tubular portion 3605) at proximal leg ends 3622 and may extend radially outward from the annular valve body to respective distal leg ends 2244. In this example, distal leg ends 2244 may be the portions of legs 2240 situated furthest from longitudinal axis 2800.

In some embodiments, the ventricular anchoring legs may be configured to extend radially outward from an annular valve body of the exemplary prosthetic valve. As used herewith, the term "radially outward" may mean in a direction away from the center of the prosthetic valve (that is, from the longitudinal axis of the prosthetic valve). By way of example in FIGS. 2A and 2B, the ventricular anchoring legs 2240 may extend radially outwards from the annular valve body 2020, with respect to longitudinal axis 2800. In some exemplary embodiments, one or more ventricular anchoring legs may be physically connected to the annular valve body, such as by welding or adhesive. In some alternative embodiments, one or more ventricular anchoring legs may be integrally formed with the annular valve body. In some embodiments, one or more ventricular anchoring legs may be configured to extend from a single portion of the annular valve body. Alternatively, one or more ventricular anchoring legs may be configured to extend from more than one portion of the valve body. In some embodiments, the one or more ventricular anchoring legs may assume a radially-contracted configuration, where at least a portion or, in some cases, the entire length of the one or more ventricular anchoring legs does not extend radially outward from an annular valve body. For example, in FIG. 5A, the one or more ventricular anchoring legs assume a radially-contracted state and the entire length of the one or more ventricular anchoring legs 2240 does not extend radially outward from the body. The prosthetic valve may also be configured to assume an arrangement in which the one or more ventricular anchoring legs are radially-expanded but the annular valve body is radially-contracted. For example, in FIGS. 5B and 5D, a portion of the one or more ventricular anchoring legs 2240 extends radially outward. In some embodiments, the one or more ventricular anchoring legs may assume a radially-expanded configuration, where at least a portion or, in some cases, the entire length of the one or more ventricular anchoring legs may extend radially outward from the annular valve body. For example, in FIG. 5D, the majority of the one or more ventricular anchoring legs 2240 extends radially outward from the annular valve body 2000.

In some embodiments, the locations of connection between the ventricular anchoring legs and annular valve body may be spaced at a regular interval about a circumference of the annular valve body. For example, in FIG. 2A, the ventricular anchoring legs 2240 may extend from the annular valve body 2020 at leg attachment junctions 3802. Leg attachment junctions 3802 may be spaced at a regular interval about the circumference of annular valve body 2020. Additionally, or alternatively, the locations of connection between the ventricular anchoring legs and annular valve body may be arranged along a plane perpendicular to the longitudinal axis of the prosthetic valve. For example, in FIG. 2A, the leg attachment junctions 3802 may be arranged along a plane perpendicular to longitudinal axis 2800. That is, the leg attachment junctions 3802 may be situated at the same axial position along longitudinal axis 2800.

In some embodiments, one or more ventricular anchoring legs may extend from the atrial end of the valve body (that is, a portion of the valve body configured to be situated at a location within the atrium that is furthest from the adjacent ventricle). In some alternative embodiments, one or more ventricular anchoring legs may extend from the ventricular end of the valve body (that is, a portion of the valve body configured to be situated at a location within the ventricle that is furthest from the adjacent atrium). In some further alternative embodiments, one or more ventricular anchoring legs may extend from an intermediate portion of the valve body, the intermediate portion of the valve body constituting the portions of the valve body positioned between the atrial and ventricular ends of the valve body. For example, exemplary ventricular anchoring legs 2240 depicted in FIG. 2A may extend from an intermediate portion 2026 of annular valve body 2020. In some embodiments in which the annular valve body includes a plurality of struts, the ventricular anchoring legs may extend radially outwards from a strut junction. For example, in FIG. 3C, ventricular anchoring legs 2240 may extend from leg attachment junction 3802. In exemplary prosthetic valves including an inner frame and an outer frame, one or more ventricular anchoring legs may extend from the inner frame, from the outer frame, or from both the inner and outer frames. For example, ventricular anchoring legs 2240 in FIG. 2A may extend from an intermediate portion 2026 of annular valve body 2020. More specifically, in FIG. 3C ventricular anchoring legs 2240 may extend from an intermediate portion 3606 of the outer frame tubular portion 3605 of outer frame 1200.

Exemplary ventricular anchoring legs may be configured to anchor the prosthetic valve at the implantation site, such as within or near a native heart valve. In some embodiments, the ventricular anchoring legs may be configured to be positioned at least partially within an atrium upon implantation of the prosthetic valve, and to engage atrial tissue of a native atrioventricular valve (e.g., a mitral valve) to anchor the prosthetic valve. As used herewith, the term "engage" may mean to be in contact with. For example, FIG. 10E depicts ventricular anchoring legs 2240 situated within ventricle 9020 and engaging the ventricular side of native mitral valve 9030. In some embodiments, when a ventricular anchoring leg engages with tissue, a portion of the leg may contact the tissue. Additionally, or alternatively, a ventricular anchoring leg may contact the tissue and exert a force against the tissue. In some embodiments, the ventricular anchoring legs may be configured to minimize or prevent migration of the prosthetic valve in an atrial direction, due to the engagement of the legs with mitral valve tissue. Additionally, or alternatively, the ventricular anchoring legs may be configured to grasp tissue of the native valve to further anchor the prosthetic valve in place. Optionally, one or more ventricular anchoring legs may include an anchoring feature to couple the legs to surrounding tissue. The anchoring feature may be positioned on a tissue-engaging surface of the one or more ventricular anchoring legs, such as at a distal end of the leg. Such anchoring features may include a hook, spike, corkscrew, spiral, helix, screw shaft, and/or any other anchoring feature suitable for anchoring the ventricular anchoring leg to tissue.

According to embodiments in which an exemplary prosthetic valve includes both atrial anchoring arms and ventricular anchoring legs, the valve may include the same number of atrial anchoring arms and ventricular anchoring legs. For example, exemplary prosthetic valve 6000 may include twelve atrial anchoring arms 2440 and twelve ventricular anchoring legs 2200. Alternatively, the valve may include more atrial anchoring arms than ventricular anchoring legs. Alternatively, the valve may include fewer atrial anchoring arms than ventricular anchoring legs.

In some embodiments, exemplary atrial anchoring arms of the prosthetic valve may extend radially from the annular valve body within the atrium while the annular valve body remains contracted. For example, as shown in FIG. 10F, the atrial anchoring arms 2440 of the prosthetic valve extend radially from the valve body while the annular valve body remains radially-contracted. The atrial anchoring arms may be configured to engage the atrial side of the native mitral valve. In some embodiments, the atrial anchoring arms may contact a portion of the anterior leaflet of the native mitral valve or a portion of the posterior leaflet of the native mitral valve, or both. The atrial anchoring arms may also contact the mitral annulus. In some embodiments, the atrial anchoring arms may be configured to exert force on the native mitral valve tissue in the direction of the ventricle. For example, at least a portion of at least one atrial anchoring arm may be constructed of a rigid, shape-memory material, such as Nitinol, and may be sufficiently rigid so as to resist deformation. Upon implantation, native valve tissue may slightly deform the at least one atrial anchoring arm in an atrial direction; however, the atrial anchoring arm may resist the deformation and accordingly exert a ventricularly-directed force on the tissue. By way of example, exemplary atrial anchoring arm 2440 depicted in FIG. 3B may include an inflexible portion 3402, which may be constructed of a rigid material and may be devoid of a structure which may increase flexibility (such as serpentine structure 3406). Accordingly, as shown in FIG. 10H, inflexible portion 3402 of exemplary atrial anchoring arms 2440 may engage and exert a ventricularly-directed force on native leaflets 9032, pushing the tissue towards ventricular anchoring legs 2240.

In some embodiments, exemplary ventricular anchoring legs may extend radially from the annular valve body within the ventricle while the annular valve body remains contracted. For example, as shown in FIG. 10E, the ventricular anchoring legs 2240 of the prosthetic valve extend radially from the valve body while the annular valve body remains in a radially-contracted configuration. The ventricular anchoring legs may be configured to engage a ventricular side of the native mitral valve. In some embodiments, the ventricular anchoring legs may engage on a portion of the anterior leaflet or a portion of the posterior leaflet of the native mitral valve, or both. The ventricular anchoring leg may also engage a portion of the mitral annulus. In some embodiments, the ventricular anchoring legs may engage the portion of the posterior or anterior leaflet in between the commissure but may not engage the leaflet extending all the way to the commissure. By way of example, as shown in FIGS. 10D-10E, once in the ventricle, the ventricular anchoring legs are pulled upwards so the distal ends are brought into contact with the ventricular side of the mitral valve. By way of non-limiting example with reference to FIGS. 2E and 10E, the ventricular anchoring legs 2240 engage tissue of the mitral valve 9030 and enclose an area of tissue defined by the distal ends of the ventricular anchoring legs 2240. In some embodiments, when the exemplary atrial anchoring arms and ventricular anchoring legs engage the native mitral valve, tissue including the native valve leaflets may be sandwiched between the arms and legs. That is, the tissue may be firmly grasped between the atrial anchoring arms and ventricular anchoring legs due, at least in part, to the ventricularly-directed force applied by the arms and the atrially-directed force applied by the legs. This sandwiching of native tissue may securely anchor the prosthetic valve within the mitral valve. In some embodiments, the ventricular anchoring legs may be configured to exert force on the native mitral valve tissue in the direction of the atrium. For example, the entire length of a ventricular anchoring leg may be constructed of a rigid, shape-memory material, such as Nitinol, and may be sufficiently rigid so as to resist deformation. Upon implantation, the ventricular anchoring leg may resist deformation and accordingly exert an atrially-directed force on the tissue. By way of example, as shown in FIG. 10H, exemplary inflexible ventricular anchoring leg portion 2240 may engage and exert an atrially-directed force on native leaflets 9032, pushing the tissue towards atrial anchoring arms 2440.

In some embodiments, when the atrial anchoring arms and ventricular anchoring legs engage the native mitral valve, a volume may be formed between the atrial anchoring arms and ventricular anchoring legs. The volume may be a three-dimensional space formed between some or all of the plurality of atrial anchoring arms and the ventricular anchoring legs, such as when the atrial anchoring arms and ventricular anchoring legs are in a radially-expanded configuration. The volume may be annular or ring-shaped when formed between all of the plurality of atrial anchoring arms and ventricular anchoring legs. By way of example, FIG. 4B depicts an exemplary volume 4000 formed between ventricular anchoring legs 2240 and atrial anchoring arms 2440. Although FIG. 4B depicts volume 4000 within a cross-sectional view of frame 2000, one of ordinary skill will understand that the volume 4000 forms a continuous ring around the longitudinal axis 2800, as arms 2400 and ventricular anchoring legs 2200 extend about the entire circumference of frame 2000.

In some embodiments, the annular valve body, atrial anchoring arms, and ventricular anchoring legs may be configured to radially expand independently of the other components of the prosthetic valve. For example, as depicted in FIGS. 5A and 5B, ventricular anchoring legs 2240 may be configured to deflect radially outward while atrial anchoring arms 2440 and annular valve body 2020 remain in a radially-contracted configuration. Similarly, as depicted in FIGS. 5A and 5C, atrial anchoring arms 2440 may be configured to deflect radially outward while ventricular anchoring legs 2240 and annular valve body 2020 remain in a radially-contracted configuration. Further, the annular valve body 2020 may be configured to remain in a radially-contracted configuration when atrial anchoring arms 2440 and ventricular anchoring legs 2240 are both deployed (e.g., FIG. 5D). Annular valve body 2020 may subsequently be expanded (e.g., FIG. 5E), which may shift atrial anchoring arms 2440 and ventricular anchoring legs 2240 radially outward, and which may also decrease the axial distance between atrial anchoring arms 2440 and ventricular anchoring legs 2240.

In an exemplary method of deploying the prosthetic valve in a native mitral valve, the ventricular anchoring legs may be released and may deflect radially outward while the atrial anchoring arms and annular valve body remain in a radially-contracted configuration (e.g., within a delivery device, such as exemplary delivery capsule 7300). For example, as shown in FIGS. 10B-10C, the ventricular anchoring legs 2240 may be released and extend radially outward once in the atrium 9010 or the ventricle 9020, while the atrial anchoring arms 2440 and the valve body remain in a radially contracted state. The ventricular anchoring legs may be deployed within, or otherwise moved into, the left ventricle and may be maneuvered such that the deployed legs may grasp the ventricular side of the native mitral valve. In some embodiments, the deployed ventricular anchoring legs may be configured to firmly grasp the mitral valve leaflets and pull them together, due in part to the shape memory properties of the ventricular anchoring legs. In some embodiments, the ventricular anchoring legs may be configured to pull the mitral valve leaflets together until they are positioned against the radially-constrained atrial anchors and annular valve body, thus grasping the native mitral valve substantially closed. For example, as depicted in FIG. 10E, the ventricular anchoring legs 2240 are radially extended and grasp the ventricular side of the mitral valve leaflets 9032, pulling the leaflets together until the leaflets are held against the constrained atrial anchoring arms 2440 and annular valve body 2020. As a result, mitral valve 9030 may be held in a closed position by the deployed ventricular anchoring legs 2240.

The atrial anchoring arms may then be deployed, thus retaining the tissue between the atrial anchoring arms and the ventricular anchoring legs. For example, as depicted in FIG. 10G, after the atrial anchoring arms 2440 are released, the mitral valve tissue may be held between the arms 2440 and the ventricular anchoring legs 2240. Upon radial expansion of the annular valve body, the native valve tissue may be firmly grasped or "sandwiched" between the atrial anchoring arms and ventricular anchoring legs due to the reduction of the distance between the arms and legs caused by expansion of the annular valve body. In addition, the volume formed between the atrial anchoring arms and ventricular anchoring legs may be substantially filled with tissue upon radial expansion of the annular valve body. For example, as depicted in FIG. 10H, the arms and legs sandwich the native valve tissue 9032, such that the volume between the arms and legs is substantially filled with tissue.

In some embodiments, the volume formed between the atrial anchoring arms and ventricular anchoring legs may be substantially filled with tissue due, at least in part, to the small axial distance between the arms and legs when the annular valve body is radially expanded. For example, in some embodiments the expansion of the annular valve body may decrease the distance between the atrial anchoring arms and the ventricular anchoring legs such that the distal end of at least one leg may extend in an atrial direction beyond a portion of the arms. As shown in FIG. 5D, the atrial anchoring arms 2440 and ventricular anchoring legs 2240 may be separated by a distance 5004 when the annular valve body is radially contracted. When the valve body is radially-expanded as depicted in FIG. 5E, the atrial anchoring arms and ventricular anchoring legs are brought close together spatially. In some embodiments, when the annular valve body is expanded, the distal end of the at least one ventricular anchoring leg may be positioned in an atrial direction relative to at least a portion of the atrial anchoring arms. As depicted in FIG. 2C, the distal end 2244 of at least one ventricular anchoring leg 2240 extends in an atrial direction relative to a portion of the atrial anchoring arm that overlaps with the ventricular anchoring leg 2446. This arrangement may result in the tissue that is grasped between the atrial anchoring arms and ventricular anchoring legs being forced into a reduced volume when the annular valve body is expanded. The opposing forces of the atrial anchoring arms and ventricular anchoring legs, which are biased towards a configuration in which portions thereof are axially aligned, may force tissue into the reduced volume until the volume is filled with tissue. For example, as depicted in FIG. 10H, portions of the mitral valve tissue 9032 is sandwiched and forced into the volume between the atrial anchoring arms and ventricular anchoring legs. In addition, the entire length of at least one ventricular anchoring leg may be configured to extend in an atrial direction. For example, as depicted in FIG. 3C, the entire length of the ventricular anchoring legs 2240 from distal end 2244 to leg attachment junction 3802 is configured to extend in the atrial direction. Similarly, the exemplary rigid portion of the at least one atrial anchoring arm may be configured to extend in a direction perpendicular to the longitudinal axis or, in some embodiments, in a ventricular direction. For example, as depicted in FIG. 3B, the rigid portion of atrial anchoring arm 2440, extending from the distal end 3402d of the inflexible portion of the atrial anchoring arm to the proximal end 3402p of the inflexible portion of atrial anchoring arm, may be configured to extend in a direction perpendicular to the longitudinal axis 2800. As a result, the entire ventricular anchoring leg and the entire rigid portion of the atrial anchoring arm may be configured to exert opposing forces on the tissue, and the volume between the atrial anchoring arms and ventricular anchoring legs may be devoid of excess space which the native valve tissue might be unable to fill. As a result, the volume formed between the atrial anchoring arms and ventricular anchoring legs may be substantially filled with tissue. Further, the exemplary annular valve body, with the atrial anchoring arms and ventricular anchoring legs extending therefrom, may be symmetrical about the longitudinal axis thereof. For example, exemplary struts forming the annular valve body may be constructed in regular, repeating pattern. In addition, the atrial anchoring arms and ventricular anchoring legs may be arranged at regular intervals around the circumference of the annular valve body. For example, as shown in FIG. 2B for an exemplary valve, twelve arms 2440 and twelve legs 2240 are arranged at regular intervals around the circumference of the angular valve body. As a result, the entire three-dimensional volume between the atrial anchoring arms and ventricular anchoring legs may be configured to be filled with tissue because the arms and legs may be configured to exert the above-described forces on tissue about the entire circumference of the annular valve body.

In some embodiments, the substantial filling of the volume between the atrial anchoring arms and ventricular anchoring legs with tissue may refer to the volume being substantially devoid of gaps when the annular valve body is expanded. As used herein, the term "gap" can be defined as an unfilled space; it may include, for example, a space between the atrial anchoring arms and ventricular anchoring legs not filled by native valve tissue.

In some embodiments, the exemplary volume between the atrial anchoring arms and ventricular anchoring legs may be formed between an outer surface of the annular valve body, one or more surfaces of the ventricular anchoring legs, and one or more surfaces of the atrial anchoring arms. That is, the exemplary volume may be bounded by the outer surface of the annular valve body, the one or more surfaces of the ventricular anchoring legs, and the one or more surfaces of the atrial anchoring arms. In some embodiments, the one or more surfaces of the ventricular anchoring legs may face an atrium when the prosthetic valve is implanted within a native atrioventricular valve (e.g., a native mitral valve). Additionally, or alternatively, the one or more surfaces of the atrial anchoring arms may face a ventricle when the prosthetic valve is implanted within a native atrioventricular valve (e.g., a native mitral valve). The exemplary volume may be formed by the outer surface of the valve body, and the aforementioned surfaces of the plurality of arms and ventricular anchoring legs, resulting in the volume having an annular shape around the central axis of the valve. By way of example as shown in FIGS. 4A and 4B, the volume 4000 between the atrial anchoring arms and ventricular anchoring legs may be formed between the outer surface 4010 of the annular valve body, surfaces 2248 of the ventricular anchoring legs facing toward an atrium (i.e., in an atrial direction), and surfaces 2449 of the atrial anchoring arms facing toward a ventricle (i.e., in a ventricular direction).

As described above, in some embodiments of the exemplary prosthetic valve, at least a portion of an atrial anchoring arm and at least a portion of a ventricular anchoring leg are configured to be aligned in a common lateral plane (that is, in a plane that is perpendicular to the longitudinal axis of the prosthetic valve). That is, a portion of an atrial anchoring arm and a portion of a ventricular anchoring leg may be arranged at the same axial position relative to the longitudinal axis of the exemplary prosthetic valve. In some embodiments, the portions of the atrial anchoring arm and ventricular anchoring leg may be configured to be aligned in a common lateral plane when the prosthetic valve is in a radially-expanded configuration. That is, the portions of the atrial anchoring arm and ventricular anchoring leg may be configured to be aligned in a plane that is perpendicular to the longitudinal axis of the prosthetic valve. By way of example in FIG. 2C, an exemplary valve may be configured such that a portion 2246 of at least one ventricular anchoring leg 2240 may be configured to be substantially aligned in a common lateral plane with a portion 2446 of at least one atrial anchoring arm 2440, and where the common lateral plane is a plane perpendicular to the longitudinal axis 2800. That is, leg portion 2246 and arm portion 2446 may be arranged at the same axial position relative to longitudinal axis 2800. In some embodiments, more than one portion of at least one atrial anchoring arm and/or or more than one portion of at least one ventricular anchoring leg may be so aligned with the common lateral plane.

In some embodiments of an exemplary prosthetic valve, a circumference about the longitudinal axis may be formed by the overlapping portions of the ventricular anchoring legs and atrial anchoring arms. For example, the aforementioned portions of the ventricular anchoring legs may be positioned an equal distance from the longitudinal axis as are the aforementioned portions of the atrial anchoring arms. Additionally, or alternatively, the overlapping portions of the atrial anchoring arms and ventricular anchoring legs may be positioned at a common height of the prosthetic valve (that is, may be positioned in a plane perpendicular to the longitudinal axis). As a result, a circumference may be drawn about the annular valve body which may pass through the overlapping portions of the atrial anchoring arms and ventricular anchoring leg. In some embodiments, this circumference may form a radially outer boundary of the volume between the atrial anchoring arms and the ventricular anchoring legs. For example, as can be seen in FIG. 2C, the overlapping portions 2246, 2446 of the ventricular anchoring legs and atrial anchoring arms may form an outer boundary of the volume 4000, with respect to longitudinal axis 2800.

In some embodiments, at least one atrial anchoring arm of the exemplary prosthetic valve may include at least a first portion configured to extend towards a ventricle (that is, in a ventricular direction) and at least a second portion configured to extend toward an atrium (that is, in an atrial direction). In some embodiments, the first and second portions of the at least one atrial anchoring arm may be so configured when the at least one atrial anchoring arm is in a radially-expanded configuration (for example, as depicted in FIGS. 3B and 5E). The at least one atrial anchoring arm may include a plurality of portions configured to extend towards a ventricle and/or a plurality of portions configured to extend towards an atrium. For example, as depicted in FIG. 3B, an exemplary atrial anchoring arm 2440 may include a first portion 3504 configured to extend toward a ventricle and a second portion 3506 configured to extend toward an atrium. In some embodiments, exemplary atrial anchoring arm 2440 may additionally include a third portion 3502 configured to extend toward the atrium.

In some embodiments, the first portion of the at least one atrial anchoring arm may be configured to form a boundary of the volume between the atrial anchoring arms and the ventricular anchoring legs. That is, the exemplary volume may be bounded, in part, by the first portion of the at least one atrial anchoring arm. This can be seen in an exemplary valve as shown in FIGS. 3B and 4B, where the first portion 3504 of an atrial anchoring arm may be configured to form a boundary of the volume 4000 between the atrial anchoring arms and ventricular anchoring legs. In some embodiments, the first portion of the at least one atrial anchoring arm may extend along an atrial boundary (that is, an upper boundary) of the volume between the atrial anchoring arms and ventricular anchoring legs.

In some embodiments, at least a portion of the exemplary second portion of the at least one atrial anchoring arm may be situated radially outward from the volume between the atrial anchoring arms and ventricular anchoring legs. That is, at least a portion of the exemplary second portion may not form part of the boundary of the volume, and may instead be positioned radially outward from the volume, relative to the longitudinal axis of the prosthetic valve. In some embodiments, the entirety of the second portion of the at least one atrial anchoring arm may be situated radially outward from the volume. By way of example in FIGS. 3B, 4A, and 4B, an exemplary atrial anchoring arm may have a second portion 3506 that may be situated radially outward from the volume 4000 formed between the atrial anchoring arms and ventricular anchoring legs.

In some embodiments, the exemplary second portion of the at least one atrial anchoring arm may be configured to be situated radially outward from the exemplary first portion of the at least one atrial anchoring arm. For example, the first and second portions may be so configured when the at least one atrial anchoring arm is in a radially-expanded configuration. In some embodiments, the first portion may be immediately adjacent to the second portion. In the example depicted in FIG. 3B, the second portion 3506 of atrial anchoring arm 2440 may be situated radially outward from the first portion 2504.

In some embodiments, the exemplary first portion of the atrial anchoring arm may have a flexibility which may vary between the radially inner end of the first portion (that is, the proximal end of the first portion) and a radially outer end of the first portion (that is, the distal end of the first portion). In some embodiments, the radially inner end of the first portion may be more flexible than the radially outer end of the first portion. Alternatively, the radially inner end of the first portion may be less flexible than the radially outer end of the first portion. In some embodiments, the variable flexibility along the first portion of the at least one atrial anchoring arm may be due, at least in part, to different structural configurations at the radially inner and outer ends of the first portion. For example, atrial anchoring arm 2440 illustrated in FIG. 3B may include a first portion 3504 extending between an inflexible portion 3402 of the atrial anchoring arm and a serpentine structure 3406 of the atrial anchoring arm. The serpentine structure 3406 may be positioned distally of the inflexible portion 3402 and may be more flexible than inflexible portion 3402 due to the serpentine structure's thin, zig-zagging configuration (see FIG. 3B). The radially inner end of the first portion 3504 may be situated within the inflexible portion 3402, while the radially outer end of the first portion 3504 may be situated within the serpentine structure 3406. As a result, at least a portion of the serpentine structure 3406 may be situated within the first portion 3504 which is configured to extend in a ventricular direction.

In some embodiments, a prosthetic valve may be configured such that when a plurality of ventricular anchoring legs extend radially outward form the annular valve body, a shape formed by the terminal ends of the legs may constitute a circular outer circumference. For example, as depicted in FIG. 2E, an exemplary prosthetic valve may include a ventricular anchoring leg circumference 2620 defined by terminal ends of the ventricular anchoring legs 2240. In some embodiments, the outer circumference formed by the terminal ends of the ventricular anchoring legs may have a diameter of between 40 millimeters and 55 millimeters. For example, and without limitation, the outer circumference may have a diameter of 40 millimeters, 41 millimeters, 42 millimeters, 43 millimeters, 44 millimeters, 45 millimeters, 46 millimeters, 47 millimeters, 48 millimeters, 49 millimeters, 50 millimeters, 51 millimeters, 52 millimeters, 53 millimeters, 54 millimeters, or 55 millimeters. In addition, the exemplary prosthetic valve may be configured such that a shape formed by an interior surface of the annular valve body in a plane perpendicular to the longitudinal axis may constitute a circular inner circumference. In some embodiments, the inner circumference of the annular valve body may have a diameter of between 25 millimeters and 30 millimeters. For example, and without limitation, the inner diameter may have a diameter of 25 millimeters, 25.5 millimeters, 26 millimeters, 26.5 millimeters, 27 millimeters, 27.25 millimeters, 27.5 millimeters, 27.75 millimeters, 28 millimeters, 28.25 millimeters, 28.5 millimeters, 28.75 millimeters, 29 millimeters, 29.5 millimeters, or 30 millimeters. In some embodiments, the inner circumference of the annular valve body may be the inner circumference of the atrial end of the annular valve body. For example, as depicted in FIG. 2D, an exemplary prosthetic valve may include an inner circumference of the annular valve body having a radius 2520, which may constitute the inner circumference of the atrial end of the exemplary annular valve body 2020. In other embodiments, the inner circumference of the annular valve body may be the inner circumference of the ventricular end of the annular valve body. In further alternative embodiments, the inner circumference of the annular valve body may be the inner circumference of another portion of the annular valve body. In some embodiments, the outer circumference formed by the terminal ends of the ventricular anchoring legs may have a diameter which may be about 1.6 times to about 1.8 times larger than a diameter of the inner circumference formed by the annular valve body. For example, and without limitation, the outer circumference formed by the terminal ends of the ventricular anchoring legs may have a diameter which may be 1.6 times, 1.62 times, 1.64 times, 1.65 times, 1.66 times, 1.68 times, 1.7 times, 1.72 times, 1.74 times, 1.75 times, 1.76 times, 1.78 times, or 1.8 times larger than a diameter of the inner circumference formed by the annular valve body. In some embodiments, the inner circumference formed by the annular valve body may vary along the longitudinal axis, but the diameter of the outer circumference may still be about 1.6 times to about 1.8 times larger than the diameter of the inner circumference anywhere along the longitudinal axis.

In some embodiments, a prosthetic valve may be configured such that the inner circumference of the annular valve body may be defined by an inner surface of the annular valve body to which one or more prosthetic leaflets may be coupled. FIG. 6D, for example, illustrates prosthetic leaflets 6602, 6604, 6606 situated within the interior lumen 2022 of annular valve body 2020. The prosthetic valve may include two leaflets, three leaflets, four leaflets, or any other suitable number of leaflets. The leaflets may be constructed of various suitable materials, such as natural tissue (e.g., bovine pericardial tissue) or synthetic materials. The leaflets may be configured to permit blood flow in one direction (e.g., from the atrium to the ventricle) and may prevent flow in a second, opposite direction (e.g., from the ventricle to the atrium). In some embodiments, the leaflets may be connected directly to one or more portions of the inner surface of the annular valve body. Additionally, or alternatively, the leaflets may be connected to an intermediate structure (e.g., a liner) which may, in turn, be connected to the inner surface of the annular valve body. The leaflets may be connected to the annular valve body and/or to the intermediate structure by stitching, adhesive, staples, rivets, and/or any suitable fasteners, or some combination thereof.

In some embodiments, the inner surface of the annular valve body may surround a central lumen of the annular valve body. In some embodiments, the one or more prosthetic leaflets may be coupled directly to the inner surface of the annular valve body, such as by stitching, adhesive, or other known coupling mechanisms. Additionally, or alternatively, the one or more prosthetic leaflets may be directly coupled to an intervening feature (e.g., a liner situated in the central lumen of the annular valve body) which may in turn be coupled directly to the inner surface of the annular valve body. For example, FIGS. 6D and 6E illustrate an exemplary prosthetic heart valve 6000 having three prosthetic leaflets 6602, 6604, 6606 situated within the lumen 2022 of the annular valve body 2020 of the prosthetic heart valve. In some embodiments, leaflets 6602, 6604, 6606 may be secured (e.g., via stitching) to an inner liner 6400, which may in turn be secured (e.g., via stitching) to inner surface 4020 of the annular valve body. Additionally, or alternatively, at least a portion of leaflets 6602, 6604, 6606 may be secured directly to the inner surface 4020 of the annular valve body, such as by stitching.

In some embodiments, the atrial anchoring arms and ventricular anchoring legs may be angularly offset from each other, relative to the longitudinal axis of the prosthetic valve. That is, the atrial anchoring arms and ventricular anchoring legs may be situated at different positions about the circumference of the annular valve body. In some embodiments, the atrial anchoring arms and ventricular anchoring legs may be spaced at a regular interval about the circumference of the annular valve body. Alternatively, the atrial anchoring arms and ventricular anchoring legs may be spaced in a different pattern about the circumference of the annular valve body. Advantageously, the angular offset between the atrial anchoring arms and ventricular anchoring legs may prevent the arms and legs from contacting, damaging, or otherwise hindering the movement or functionality of the other. The angular offset may also allow the arrangement discussed above in reference to FIG. 4B, in which the distal end of the at least one ventricular anchoring leg may be positioned in an atrial direction relative to at least a portion of the atrial anchoring arms. An exemplary prosthetic valve shown in FIG. 2B includes atrial anchoring arms 2440 and ventricular anchoring legs 2240 which are angularly offset from each other around the longitudinal axis 2800.

In some embodiments, a prosthetic valve with a plurality of ventricular anchoring legs may have at least one ventricular anchoring leg that may include at least one curved portion. The term "curved" as used herewith, denotes a ventricular anchoring leg that is curved or bent, and is not limited in the direction or degree of curvature. For example, the ventricular anchoring leg may curve towards the central axis of the valve, or it may curve away. In some embodiments, the at least one ventricular anchoring leg may include two or more curved portions. The two or more curved portions may face in the same direction (e.g., in a direction facing radially-inward) or may face in different directions. An example of an exemplary ventricular anchoring leg 2240 may be shown in FIG. 3D. Exemplary ventricular anchoring leg 2240 may include two curved portions 3807 and 3808 which may curve in different directions. For example, curved portion 3807 may face radially outward while curved portion 3808 may face radially inward.

In some embodiments, an exemplary prosthetic valve with a plurality of atrial anchoring arms may include at least one atrial anchoring arm, the radially inner-most portion of which may be configured to extend towards an atrium (that is, in an atrial direction). The radially inner-most potion of the at least one atrial anchoring arm may refer to the proximal end of the arm, that is, to the end of the arm immediately adjacent to the location of connection between the arm and the annular valve body. In some exemplary embodiments, the radially inner-most portion of the at least one atrial anchoring arm may be configured to extend towards the atrium in a direction parallel to the longitudinal axis of the prosthetic valve. Additionally, or alternatively, the radially inner-most portion of the at least one atrial anchoring arm may be configured to extend towards the atrium in a direction which is not parallel to the longitudinal axis of the prosthetic valve. In some embodiments, the inner-most portion of the at least one atrial anchoring arm may be configured to extend towards the atrium when the arm is in a radially-contracted configuration. For example, as depicted in FIG. 5A, the inner-most portion 3020 of the atrial anchoring arm extends towards the atrium when the arm is in the radially-contracted configuration. Additionally, or alternatively, the inner-most portion of the at least one atrial anchoring arm may be configured to extend towards the atrium when the arm is in a radially-contracted configuration. As illustrated in FIG. 3B, the radially inner-most portion 3020 of atrial anchoring arm 2440 may be configured to extend towards the atrium (i.e., in an atrial direction) when the arm is in a radially-expanded configuration In some embodiments, an exemplary prosthetic valve with a plurality (that is, one or more) of ventricular anchoring legs may include at least one ventricular anchoring leg for which the entire length of the ventricular anchoring leg may be configured to extend toward an atrium (that is, in an atrial direction). In some embodiments, the entire length of the ventricular anchoring leg may be configured to extend toward an atrium when the leg is in a radially-contracted configuration. For example, as depicted in FIG. 5A, the entire length of ventricular anchoring leg 2240 (from distal leg end 2244 to leg attachment junction 3802) extends toward an atrium when the ventricular anchoring leg is in the radially-contracted configuration. Additionally, or alternatively, the entire length of the ventricular anchoring leg may be configured to extend toward an atrium when the ventricular anchoring leg is in a radially-expanded configuration. For example, as depicted in FIGS. 3C and 5E, the entire length of ventricular anchoring leg 2240 (from distal leg end 2244 to leg attachment junction 3802) extends toward an atrium when the ventricular anchoring leg is in the radially-expanded configuration. In some embodiments, more than one ventricular anchoring leg may be configured such that the entire length of the one or more ventricular anchoring legs may extend towards an atrium. In some exemplary embodiments, the entire length of the ventricular anchoring leg may refer to the portion of the leg extending between the point of connection of the leg with the annular valve body and the terminal end of the leg. For example, in FIGS. 3C and 3D, the entire length of ventricular anchoring leg 2240 may constitute the portion of leg 2240 extending between leg attachment junction 3802 and terminal leg end 2244 and may, optionally, include one or both of leg attachment junction 3802 and terminal leg end 2244. As shown by FIGS. 2A, 3C and 3D on an exemplary prosthetic valve leg, the entire length of at least one ventricular anchoring leg 2240 from the proximal end 3622 to the distal end 2244 may be configured to extend toward an atrium where the atrial end of the annular valve body may be labeled as 2024.

In some embodiments, the exemplary annular valve body may include an atrial end. In some embodiments, the term atrial end may refer to a portion of a feature of the annular valve body configured to be situated closest to an atrium of the heart when the feature is positioned outside of the atrium. Additionally, or alternatively, the term atrial end may refer to a portion of a feature of the annular valve body configured to be situated at a location within the atrium that is furthest from an adjacent ventricle. For example, as depicted in FIGS. 2A and 3A, atrial end inner frame junctions 3002 may constitute the atrial end 2024 of annular valve body 2020 because they are the portions of annular valve body 2020 which are situated within atrium 9010 at a location furthest from ventricle 9020 (as shown in FIG. 10H). In some embodiments, the exemplary annular valve body may include a ventricular end. In some embodiments, the term ventricular end may refer to a portion of a feature of the annular valve body configured to be situated closest to a ventricle of the heart when the feature is positioned outside of the ventricle. Additionally, or alternatively, the term ventricular end may refer to a portion of a feature of the annular valve body configured to be situated at a location within the ventricle that is furthest from an adjacent atrium. For example, in some embodiments and as depicted in FIGS. 2A, 3A, and 3C, the ventricular end inner frame junctions 3004 and the ventricular end outer frame junctions 3604 may constitute the ventricular end 2025 of annular valve body 2020. In some alternative embodiments, the ventricular end inner frame junctions 3004 may constitute the ventricular end 2025 of valve body 2020. In some further alternative embodiments, the ventricular end outer frame junctions 3604 may constitute the ventricular end 2025 of valve body 2020.

In some embodiments, the exemplary valve body may include both an atrial end and a ventricular end opposite the atrial end. That is, the ventricular end of the valve body may be situated at a portion of the valve body that is furthest from and opposite of the atrial end of the valve body, with respect to a longitudinal axis of the valve body. In some embodiments, the exemplary valve body may include an intermediate portion extending between the atrial and ventricular ends of the valve body. In some embodiments, the intermediate portion may constitute every portion of the valve body situated in between the atrial and ventricular ends of the valve body. For example, as depicted in FIG. 2A, intermediate portion 2026 of valve body 2020 may include every portion of the valve body positioned between atrial end 2024 and ventricular end 2025. In some such embodiments, at least one of the atrial anchoring arms and ventricular anchoring legs may be configured to extend from the intermediate portion. In some embodiments, the atrial anchoring arms and the ventricular anchoring legs may extend from the intermediate portion of the annular valve body. By way of example in FIG. 2A, an exemplary valve may have atrial anchoring arms 2440 and ventricular anchoring legs 2240 which may be configured to extend from an intermediate portion 2026 of an annular valve body, which may extend between the atrial end 2024 and ventricular end 2025 of the annular valve body 2020.

According to exemplary embodiments, the annular valve body may include one or more frames. In some embodiments, the annular valve body may include an outer frame and an inner frame situated at least partially within the outer frame. The outer frame may be annular, and the inner frame may be positioned within an opening of the outer frame. In some embodiments, the inner and outer frames of the annular valve body may include a stent-like tubular portion constructed of a plurality of struts intersecting at junctions to form a lattice or overlapping pattern. For example, in FIG. 3A, inner frame 2400 of exemplary prosthetic valves may include inner frame atrial struts 3008*a*, inner frame intermediate struts 3008*b*, and inner frame ventricular struts 3008*c*, which may intersect at arm attachment junction 3202 and inner frame junction 3204 to form an inner frame tubular portion 3005. The struts of inner frame 2400 may intersect to form closed cells 3012, 3014, which may be diamond-shaped in some embodiments; however, exemplary struts according to the present disclosure may intersect to form any suitable cell shape. Another example may be depicted in FIG. 3C, which illustrates an outer frame 2200 of exemplary prosthetic valves. Outer frame 2200 may include outer frame atrial circumferential struts 3608*a*, outer frame leg base struts 3608*b*, and outer frame ventricular circumferential struts 3608*c*, which may intersect at atrial end outer frame junctions 3602, leg attachment junctions 3802, outer frame junctions 3804, and ventricular end outer frame junctions 3604 to form an outer frame tubular portion 3605. The struts of outer frame 2200 may intersect to form closed cells 3616, which may be chevron-shaped in some embodiments; however, exemplary struts according to the present disclosure may intersect to form any suitable cell shape. In some exemplary prosthetic valves including inner and outer frames, a tubular portion of the inner frame and a tubular portion of the outer frame may together form the annular valve body of the prosthetic valve.

In some embodiments in which a prosthetic valve may have an annular valve body that may include an annular outer frame and an inner frame situated at least partially within the annular outer frame, the atrial anchoring arms may extend from the inner frame and the ventricular anchoring legs may extend from the annular outer frame. In some exemplary embodiments, the atrial anchoring arms may be physically connected to the inner frame, such as by welding or adhesive. In some alternative embodiments, the atrial anchoring arms may be integrally formed with the inner frame. Similarly, in some exemplary embodiments, the ventricular anchoring legs may be physically connected to the annular outer frame, such as by welding or adhesive. In some alternative embodiments, the ventricular anchoring legs may be integrally formed with the annular outer frame. By an example shown in FIG. 2A, the annular valve body 2020 may include an annular outer frame 2200 and an inner frame 2400. The ventricular anchoring legs 2240 may extend from the outer frame 2200 and the atrial anchoring arms 2440 may extend from the inner frame 2400.

In some embodiments, the exemplary prosthetic valve may be configured for radial expansion, such as between a radially-contracted configuration (e.g., a crimped state) and a radially-expanded configuration. In some embodiments, an exemplary prosthetic valve may be configured to be radially contracted into the radially-contracted configuration for introduction to the implantation site, such as on or within a delivery device. Accordingly, in some embodiments the radially-contracted configuration may also be a delivery configuration, in which the prosthetic valve may be arranged for delivery to the implantation site. Once at or near the implantation site, the prosthetic valve may be radially expanded to a radially-expanded configuration, in which the prosthetic valve may be anchored at the implantation site. Accordingly, in some embodiments the radially-expanded configuration may also be a deployed configuration, in which the prosthetic valve may be released from the delivery tool and seated at the implantation site.

In some embodiments, the transition of the prosthetic valve between a radially-contracted configuration and a radially-expanded configuration may include transition of the atrial anchoring arms between a radially-contracted configuration and a radially-expanded configuration. The ventricular anchoring legs may also be configured to transition between a radially-contracted configuration and a radially-expanded configuration. In some embodiments, expansion or contraction of the atrial anchoring arms between the radially-contracted and radially-expanded configurations thereof may be independent of the expansion or contraction of the ventricular anchoring legs between the radially-contracted and radially-expanded configurations thereof. For example, the atrial anchoring arms may be in a radially-contracted configuration while the ventricular anchoring legs may be in a radially-expanded configuration. In some other embodiments, the atrial anchoring arms may be in a radially-contracted configuration while the ventricular anchoring legs are also in a radially-contracted configuration. Similarly, there may be embodiments when the atrial anchoring arms are in a radially-expanded configuration while the ventricular anchoring legs may be in a radially-contracted or a radially-expanded configuration. FIG. 5A shows an exemplary prosthetic valve in which the atrial anchoring arms 2440, ventricular anchoring legs 2240, and annular valve body 2020 are in a radially-contracted configuration. FIG. 5B shows an exemplary prosthetic valve in which the plurality of ventricular anchoring legs 2240 are radially-expanded but the atrial anchoring arms 2440 and annular valve body 2020 remain in the radially-contracted configuration. FIG. 5C shows an exemplary prosthetic valve in which the atrial anchoring arms 2440 are radially-expanded but the ventricular anchoring legs 2240 and annular valve body 2020 remain in the radially-contracted configuration. FIG. 5D shows an exemplary prosthetic valve in which both the atrial anchoring arms 2440 and the ventricular anchoring legs 2240 are radially-expanded, while the annular valve body 2020 remains in the radially-contracted configuration. FIG. 5E shows an exemplary prosthetic valve in which the atrial anchoring arms 2440, ventricular anchoring legs 2240, and annular valve body 2020 are radially-expanded. FIG. 10A-H shows the deployment of an exemplary valve, where the atrial anchoring arms and the ventricular anchoring can each transition between different configurations independently of the other.

In some embodiments, the annular valve body may be configured in a radially-contracted configuration while the atrial anchoring arms and ventricular anchoring legs are configured in a radially-expanded configuration. A volume may be formed between the atrial anchoring arms and ventricular anchoring legs in such a configuration. For example, as depicted in FIG. 5D, the volume between the atrial anchoring arms 2440 and ventricular anchoring legs 2240 may be formed when the arms and legs are expanded but the annular valve body remains radially contracted. As discussed above, the annular valve body may be configured to radially expand, thus decreasing the distance between the arms and legs. For example, as depicted in FIG. 5E, the annular valve body may expand to a radially-expanded configuration, bring the atrial anchoring arms 2440 and ventricular anchoring legs 2240 closer together. As a result, the volume between the atrial anchoring arms and ventricular anchoring legs may be greater when the annular valve body is in a radially-contracted configuration than when the annular valve body is in a radially-expanded configuration. Said another way, the volume between the atrial anchoring arms and ventricular anchoring legs may decrease after the annular valve body radially expands. For example, the volume 4000 depicted in FIG. 4B may be bounded by the inner surface of the valve body 4020, the inner atrially-facing leg surface 1248 and the ventricularly facing arm surface 2449. When the annular valve body radially expands, the volume 4000 may be decreased.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A prosthetic valve for implantation within a native mitral valve, the prosthetic valve comprising:
   an annular valve body;
   a plurality of atrial anchoring arms configured to extend radially outward from the annular valve body, wherein the arms are configured to engage an atrial portion of the native mitral valve;
   a plurality of ventricular anchoring legs configured to extend radially outward from the annular valve body, wherein the ventricular anchoring legs are configured to engage a ventricular portion of the native mitral valve; and
   a blood-inflatable cuff containing at least one interior volume formed between a first cuff sheet and a second cuff sheet that is open to blood flow, wherein the blood-inflatable cuff is at least partially situated between the arms and legs,
   wherein the atrial anchoring arms and the ventricular anchoring legs are positioned relative to each other such that when the atrial anchoring arms and ventricular anchoring legs engage the native mitral valve, a volume bounded by the annular valve body, the atrial anchoring arms, and the ventricular anchoring legs is configured to be substantially filled with tissue such that the volume is devoid of gaps;
   wherein the blood-inflatable cuff is configured to press against the tissue in the volume when inflated with blood; and
   wherein a portion of at least one atrial anchoring arm and a portion of at least one ventricular anchoring leg are configured to be aligned in a common lateral plane when in a radially-expanded configuration.

2. The prosthetic valve of claim 1, wherein the volume between the atrial anchoring arms and ventricular anchoring legs is formed between:
   an outer surface of the annular valve body,
   surfaces of the ventricular anchoring legs facing toward an atrium, and
   surfaces of the atrial anchoring arms facing toward a ventricle.

3. The prosthetic valve of claim 1, wherein the portions of the at least one ventricular anchoring leg and the at least one atrial anchoring arm are configured to be overlapping.

4. The prosthetic valve of claim 3, wherein a circumference formed by the overlapping portions of the at least one ventricular anchoring leg and the at least one atrial anchoring arm forms an outer boundary of the volume.

5. The prosthetic valve of claim 1, wherein at least one atrial anchoring arm includes:
   a first portion configured to extend toward a ventricle, and
   a second portion configured to extend toward an atrium.

6. The prosthetic valve of claim 5, wherein the first portion of the at least one atrial anchoring arm is configured to form a boundary of the volume between the atrial anchoring arms and ventricular anchoring legs.

7. The prosthetic valve of claim 5, wherein the second portion is situated radially outward from the volume between the atrial anchoring arms and ventricular anchoring legs.

8. The prosthetic valve of claim 5, wherein the second portion is situated radially outward from the first portion.

9. The prosthetic valve of claim 5, wherein the first portion has a flexibility that varies from a radially inner end of the first portion to a radially outer end of the first portion.

10. The prosthetic valve of claim 1, wherein the diameter of an outer circumference defined by terminal ends of the ventricular anchoring legs is between 1.6 and 1.8 times larger than a diameter of an inner circumference of the annular valve body.

11. The prosthetic valve of claim 10, wherein the inner circumference of the annular valve body is defined by an inner surface of the annular valve body to which prosthetic leaflets are coupled.

12. The prosthetic valve of claim 1, wherein the atrial anchoring arms and ventricular anchoring legs are angularly offset from each other.

13. The prosthetic valve of claim 1, wherein at least one ventricular anchoring leg includes at least one curved portion.

14. The prosthetic valve of claim 1, wherein a radially inner-most portion of at least one atrial anchoring arm is configured to extend toward an atrium.

15. The prosthetic valve of claim 1, wherein the entire length of at least one ventricular anchoring leg is configured to extend toward an atrium.

16. The prosthetic valve of claim 1, wherein the annular valve body includes:
   an atrial end,
   a ventricular end opposite the atrial end, and
   an intermediate portion extending between the atrial end and the ventricular end; and
   wherein the atrial anchoring arms and ventricular anchoring legs are configured to extend from the intermediate portion.

17. The prosthetic valve of claim 1, wherein the annular valve body includes:
   an annular outer frame; and
   an inner frame situated at least partially within the annular outer frame,
   wherein the atrial anchoring arms extend from the inner frame and the ventricular anchoring legs extend from the annular outer frame.

18. The prosthetic valve of claim 17, wherein the ventricular anchoring legs are configured to deflect radially outward while the atrial anchoring arms remain in a radially-contracted configuration.

19. The prosthetic valve of claim 18, wherein the radially-contracted configuration is a delivery configuration and the radially-expanded configuration is a deployed configuration.

20. The prosthetic valve of claim 1, wherein the volume between the atrial anchoring arms and ventricular anchoring legs is greater when the annular valve body is configured in a radially-contracted configuration than when the annular valve body is configured in the radially-expanded configuration.

21. The prosthetic valve of claim 20, wherein the radially-contracted configuration is a delivery configuration and the radially-expanded configuration is a deployed configuration.

22. The prosthetic valve of claim 1, wherein the volume between the atrial anchoring arms and ventricular anchoring legs of the annular valve body decreases after the annular valve body radially expands.

* * * * *